United States Patent
Strem

(10) Patent No.: US 9,682,130 B2
(45) Date of Patent: Jun. 20, 2017

(54) VIRAL CONJUNCTIVITIS TREATMENT USING RANPIRNASE AND/OR AMPHINASE

(71) Applicant: Okogen, LLC, Encinitas, CA (US)

(72) Inventor: Brian Strem, Encinitas, CA (US)

(73) Assignee: Okogen, LLC, Encinitas, CA (US)

(*) Notice: Subject to any disclaimer, the term of this patent is extended or adjusted under 35 U.S.C. 154(b) by 0 days.

(21) Appl. No.: 15/275,442

(22) Filed: Sep. 25, 2016

(65) Prior Publication Data

US 2017/0087223 A1     Mar. 30, 2017

Related U.S. Application Data

(60) Provisional application No. 62/233,267, filed on Sep. 25, 2015.

(51) Int. Cl.
*A61K 38/46* (2006.01)
*A61K 9/00* (2006.01)

(52) U.S. Cl.
CPC .......... *A61K 38/465* (2013.01); *A61K 9/0048* (2013.01); *A61K 9/0051* (2013.01); *C12Y 301/27* (2013.01)

(58) Field of Classification Search
CPC ... A61K 38/465; A61K 9/0051; A61K 9/0048
USPC ....................................................... 424/94.6
See application file for complete search history.

(56) References Cited

U.S. PATENT DOCUMENTS 5,326,347 A * 7/1994 Cumming ................. A61F 2/16
                                                                    623/6.38
2016/0361392 A1* 12/2016 Squiquera ............. A61K 38/465

OTHER PUBLICATIONS

Liu et al. N-Terminal Glutamate to Pyoglutamate Conversion in Vivo for Human IgG2 Antibodies; The Journal of Biological Chemistry, vol. 286, No. 13 (2011) pp. 11211-11217.*

* cited by examiner

*Primary Examiner* — Scott Long
*Assistant Examiner* — Paul Martin
(74) *Attorney, Agent, or Firm* — One3 IP Management, P.C.; Dean G. Stathakis; Peter D. Weinstein

(57) ABSTRACT

The present specification discloses Ranpirnase and Amphinase, compositions comprising Ranpirnase and/or Amphinase, and methods and uses to treat a viral conjunctivitis, an epidemic keratoconjunctivitis, and/or a pharyngoconjunctival fever, reduce or suppress a level of virus or viral titer, reduce or suppress viral replication, reduce or suppress protein synthesis, reduce or suppress a level of a tRNA, reduce or suppress a level of an inflammation inducing molecule and/or an inflammation inducing prostaglandin, stimulate or enhance a peroxisome proliferator-activated receptor (PPAR) pathway signal, promote the resolving phenotypic change of M1 to M2, modulate Th1 and Th2 cytokines, and/or reduce or suppress a NFκB pathway signal using Ranpirnase, Amphinase or compositions comprising Ranpirnase and/or Amphinase.

20 Claims, No Drawings

SEQUENCE LISTING

<160> NUMBER OF SEQ ID NOS: 39

<210> SEQ ID NO 1
<211> LENGTH: 127
<212> TYPE: PRT
<213> ORGANISM: Rana pipiens

<400> SEQUENCE: 1

Met Phe Pro Lys Phe Ser Phe Leu Leu Ile Phe Ala Val Val Leu Ser
1               5                   10                  15

Leu Thr His Lys Ser Leu Cys Gln Asp Trp Leu Thr Phe Gln Lys Lys
            20                  25                  30

His Ile Thr Asn Thr Arg Asp Val Asp Cys Asp Asn Ile Met Ser Thr
        35                  40                  45

Asn Leu Phe His Cys Lys Asp Lys Asn Thr Phe Ile Tyr Ser Arg Pro
    50                  55                  60

Glu Pro Val Lys Ala Ile Cys Lys Gly Ile Ile Ala Ser Lys Asn Val
65                  70                  75                  80

Leu Thr Thr Ser Glu Phe Tyr Leu Ser Asp Cys Asn Val Thr Ser Arg
                85                  90                  95

Pro Cys Lys Tyr Lys Leu Lys Lys Ser Thr Asn Lys Phe Cys Val Thr
            100                 105                 110

Cys Glu Asn Gln Ala Pro Val His Phe Val Gly Val Gly Ser Cys
        115                 120                 125

<210> SEQ ID NO 2
<211> LENGTH: 104
<212> TYPE: PRT
<213> ORGANISM: Rana pipiens

<400> SEQUENCE: 2

Gln Asp Trp Leu Thr Phe Gln Lys Lys His Ile Thr Asn Thr Arg Asp
1               5                   10                  15

Val Asp Cys Asp Asn Ile Met Ser Thr Asn Leu Phe His Cys Lys Asp
            20                  25                  30

Lys Asn Thr Phe Ile Tyr Ser Arg Pro Glu Pro Val Lys Ala Ile Cys
        35                  40                  45

Lys Gly Ile Ile Ala Ser Lys Asn Val Leu Thr Thr Ser Glu Phe Tyr
    50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Ser Cys
            100

<210> SEQ ID NO 3
<211> LENGTH: 104
<212> TYPE: PRT
<213> ORGANISM: Artificial Sequence
<220> FEATURE:
<223> OTHER INFORMATION: Recombinant Ranpirnase variant

<400> SEQUENCE: 3

Glu Asp Trp Leu Thr Phe Gln Lys Lys His Ile Thr Asn Thr Arg Asp
1               5                   10                  15

Val Asp Cys Asp Asn Ile Leu Ser Thr Asn Leu Phe His Cys Lys Asp
            20                  25                  30

```
Lys Asn Thr Phe Ile Tyr Ser Arg Pro Glu Pro Val Lys Ala Ile Cys
            35                  40                  45

Lys Gly Ile Ile Ala Ser Lys Asn Val Leu Thr Thr Ser Glu Phe Tyr
 50                      55                  60

Leu Ser Asp Cys Asn Val Thr Ser Arg Pro Cys Lys Tyr Lys Leu Lys
 65                  70                  75                  80

Lys Ser Thr Asn Lys Phe Cys Val Thr Cys Glu Asn Gln Ala Pro Val
                 85                  90                  95

His Phe Val Gly Val Gly Ser Cys
                100

<210> SEQ ID NO 4
<211> LENGTH: 104
<212> TYPE: PRT
<213> ORGANISM: Artificial Sequence
<220> FEATURE:
<223> OTHER INFORMATION: Ranpirnase variant

<400> SEQUENCE: 4

Glu Asp Trp Leu Thr Phe Gln Lys Lys His Val Thr Asn Thr Arg Asp
 1               5                  10                  15

Val Asp Cys Asn Asn Ile Leu Ser Thr Asn Leu Phe His Cys Lys Asp
                 20                  25                  30

Lys Asn Thr Phe Ile Tyr Ser Arg Pro Glu Pro Val Lys Ala Ile Cys
            35                  40                  45

Lys Gly Ile Ile Ala Ser Lys Asn Val Leu Thr Thr Ser Glu Phe Tyr
 50                      55                  60

Leu Ser Asp Cys Asn Val Thr Ser Arg Pro Cys Lys Tyr Lys Leu Lys
 65                  70                  75                  80

Lys Ser Thr Asn Lys Phe Cys Val Thr Cys Glu Asn Gln Ala Pro Val
                 85                  90                  95

His Phe Val Gly Val Gly Arg Cys
                100

<210> SEQ ID NO 5
<211> LENGTH: 104
<212> TYPE: PRT
<213> ORGANISM: Artificial Sequence
<220> FEATURE:
<223> OTHER INFORMATION: Recombinant Ranpirnase variant

<400> SEQUENCE: 5

Gln Asp Trp Leu Thr Phe Gln Lys Lys His Ile Thr Asn Thr Arg Asp
 1               5                  10                  15

Val Asp Cys Asp Asn Ile Leu Ser Thr Asn Leu Phe His Cys Lys Asp
                 20                  25                  30

Lys Asn Thr Phe Ile Tyr Ser Arg Pro Glu Pro Val Lys Ala Ile Cys
            35                  40                  45

Lys Gly Ile Ile Ala Ser Lys Asn Val Leu Thr Thr Ser Glu Phe Tyr
 50                      55                  60

Leu Ser Asp Cys Asn Val Thr Cys Arg Pro Cys Lys Tyr Lys Leu Lys
 65                  70                  75                  80

Lys Ser Thr Asn Lys Phe Cys Val Thr Cys Glu Asn Gln Ala Pro Val
                 85                  90                  95

His Phe Val Gly Val Gly Ser Cys
                100

<210> SEQ ID NO 6
```

-continued

```
<211> LENGTH: 104
<212> TYPE: PRT
<213> ORGANISM: Artificial Sequence
<220> FEATURE:
<223> OTHER INFORMATION: Recombinant Ranpirnase variant

<400> SEQUENCE: 6

Gln Asp Trp Leu Thr Phe Gln Lys Lys His Ile Thr Asn Thr Arg Asp
1               5                   10                  15

Val Asp Cys Asp Asn Ile Met Ser Thr Asn Leu Phe His Cys L

```
Lys Gly Ile Ile Ala Ser Lys Asn Val Leu Thr Thr Ser Glu Phe Tyr
    50                  55                  60

Leu Ser Asp Cys Asn Val Thr Ser Arg Pro Cys Lys Tyr Lys Leu Lys
65                  70                  75                  80

Lys Ser Thr Asn Lys Phe Ala Val Thr Cys Glu Asn Gln Ala Pro Val
                    85                  90                  95

His Phe Val Gly Val Gly Ser Ala
            100
```

<210> SEQ ID NO 9
<211> LENGTH: 104
<212> TYPE: PRT
<213> ORGANISM: Artificial Sequence
<220> FEATURE:
<223> OTHER INFORMATION: Recombinant Ranpirnase variant

<400> SEQUENCE: 9

```
Gln Asp Trp Leu Thr Phe Gln Lys Lys His Ile Thr Asn Thr Arg Asp
1               5                   10                  15

Val Asp Cys Asp Asn Ile Leu Ser Thr Asn Leu Phe His Cys Lys Asp
                20                  25                  30

Lys Asn Thr Phe Ile Tyr Ser Arg Pro Glu Pro Val Lys Ala Ile Cys
            35                  40                  45

Lys Gly Ile Ile Ala Ser Lys Asn Val Leu Thr Thr Ser Glu Phe Tyr
    50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Asn Cys Ala Asn Gln Ala Pro Val
                    85                  90                  95

His Phe Val Gly Val Gly Ser Cys
            100
```

<210> SEQ ID NO 10
<211> LENGTH: 104
<212> TYPE: PRT
<213> ORGANISM: Artificial Sequence
<220> FEATURE:
<223> OTHER INFORMATION: Recombinant Ranpirnase variant

<400> SEQUENCE: 10

```
Gln Asp Trp Leu Thr Phe Gln Lys Lys His Ile Thr Asn Thr Arg Asp
1               5                   10                  15

Val Asp Cys Asp Asn Ile Met Ser Thr Asn Leu Phe His Cys Lys Asp
                20                  25                  30

Lys Asn Thr Phe Ile Tyr Ser Arg Pro Glu Pro Val Lys Ala Ile Cys
            35                  40                  45

Lys Gly Ile Ile Ala Ser Lys Asn Val Leu Thr Thr Ser Glu Phe Tyr
    50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Asn Cys Ala Asn Gln Ala Pro Val
                    85                  90                  95

His Phe Val Gly Val Gly Ser Cys
            100
```

<210> SEQ ID NO 11
<211> LENGTH: 104
<212> TYPE: PRT
<213> ORGANISM: Artificial Sequence

```
<220> FEATURE:
<223> OTHER INFORMATION: Recombinant Ranpirnase variant

<400> SEQUENCE: 11

Gln Asp Trp Leu Thr Phe Gln Lys Lys His Ile Thr Asn Thr Arg Asp
1               5                   10                  15

Val Asp Cys Asp Asn Ile Leu Ser Thr Asn Leu Phe His Ala Lys Asp
            20                  25                  30

Lys Asn Thr Phe Ile Tyr Ser Arg Pro Glu Pro Val Lys Ala Ile Cys
        35                  40                  45

Lys Gly Ile Ile Ala Ser Lys Asn Val Leu Thr Thr Ser Glu Phe Tyr
    50                  55                  60

Leu Ser Asp Cys Asn Val Thr Ser Arg Pro Ala Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Ser Cys
            100

<210> SEQ ID NO 12
<211> LENGTH: 104
<212> TYPE: PRT
<213> ORGANISM: Artificial Sequence
<220> FEATURE:
<223> OTHER INFORMATION: Recombinant Ranpirnase variant

<400> SEQUENCE: 12

Gln Asp Trp Leu Thr Phe Gln Lys Lys His Ile Thr Asn Thr Arg Asp
1               5                   10                  15

Val Asp Cys Asp Asn Ile Met Ser Thr Asn Leu Phe His Ala Lys Asp
            20                  25                  30

Lys Asn Thr Phe Ile Tyr Ser Arg Pro Glu Pro Val Lys Ala Ile Cys
        35                  40                  45

Lys Gly Ile Ile Ala Ser Lys Asn Val Leu Thr Thr Ser Glu Phe Tyr
    50                  55                  60

Leu Ser Asp Cys Asn Val Thr Ser Arg Pro Ala Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Ser Cys
            100

<210> SEQ ID NO 13
<211> LENGTH: 102
<212> TYPE: PRT
<213> ORGANISM: Artificial Sequence
<220> FEATURE:
<223> OTHER INFORMATION: Recombinant Ranpirnase variant

<400> SEQUENCE: 13

Gln Asp Trp Leu Thr Phe Gln Lys Lys His Ile Thr Asn Thr Arg Asp
1               5                   10                  15

Val Asp Cys Asp Asn Ile Leu Ser Thr Asn Leu Phe His Cys Lys Asp
            20                  25                  30

Lys Asn Thr Phe Ile Tyr Ser Arg Pro Glu Pro Val Lys Ala Ile Cys
        35                  40                  45

Lys Gly Ile Ile Ala Ser Lys Asn Val Leu Thr Thr Ser Glu Phe Tyr
    50                  55                  60
```

```
Leu Ser Asp Cys Asn Val Thr Ser Arg Pro Cys Lys Tyr Lys Leu Lys
 65                  70                  75                  80

Lys Ser Thr Asn Lys Phe Ser Val Thr Cys Glu Asn Gln Ala Pro Val
                 85                  90                  95

His Phe Val Gly Val Gly
            100
```

<210> SEQ ID NO 14
<211> LENGTH: 102
<212> TYPE: PRT
<213> ORGANISM: Artificial Sequence
<220> FEATURE:
<223> OTHER INFORMATION: Recombinant Ranpirnase variant

<400> SEQUENCE: 14

```
Gln Asp Trp Leu Thr Phe Gln Lys Lys His Ile Thr Asn Thr Arg Asp
  1               5                  10                  15

Val Asp Cys Asp Asn Ile Met Ser Thr Asn Leu Phe His Cys Lys Asp
                 20                  25                  30

Lys Asn Thr Phe Ile Tyr Ser Arg Pro Glu Pro Val Lys Ala Ile Cys
                 35                  40                  45

Lys Gly Ile Ile Ala Ser Lys Asn Val Leu Thr Thr Ser Glu Phe Tyr
     50                  55                  60

Leu Ser Asp Cys Asn Val Thr Ser Arg Pro Cys Lys Tyr Lys Leu Lys
 65                  70                  75                  80

Lys Ser Thr Asn Lys Phe Ser Val Thr Cys Glu Asn Gln Ala Pro Val
                 85                  90                  95

His Phe Val Gly Val Gly
            100
```

<210> SEQ ID NO 15
<211> LENGTH: 117
<212> TYPE: PRT
<213> ORGANISM: Rana dybowskii

<400> SEQUENCE: 15

```
Leu Phe Ala Val Val Leu Ser Leu Thr His Lys Phe Leu Cys Gln Asp
  1               5                  10                  15

Trp Lys Thr Phe Gln Asp Lys His Leu Thr Lys Thr Arg Asp Val Asp
                 20                  25                  30

Cys Asp Asn Val Leu Ser Lys Pro Leu Phe Asn Cys Lys Asp Arg Asn
                 35                  40                  45

Thr Phe Ile Phe Ser Arg Pro Glu Pro Val Lys Ala Leu Cys Lys Gly
     50                  55                  60

Val Lys Asp Lys Asn Val Leu Ser Arg Ser Glu Phe Tyr Leu Ser Asp
 65                  70                  75                  80

Cys Asn Val Thr Thr Arg His Cys Lys Tyr Lys Leu Lys Lys Lys Ile
                 85                  90                  95

Asn Thr Ile Cys Ile Thr Cys Arg Gly Glu Ala Pro His Phe Val
            100                 105                 110

Gly Val Gly Ser Cys
        115
```

<210> SEQ ID NO 16
<211> LENGTH: 104
<212> TYPE: PRT
<213> ORGANISM: Rana dybowskii

<400> SEQUENCE: 16

Gln Asp Trp Lys Thr Phe Gln Lys Lys His Leu Thr Lys Ala Arg Asp
1               5                   10                  15

Ile Lys Cys Asp Asn Ile Met Ser Lys Thr Leu Phe Asn Cys Lys Asp
            20                  25                  30

Thr Asn Thr Phe Ile Phe Ser Leu Pro Gly Pro Val Lys Ala Leu Cys
        35                  40                  45

Arg Gly Ile Lys Val Ser Lys Asn Val Leu Ser Arg Ser Glu Phe Asp
    50                  55                  60

Leu Ser Glu Cys Asn Val Lys Ser Lys Pro Cys Lys Tyr Lys Leu Lys
65                  70                  75                  80

Lys Lys Ser Asp Gly Ile Cys Ile Thr Cys Arg Asp Glu Ala Pro Val
                85                  90                  95

His Phe Val Gly Val Gly Ser Cys
            100

<210> SEQ ID NO 17
<211> LENGTH: 104
<212> TYPE: PRT
<213> ORGANISM: Rana dybowskii

<400> SEQUENCE: 17

Gln Asp Trp Lys Thr Phe Gln Lys Lys His Leu Thr Asn Thr Arg Asn
1               5                   10                  15

Ile Lys Cys Asp Lys Ile Met Pro Ile Asn Leu Phe His Cys Lys Tyr
            20                  25                  30

Arg Asn Thr Phe Ile Tyr Ser Arg Pro Arg Gly Val Glu Asn Leu Cys
        35                  40                  45

Arg Gly Lys Ile Asn Ala Thr Asn Val Ser Ser Ser Lys Phe Ala
    50                  55                  60

Leu Phe Glu Cys Ile Glu Lys Ser Arg Pro Cys Lys Tyr Lys Leu Lys
65                  70                  75                  80

Lys Gln Thr Asn Val Ile Cys Ile Thr Cys Glu His Lys Val Pro Val
                85                  90                  95

His Phe Val Gly Val Gly Ser Cys
            100

<210> SEQ ID NO 18
<211> LENGTH: 129
<212> TYPE: PRT
<213> ORGANISM: Rana catesbeiana

<400> SEQUENCE: 18

Met Phe Pro Lys Phe Ser Phe Leu Leu Ile Phe Ala Ile Val Leu Ser
1               5                   10                  15

Leu Thr His Lys Ser Leu Cys Gln Asp Trp Ala Thr Phe Lys Lys Lys
            20                  25                  30

His Leu Thr Asp Thr Trp Asp Val Asp Cys Asp Asn Leu Met Pro Thr
        35                  40                  45

Ser Leu Phe Asp Cys Lys Asp Lys Asn Thr Phe Ile Tyr Ser Leu Pro
    50                  55                  60

Gly Pro Val Lys Ala Leu Cys Arg Gly Val Ile Phe Ser Ala Asp Val
65                  70                  75                  80

Leu Ser Asn Ser Glu Phe Tyr Leu Ala Glu Cys Asn Val Lys Pro Arg
                85                  90                  95

Lys Pro Cys Lys Tyr Lys Leu Lys Ser Ser Asn Arg Ile Cys Ile
            100                 105                 110

```
Arg Cys Glu His Glu Leu Pro Val His Phe Ala Gly Val Gly Ile Cys
        115                 120                 125
Pro

<210> SEQ ID NO 19
<211> LENGTH: 106
<212> TYPE: PRT
<213> ORGANISM: Rana catesbeiana

<400> SEQUENCE: 19

Gln Asp Trp Ala Thr Phe Lys Lys Lys His Leu Thr Asp Thr Trp Asp
1               5                   10                  15

Val Asp Cys Asp Asn Leu Met Pro Thr Ser Leu Phe Asp Cys Lys Asp
            20                  25                  30

Lys Asn Thr Phe Ile Tyr Ser Leu Pro Gly Pro Val Lys Ala Leu Cys
        35                  40                  45

Arg Gly Val Ile Phe Ser Ala Asp Val Leu Ser Asn Ser Glu Phe Tyr
    50                  55                  60

Leu Ala Glu Cys Asn Val Lys Pro Arg Lys Pro Cys Lys Tyr Lys Leu
65                  70                  75                  80

Lys Lys Ser Ser Asn Arg Ile Cys Ile Arg Cys Glu His Glu Leu Pro
                85                  90                  95

Val His Phe Ala Gly Val Gly Ile Cys Pro
            100                 105

<210> SEQ ID NO 20
<211> LENGTH: 128
<212> TYPE: PRT
<213> ORGANISM: Rana catesbeiana

<400> SEQUENCE: 20

Met Phe Pro Lys Phe Ser Phe Leu Leu Ile Phe Ala Val Val Leu Ser
1               5                   10                  15

Leu Thr His Lys Ser Leu Cys Gln Asn Trp Glu Thr Phe Gln Lys Lys
            20                  25                  30

His Leu Thr Asn Ile Leu Asp Ile Asn Cys Asp Val Glu Met Ala Lys
        35                  40                  45

Ala Leu Phe Asn Cys Lys Glu Met Asn Thr Phe Ile Tyr Ala Leu Pro
    50                  55                  60

Gly Arg Val Gln Ala Leu Cys Lys Asn Ile Lys Asp Asn Thr Glu Val
65                  70                  75                  80

Leu Ser Thr Asp Thr Phe Tyr Leu Pro Glu Cys Asn Arg Ile Lys Leu
                85                  90                  95

Pro Cys His Tyr Lys Leu Lys Lys Pro Leu Glu Lys Ile Cys Ile Thr
            100                 105                 110

Cys Val Asn Glu Leu Pro Ile His Phe Ala Gly Val Gly Ser Cys Pro
        115                 120                 125

<210> SEQ ID NO 21
<211> LENGTH: 105
<212> TYPE: PRT
<213> ORGANISM: Rana catesbeiana

<400> SEQUENCE: 21

Gln Asn Trp Glu Thr Phe Gln Lys Lys His Leu Thr Asn Ile Leu Asp
1               5                   10                  15

Ile Asn Cys Asp Val Glu Met Ala Lys Ala Leu Phe Asn Cys Lys Glu
```

```
                        20                  25                  30
Met Asn Thr Phe Ile Tyr Ala Leu Pro Gly Arg Val Gln Ala Leu Cys
                35                  40                  45

Lys Asn Ile Lys Asp Asn Thr Glu Val Leu Ser Thr Asp Thr Phe Tyr
            50                  55                  60

Leu Pro Glu Cys Asn Arg Ile Lys Leu Pro Cys His Tyr Lys Leu Lys
65                  70                  75                  80

Lys Pro Leu Glu Lys Ile Cys Ile Thr Cys Val Asn Glu Leu Pro Ile
                85                  90                  95

His Phe Ala Gly Val Gly Ser Cys Pro
                100                 105

<210> SEQ ID NO 22
<211> LENGTH: 128
<212> TYPE: PRT
<213> ORGANISM: Rana catesbeiana

<400> SEQUENCE: 22

Met Phe Pro Lys Phe Ser Phe Leu Leu Ile Phe Ala Val Val Leu Ser
1               5                   10                  15

Leu Thr His Lys Ser Leu Cys Gln Asn Trp Glu Thr Phe Gln Lys Lys
                20                  25                  30

His Leu Thr Asn Ile Leu Asp Ile Asn Cys Asp Val Glu Met Ala Lys
            35                  40                  45

Ala Leu Phe Asn Cys Lys Glu Met Asn Thr Phe Ile Tyr Ala Leu Pro
        50                  55                  60

Gly Arg Val Gln Ala Leu Cys Lys Asn Ile Arg Asp Asn Thr Asp Val
65                  70                  75                  80

Leu Ser Arg Asp Ala Phe Leu Leu Pro Gln Cys Asp Arg Ile Lys Leu
                85                  90                  95

Pro Cys His Tyr Lys Leu Ser Ser Ser Thr Asn Thr Ile Cys Ile Thr
                100                 105                 110

Cys Val Asn Gln Leu Pro Ile His Phe Ala Gly Val Gly Ser Cys Pro
            115                 120                 125

<210> SEQ ID NO 23
<211> LENGTH: 105
<212> TYPE: PRT
<213> ORGANISM: Rana catesbeiana

<400> SEQUENCE: 23

Gln Asn Trp Glu Thr Phe Gln Lys Lys His Leu Thr Asn Ile Leu Asp
1               5                   10                  15

Ile Asn Cys Asp Val Glu Met Ala Lys Ala Leu Phe Asn Cys Lys Glu
                20                  25                  30

Met Asn Thr Phe Ile Tyr Ala Leu Pro Gly Arg Val Gln Ala Leu Cys
                35                  40                  45

Lys Asn Ile Arg Asp Asn Thr Asp Val Leu Ser Arg Asp Ala Phe Leu
            50                  55                  60

Leu Pro Gln Cys Asp Arg Ile Lys Leu Pro Cys His Tyr Lys Leu Ser
65                  70                  75                  80

Ser Ser Thr Asn Thr Ile Cys Ile Thr Cys Val Asn Gln Leu Pro Ile
                85                  90                  95

His Phe Ala Gly Val Gly Ser Cys Pro
                100                 105
```

-continued

```
<210> SEQ ID NO 24
<211> LENGTH: 131
<212> TYPE: PRT
<213> ORGANISM: Rana catesbeiana

<400> SEQUENCE: 24

Met Phe Pro Lys Phe Ser Phe Leu Leu Ile Phe Ala Val Val Leu Ser
1               5                   10                  15

Leu Thr His Lys Ser Leu Cys Gln Asp Trp Glu Thr Phe Gln Lys Lys
            20                  25                  30

His Leu Thr Asp Thr Val Asp Val Asn Cys Asp Val Glu Met Gln Lys
        35                  40                  45

Ala Leu Phe Asn Cys Lys Gln Thr Asn Thr Phe Ile Phe Ala Arg Pro
    50                  55                  60

Pro Arg Val Gln Ala Leu Cys Lys Asn Ile Lys Asp Asn Thr Asp Val
65                  70                  75                  80

Leu Ser Arg Asp Glu Phe Tyr Leu Pro Glu Cys Asn Arg Thr Lys Leu
                85                  90                  95

Pro Cys His Tyr Lys Leu Lys Lys Pro Leu Asn Thr Ile Cys Leu Thr
            100                 105                 110

Cys Arg Lys Glu Leu Pro Val His Phe Ala Gly Val Gly Lys Cys Pro
        115                 120                 125

Glu Lys Val
    130

<210> SEQ ID NO 25
<211> LENGTH: 108
<212> TYPE: PRT
<213> ORGANISM: Rana catesbeiana

<400> SEQUENCE: 25

Gln Asp Trp Glu Thr Phe Gln Lys Lys His Leu Thr Asp Thr Val Asp
1               5                   10                  15

Val Asn Cys Asp Val Glu Met Gln Lys Ala Leu Phe Asn Cys Lys Gln
            20                  25                  30

Thr Asn Thr Phe Ile Phe Ala Arg Pro Pro Arg Val Gln Ala Leu Cys
        35                  40                  45

Lys Asn Ile Lys Asp Asn Thr Asp Val Leu Ser Arg Asp Glu Phe Tyr
    50                  55                  60

Leu Pro Glu Cys Asn Arg Thr Lys Leu Pro Cys His Tyr Lys Leu Lys
65                  70                  75                  80

Lys Pro Leu Asn Thr Ile Cys Leu Thr Cys Arg Lys Glu Leu Pro Val
                85                  90                  95

His Phe Ala Gly Val Gly Lys Cys Pro Glu Lys Val
            100                 105

<210> SEQ ID NO 26
<211> LENGTH: 105
<212> TYPE: PRT
<213> ORGANISM: Rana catesbeiana

<400> SEQUENCE: 26

Gln Asn Trp Glu Thr Phe Gln Lys Lys His Leu Thr Asp Thr Arg Asp
1               5                   10                  15

Val Lys Cys Asp Ala Glu Met Lys Lys Ala Leu Phe Asp Cys Lys Gln
            20                  25                  30

Lys Asn Thr Phe Ile Tyr Ala Arg Pro Gly Arg Val Gln Ala Leu Cys
        35                  40                  45
```

```
Lys Asn Ile Ile Val Ser Lys Asn Val Leu Ser Thr Asp Glu Phe Tyr
            50                  55                  60

Leu Ser Asp Cys Asn Arg Ile Lys Leu Pro Cys His Tyr Lys Leu Lys
 65                  70                  75                  80

Lys Ser Ser Asn Thr Ile Cys Ile Thr Cys Glu Asn Lys Leu Pro Val
                     85                  90                  95

His Phe Val Ala Val Glu Glu Cys Pro
            100                 105
```

<210> SEQ ID NO 27
<211> LENGTH: 114
<212> TYPE: PRT
<213> ORGANISM: Rana pipens

<400> SEQUENCE: 27

```
Lys Pro Lys Glu Asp Arg Glu Trp Glu Lys Phe Lys Thr Lys His Ile
 1               5                  10                  15

Thr Ser Gln Ser Val Ala Asp Phe Asn Cys Asn Arg Thr Met Asn Asp
            20                  25                  30

Pro Ala Tyr Thr Pro Asp Gly Gln Cys Lys Pro Ile Asn Thr Phe Ile
            35                  40                  45

His Ser Thr Thr Gly Pro Val Lys Glu Ile Cys Arg Arg Ala Thr Gly
 50                  55                  60

Arg Val Asn Lys Ser Ser Thr Gln Gln Phe Thr Leu Thr Thr Cys Lys
 65                  70                  75                  80

Asn Pro Ile Arg Cys Lys Tyr Ser Gln Ser Asn Thr Thr Asn Phe Ile
                 85                  90                  95

Cys Ile Thr Cys Arg Asp Asn Tyr Pro Val His Phe Val Lys Thr Gly
                100                 105                 110

Lys Cys
```

<210> SEQ ID NO 28
<211> LENGTH: 115
<212> TYPE: PRT
<213> ORGANISM: Artificial Sequence
<220> FEATURE:
<223> OTHER INFORMATION: Recombinant Amphinase-2 variant

<400> SEQUENCE: 28

```
Met Lys Pro Lys Glu Asp Arg Glu Trp Glu Lys Phe Lys Thr Lys His
 1               5                  10                  15

Ile Thr Ser Gln Ser Val Ala Asp Phe Asn Cys Asn Arg Thr Met Asn
            20                  25                  30

Asp Pro Ala Tyr Thr Pro Asp Gly Gln Cys Lys Pro Ile Asn Thr Phe
            35                  40                  45

Ile His Ser Thr Thr Gly Pro Val Lys Glu Ile Cys Arg Arg Ala Thr
 50                  55                  60

Gly Arg Val Asn Lys Ser Ser Thr Gln Gln Phe Thr Leu Thr Thr Cys
 65                  70                  75                  80

Lys Asn Pro Ile Arg Cys Lys Tyr Ser Gln Ser Asn Thr Thr Asn Phe
                 85                  90                  95

Ile Cys Ile Thr Cys Arg Asp Asn Tyr Pro Val His Phe Val Lys Thr
                100                 105                 110

Gly Lys Cys
        115
```

```
<210> SEQ ID NO 29
<211> LENGTH: 116
<212> TYPE: PRT
<213> ORGANISM: Artificial Sequence
<220> FEATURE:
<223> OTHER INFORMATION: Recombinant Amphinase-2 variant

<400> SEQUENCE: 29

Met Ala Lys Pro Lys Glu Asp Arg Glu Trp Glu Lys Phe Lys Thr Lys
1               5                   10                  15

His Ile Thr Ser Gln Ser Val Ala Asp Phe Asn Cys Asn Arg Thr Met
                20                  25                  30

Asn Asp Pro Ala Tyr Thr Pro Asp Gly Gln Cys Lys Pro Ile Asn Thr
            35                  40                  45

Phe Ile His Ser Thr Thr Gly Pro Val Lys Glu Ile Cys Arg Arg Ala
    50                  55                  60

Thr Gly Arg Val Asn Lys Ser Ser Thr Gln Gln Phe Thr Leu Thr Thr
65                  70                  75                  80

Cys Lys Asn Pro Ile Arg Cys Lys Tyr Ser Gln Ser Asn Thr Thr Asn
                85                  90                  95

Phe Ile Cys Ile Thr Cys Arg Asp Asn Tyr Pro Val His Phe Val Lys
            100                 105                 110

Thr Gly Lys Cys
        115

<210> SEQ ID NO 30
<211> LENGTH: 121
<212> TYPE: PRT
<213> ORGANISM: Artificial Sequence
<220> FEATURE:
<223> OTHER INFORMATION: Recombinant Amphinase-2 variant

<400> SEQUENCE: 30

Ala Ala Gln Pro Ala Met Ala Lys Pro Lys Glu Asp Arg Glu Trp Glu
1               5                   10                  15

Lys Phe Lys Thr Lys His Ile Thr Ser Gln Ser Val Ala Asp Phe Asn
                20                  25                  30

Cys Asn Arg Thr Met Asn Asp Pro Ala Tyr Thr Pro Asp Gly Gln Cys
            35                  40                  45

Lys Pro Ile Asn Thr Phe Ile His Ser Thr Thr Gly Pro Val Lys Glu
    50                  55                  60

Ile Cys Arg Arg Ala Thr Gly Arg Val Asn Lys Ser Ser Thr Gln Gln
65                  70                  75                  80

Phe Thr Leu Thr Thr Cys Lys Asn Pro Ile Arg Cys Lys Tyr Ser Gln
                85                  90                  95

Ser Asn Thr Thr Asn Phe Ile Cys Ile Thr Cys Arg Asp Asn Tyr Pro
            100                 105                 110

Val His Phe Val Lys Thr Gly Lys Cys
        115                 120

<210> SEQ ID NO 31
<211> LENGTH: 136
<212> TYPE: PRT
<213> ORGANISM: Artificial Sequence
<220> FEATURE:
<223> OTHER INFORMATION: Recombinant Amphinase-2 variant

<400> SEQUENCE: 31

Met Lys Tyr Leu Leu Pro Thr Ala Ala Ala Gly Leu Leu Leu Leu Ala
1               5                   10                  15
```

Ala Gln Pro Ala Met Ala Lys Pro Lys Glu Asp Arg Glu Trp Glu Lys
            20                  25                  30

Phe Lys Thr Lys His Ile Thr Ser Gln Ser Val Ala Asp Phe Asn Cys
         35                  40                  45

Asn Arg Thr Met Asn Asp Pro Ala Tyr Thr Pro Asp Gly Gln Cys Lys
 50                  55                  60

Pro Ile Asn Thr Phe Ile His Ser Thr Thr Gly Pro Val Lys Glu Ile
 65                  70                  75                  80

Cys Arg Arg Ala Thr Gly Arg Val Asn Lys Ser Ser Thr Gln Gln Phe
                 85                  90                  95

Thr Leu Thr Thr Cys Lys Asn Pro Ile Arg Cys Lys Tyr Ser Gln Ser
            100                 105                 110

Asn Thr Thr Asn Phe Ile Cys Ile Thr Cys Arg Asp Asn Tyr Pro Val
        115                 120                 125

His Phe Val Lys Thr Gly Lys Cys
        130                 135

<210> SEQ ID NO 32
<211> LENGTH: 114
<212> TYPE: PRT
<213> ORGANISM: Artificial Sequence
<220> FEATURE:
<223> OTHER INFORMATION: Recombinant Amphinase-2 variant

<400> SEQUENCE: 32

Lys Pro Lys Glu Asp Arg Glu Trp Glu Lys Phe Lys Thr Lys His Ile
 1               5                  10                  15

Thr Ser Gln Ser Val Ala Asp Phe Asn Cys Asn Arg Thr Met Asn Asp
            20                  25                  30

Pro Ala Tyr Thr Pro Asp Gly Gln Cys Lys Pro Ile Asn Thr Phe Ile
         35                  40                  45

His Ser Thr Thr Gly Pro Val Lys Glu Ile Cys Arg Arg Ala Thr Gly
 50                  55                  60

Arg Val Asn Lys Ser Ser Cys Gln Gln Phe Thr Leu Thr Thr Cys Lys
65                  70                  75                  80

Asn Pro Ile Arg Cys Lys Tyr Ser Gln Ser Asn Thr Thr Asn Phe Ile
                 85                  90                  95

Cys Ile Thr Cys Arg Asp Asn Tyr Pro Val His Phe Val Lys Thr Gly
            100                 105                 110

Lys Cys

<210> SEQ ID NO 33
<211> LENGTH: 115
<212> TYPE: PRT
<213> ORGANISM: Artificial Sequence
<220> FEATURE:
<223> OTHER INFORMATION: Recombinant Amphinase-2 variant

<400> SEQUENCE: 33

Met Lys Pro Lys Glu Asp Arg Glu Trp Glu Lys Phe Lys Thr Lys His
 1               5                  10                  15

Ile Thr Ser Gln Ser Val Ala Asp Phe Asn Cys Asn Arg Thr Met Asn
            20                  25                  30

Asp Pro Ala Tyr Thr Pro Asp Gly Gln Cys Lys Pro Ile Asn Thr Phe
         35                  40                  45

Ile His Ser Thr Thr Gly Pro Val Lys Glu Ile Cys Arg Arg Ala Thr
 50                  55                  60

Gly Arg Val Asn Lys Ser Ser Cys Gln Gln Phe Thr Leu Thr Thr Cys
65                  70                  75                  80

Lys Asn Pro Ile Arg Cys Lys Tyr Ser Gln Ser Asn Thr Thr Asn Phe
                85                  90                  95

Ile Cys Ile Thr Cys Arg Asp Asn Tyr Pro Val His Phe Val Lys Thr
            100                 105                 110

Gly Lys Cys
        115

<210> SEQ ID NO 34
<211> LENGTH: 114
<212> TYPE: PRT
<213> ORGANISM: Artificial Sequence
<220> FEATURE:
<223> OTHER INFORMATION: Recombinant Amphinase-2 variant

<400> SEQUENCE: 34

Lys Pro Lys Glu Asp Arg Glu Trp Glu Lys Phe Lys Thr Lys His Ile
1               5                   10                  15

Thr Ser Gln Ser Val Ala Asp Phe Asn Cys Asn Arg Thr Met Asn Asp
            20                  25                  30

Pro Ala Tyr Thr Pro Asp Gly Gln Cys Lys Pro Val Asn Thr Phe Ile
            35                  40                  45

His Ser Thr Thr Gly Pro Val Lys Glu Ile Cys Arg Arg Ala Thr Gly
        50                  55                  60

Arg Val Asn Lys Ser Ser Thr Gln Gln Phe Thr Leu Thr Thr Cys Lys
65                  70                  75                  80

Asn Pro Ile Arg Cys Lys Tyr Ser Gln Ser Asn Thr Thr Asn Phe Ile
                85                  90                  95

Cys Ile Thr Cys Arg Asp Asn Tyr Pro Val His Phe Val Lys Thr Gly
            100                 105                 110

Lys Cys

<210> SEQ ID NO 35
<211> LENGTH: 115
<212> TYPE: PRT
<213> ORGANISM: Artificial Sequence
<220> FEATURE:
<223> OTHER INFORMATION: Recombinant Amphinase-2 variant

<400> SEQUENCE: 35

Met Lys Pro Lys Glu Asp Arg Glu Trp Glu Lys Phe Lys Thr Lys His
1               5                   10                  15

Ile Thr Ser Gln Ser Val Ala Asp Phe Asn Cys Asn Arg Thr Met Asn
            20                  25                  30

Asp Pro Ala Tyr Thr Pro Asp Gly Gln Cys Lys Pro Val Asn Thr Phe
            35                  40                  45

Ile His Ser Thr Thr Gly Pro Val Lys Glu Ile Cys Arg Arg Ala Thr
        50                  55                  60

Gly Arg Val Asn Lys Ser Ser Thr Gln Gln Phe Thr Leu Thr Thr Cys
65                  70                  75                  80

Lys Asn Pro Ile Arg Cys Lys Tyr Ser Gln Ser Asn Thr Thr Asn Phe
                85                  90                  95

Ile Cys Ile Thr Cys Arg Asp Asn Tyr Pro Val His Phe Val Lys Thr
            100                 105                 110

Gly Lys Cys
        115

```
<210> SEQ ID NO 36
<211> LENGTH: 114
<212> TYPE: PRT
<213> ORGANISM: Artificial Sequence
<220> FEATURE:
<223> OTHER INFORMATION: Recombinant Amphinase-2 variant

<400> SEQUENCE: 36
```

Lys Pro Lys Glu Asp Lys Glu Trp Glu Lys Phe Lys Val Lys His Ile
1               5                   10                  15

Thr Ser Gln Ser Val Ala Asp Phe Asn Cys Thr Ser Thr Met Asn Asn
            20                  25                  30

Pro Asp Phe Thr Pro Asp Gly Gln Cys Lys Pro Ile Asn Thr Phe Ile
        35                  40                  45

His Ser Asn Thr Gly Pro Val Lys Glu Ile Cys Arg Arg Ala Ser Gly
    50                  55                  60

Arg Val Asn Lys Ser Ser Thr Gln Gln Phe Pro Leu Thr Thr Cys Lys
65                  70                  75                  80

Asn Pro Lys Arg Cys Lys Tyr Ser Gln Ser Asn Glu Thr Asn Tyr Ile
                85                  90                  95

Cys Ile Thr Cys Arg Asp Asn Tyr Pro Val His Phe Val Lys Ile Gly
            100                 105                 110

Lys Cys

```
<210> SEQ ID NO 37
<211> LENGTH: 115
<212> TYPE: PRT
<213> ORGANISM: Artificial Sequence
<220> FEATURE:
<223> OTHER INFORMATION: Recombinant Amphinase-2 variant

<400> SEQUENCE: 37
```

Met Lys Pro Lys Glu Asp Lys Glu Trp Glu Lys Phe Lys Val Lys His
1               5                   10                  15

Ile Thr Ser Gln Ser Val Ala Asp Phe Asn Cys Thr Ser Thr Met Asn
            20                  25                  30

Asn Pro Asp Phe Thr Pro Asp Gly Gln Cys Lys Pro Ile Asn Thr Phe
        35                  40                  45

Ile His Ser Asn Thr Gly Pro Val Lys Glu Ile Cys Arg Arg Ala Ser
    50                  55                  60

Gly Arg Val Asn Lys Ser Ser Thr Gln Gln Phe Pro Leu Thr Thr Cys
65                  70                  75                  80

Lys Asn Pro Lys Arg Cys Lys Tyr Ser Gln Ser Asn Glu Thr Asn Tyr
                85                  90                  95

Ile Cys Ile Thr Cys Arg Asp Asn Tyr Pro Val His Phe Val Lys Ile
            100                 105                 110

Gly Lys Cys
        115

```
<210> SEQ ID NO 38
<211> LENGTH: 114
<212> TYPE: PRT
<213> ORGANISM: Artificial Sequence
<220> FEATURE:
<223> OTHER INFORMATION: Recombinant Amphinase-2 variant

<400> SEQUENCE: 38
```

Lys Pro Lys Glu Asp Lys Glu Trp Val Lys Phe Lys Ala Lys His Ile

```
                1               5                   10                  15
            Thr Ser Gln Ser Val Ala Asp Phe Asn Cys Asn Lys Thr Met Asn Asp
                            20                  25                  30

Pro Asp Phe Thr Pro Asp Gly Gln Cys Lys Pro Val Asn Thr Phe Ile
                        35                  40                  45

His Ser Asn Thr Gly Pro Val Lys Asp Ile Cys Arg Arg Ala Ser Gly
                    50                  55                  60

Arg Val Asn Lys Ser Ser Thr Gln Gln Phe Pro Leu Thr Thr Cys Asn
            65                  70                  75                  80

Lys Pro Ile Arg Cys Lys Tyr Ser Gln Ser Asn Thr Thr Asn Phe Ile
                            85                  90                  95

Cys Ile Thr Cys Arg Asp Asn Tyr Pro Val His Phe Val Lys Ile Gly
                            100                 105                 110

Lys Cys

<210> SEQ ID NO 39
<211> LENGTH: 115
<212> TYPE: PRT
<213> ORGANISM: Artificial Sequence
<220> FEATURE:
<223> OTHER INFORMATION: Recombinant Amphinase-2 variant

<400> SEQUENCE: 39

Met Lys Pro Lys Glu Asp Lys Glu Trp Val Lys Phe Lys Ala Lys His
            1               5                   10                  15

Ile Thr Ser Gln Ser Val Ala Asp Phe Asn Cys Asn Lys Thr Met Asn
                            20                  25                  30

Asp Pro Asp Phe Thr Pro Asp Gly Gln Cys Lys Pro Val Asn Thr Phe
                        35                  40                  45

Ile His Ser Asn Thr Gly Pro Val Lys Asp Ile Cys Arg Arg Ala Ser
                    50                  55                  60

Gly Arg Val Asn Lys Ser Ser Thr Gln Gln Phe Pro Leu Thr Thr Cys
            65                  70                  75                  80

Asn Lys Pro Ile Arg Cys Lys Tyr Ser Gln Ser Asn Thr Thr Asn Phe
                            85                  90                  95

Ile Cys Ile Thr Cys Arg Asp Asn Tyr Pro Val His Phe Val Lys Ile
                            100                 105                 110

Gly Lys Cys
                    115
```

VIRAL CONJUNCTIVITIS TREATMENT USING RANPIRNASE AND/OR AMPHINASE

This application claims the benefit of priority and the filing date pursuant to 35 U.S.C. §119(e) of U.S. Provisional Patent Application 62/233,267, filed on Sep. 25, 2015, the content of which is hereby incorporated by reference in its entirety.

Conjunctivitis, commonly referred to as pink eye, is an inflammation of the eye causing swelling and irritation. It affects the conjunctiva, the thin transparent membrane that covers the sclera of the eyeball and lines the inner surface of the eyelid. Conjunctivitis is most often caused by a viral or by a bacterial infection, although allergies, chemical irritants, and underlying diseases can also play a role. Symptoms of conjunctivitis include, without limitation, redness in the sclera and/or inner eyelid, ocular itching (itchy eyes), foreign body sensation (gritty or scratchy eyes), burning eyes, blurred vision, increased sensitivity to light or photophobia, swollen inner eyelids, increased tear production, watery discharge, mucopurulent discharge that can crusts over eyelashes while sleeping. Both viral and bacterial conjunctivitis are highly contagious.

Typically caused by pyrogenic bacteria such as *staphylococcus* or *streptococcus*, bacterial conjunctivitis can be treated using antibiotics in the form of eye drops, pills or an ointment. Eye drops or ointments may need to be applied to the inside of the eyelid three to four times a day for five to seven days. Pills may need to be taken for several days. Treatment helps shorten the course of the infection, and associated symptoms, which usually lasts 2 to 21 days. Treatment will also decrease the amount of time an individual suffering from bacterial conjunctivitis is contagious. Unlike bacterial infection, there is currently no effective treatment for viral conjunctivitis.

Although conjunctivitis is typically a self-limited disease, certain forms of conjunctivitis are serious and sight-threatening because the disease can cause cornea scarring. The more severe forms of conjunctivitis include bacterial conjunctivitis caused by gonorrhea and *chlamydia* as well as viral conjunctivitis caused by certain strains of the adeno virus.

Thus there is a need to develop pharmaceutical compositions and treatments for conjunctivitis, particularly viral conjunctivitis.

SUMMARY

Aspects of the present specification disclose a method of treating an individual with a viral conjunctivitis. The disclosed method comprises administering to an individual in need thereof a pharmaceutical composition comprising a therapeutic effective amount of one or more Ranpirnases and/or a therapeutic effective amount of one or more Amphinase. Such administration reduces a symptom associated with the viral conjunctivitis, thereby treating the individual. Also disclosed is a use of a pharmaceutical composition comprising one or more Ranpirnases and/or one or more Amphinase for treating of a viral conjunctivitis. A viral conjunctivitis disclosed herein includes an epidemic keratoconjunctivitis, a pharyngoconjunctival fever, a nonspecific sporadic follicular conjunctivitis, or a chronic papillary conjunctivitis. A viral conjunctivitis disclosed herein may be caused by a Human adenovirus B, a Human adenovirus D, or a Human adenovirus E.

Other aspects of methods of reducing or suppressing a level of a virus, viral titer, viral replication, protein synthesis and/or tRNA in an individual. The disclosed methods comprises administering to an individual in need thereof a pharmaceutical composition comprising a therapeutic effective amount of one or more Ranpirnases and/or a therapeutic effective amount of one or more Amphinase. Such administration reduces or suppresses a level of a virus, viral titer, viral replication, protein synthesis and/or tRNA. Also disclosed is a use of a pharmaceutical composition comprising one or more Ranpirnases and/or one or more Amphinase for reducing or suppressing a level of a virus, viral titer, viral replication, protein synthesis and/or tRNA in an individual.

Other aspects of a method of reducing or suppressing a level of an inflammation inducing molecule in an individual. The disclosed method comprises administering to an individual in need thereof a pharmaceutical composition comprising a therapeutic effective amount of one or more Ranpirnases and/or a therapeutic effective amount of one or more Amphinase. Such administration reduces or suppresses a level of an inflammation inducing molecule. Also disclosed is a use of a pharmaceutical composition comprising one or more Ranpirnases and/or one or more Amphinase for reducing or suppressing a level of an inflammation inducing molecule. An inflammation inducing molecule disclosed herein includes a substance P, a calcitonin gene-related peptide, a glutamate, or a combination thereof.

Other aspects of a method of reducing or suppressing a level of an inflammation inducing prostaglandin in an individual. The disclosed method comprises administering to an individual in need thereof a pharmaceutical composition comprising a therapeutic effective amount of one or more Ranpirnases and/or a therapeutic effective amount of one or more Amphinase. Such administration reduces or suppresses a level of an inflammation inducing prostaglandin. Also disclosed is a use of a pharmaceutical composition comprising one or more Ranpirnases and/or one or more Amphinase for reducing or suppressing a level of an inflammation inducing prostaglandin. An inflammation inducing prostaglandin includes 15dPGJ2.

Other aspects of a method of stimulating or enhancing a peroxisome proliferator-activated receptor (PPAR) signaling pathway activity in an individual. The disclosed method comprises administering to an individual in need thereof a pharmaceutical composition comprising a therapeutic effective amount of one or more Ranpirnases and/or a therapeutic effective amount of one or more Amphinase. Such administration stimulates or enhances a PPAR signaling pathway activity. Also disclosed is a use of a pharmaceutical composition comprising one or more Ranpirnases and/or one or more Amphinase for stimulating or enhancing a PPAR signaling pathway activity. A PPAR signaling pathway activity includes a PPAR-α signaling pathway activity, a PPAR-γ signaling pathway activity, and a PPAR-δ (also known as PPAR-β) signaling pathway activity Other aspects of a method of promoting the resolving phenotypic change of M1 to M2 in an individual. The disclosed method comprises administering to an individual in need thereof a pharmaceutical composition comprising a therapeutic effective amount of one or more Ranpirnases and/or a therapeutic effective amount of one or more Amphinase. Such administration induces apoptosis of Macrophage M1 cells, promotes differentiation of Macrophage M2 cells or both, thereby promoting the resolving phenotypic change of M1 to M2. Also disclosed is a use of a pharmaceutical composition comprising one or more Ranpirnases and/or one or more Amphinase for promoting the resolving phenotypic change of M1 to M2.

Other aspects of a method of modulating a level of a Th1 cytokine and/or a level of a Th2 cytokine in an individual. The disclosed method comprises administering to an individual in need thereof a pharmaceutical composition comprising a therapeutic effective amount of one or more Ranpirnases and/or a therapeutic effective amount of one or more Amphinase. Such administration reduces the levels of Interferon-gamma (IFNγ), Tumor necrosis factor-alpha (TNF-α), Interleukin-1b (IL-1b), Interleukin-12 (IL-12), or a combination thereof released from a Th1 cell, increases the level of IL-10 released from a Th2 cell, or both, thereby modulating a level of a Th1 cytokine and/or Th2 cytokine. Also disclosed is a use of a pharmaceutical composition comprising one or more Ranpirnases and/or one or more Amphinase for modulating a level of a Th1 cytokine and/or a level of a Th2 cytokine.

Other aspects of a method of reducing or suppressing a NFκB signaling pathway activity in an individual. The disclosed method comprises administering to an individual in need thereof a pharmaceutical composition comprising a therapeutic effective amount of one or more Ranpirnases and/or a therapeutic effective amount of one or more Amphinase. Such administration reduces or suppresses the NFκB signaling pathway activity. Also disclosed is a use of a pharmaceutical composition comprising one or more Ranpirnases and/or one or more Amphinase for reducing or suppressing a NFκB signaling pathway activity.

DETAILED DESCRIPTION

Viruses constitute important pathogens that can infect animals, including humans and plants. Despite their great diversity, all viruses are obligate intracellular parasites, meaning that each is dependent on the host cell and its cellular processes to complete their replicative cycle. As a first step to completing their replicative cycle, a virus needs to invade a host cell. This is achieved by proteins on the surface of the virus interacting with proteins on the surface of the host cell, enabling the virus to become attached to or adsorbed into the cell membrane. Such association triggers a breach in the cell membrane allowing the virus or its genetic contents to be released into the cytoplasm of the host cell. Next, a virus co-opts the replication mechanisms of the infected host cell in order making copies of its genome and packaging these copies into newly synthesized viral particles. Upon completion of the viral replication phase, virus progeny are released from the infected host cell by budding or apoptosis in order to find new host cells to infect.

During infection, both enveloped and non-enveloped viruses induce several global metabolic changes on infected cells including the rearrangement of phospholipids and sialic acid-rich gangliosides in the plasma membrane of the host cell. The increased presence of sialic acid-rich gangliosides and anionic phospholipids leads to an increased electro-negativity of the plasma membrane. For example, in healthy cells, the lipid bilayer of the cell membrane is organized in such a way that anionic phospholipids are located on the intracellular side of the membrane. This anionic phospholipid asymmetry is actively maintained by ATP-dependent transport processes that translocate these phospholipids extracellular side to the intracellular side of the plasma membrane. However, upon viral infection, this translocation process is disrupted resulting in the presence of anionic phospholipid on extracellular side of the plasma membrane. In addition, since this effect is both host-derived and virus-independent, the presence of anionic phospholipids on the extracellular surface of the plasma membrane would be a common feature of any cell infected with a virus. Thus, in general, cells infected with a virus are more negatively charged than are homologous uninfected cells.

Without wishing to be limited to any one mechanism, because a Ranpirnase and/or an Amphinase disclosed herein are strongly cationic molecules, these proteins would have greater electrostatic affinity to the anionic, electro-negativity charged surface of virus-infected cells and consequently would be more avidly internalized by cells infected by a virus. Cells uninfected with virus would be unable to transport a Ranpirnase and/or an Amphinase disclosed herein into its cytoplasm because its plasma membranes lack anionic, electro-negativity charged surfaces. As such, a Ranpirnase and/or an Amphinase disclosed herein interact in a highly preferential way with cells infected with a virus. This high selectivity for virally-infected cells has enabled the investigation of a Ranpirnase and/or an Amphinase disclosed herein for developing treatment for virally-caused diseases and disorders.

Disclosed herein are Ranpirnases and Amphinases, compositions comprising these enzymes and method and uses to treat a viral conjunctivitis, an epidemic keratoconjunctivitis, and/or a pharyngoconjunctival fever, reduce or suppress a level of virus or viral titer, reduce or suppress viral replication, reduce or suppress protein synthesis, reduce or suppress a level of a tRNA, reduce or suppress a level of an inflammation inducing molecule and/or an inflammation inducing prostaglandin, stimulate or enhance a peroxisome proliferator-activated receptor (PPAR) pathway signal, promote the resolving phenotypic change of M1 to M2, modulate Th1 and Th2 cytokines, and/or reduce or suppress a NFκB pathway signal using such Ranpirnases, Amphinases or compositions comprising such Ranpirnases and/or Amphinases. A Ranpirnase and Amphinase disclosed herein are highly specific for adenovirus serotypes are very hydrophilic, which facilitates its potential to get through the ocular barriers to potentially enhance drug uptake to the target tissue.

Viral conjunctivitis has two main attributes that need mitigation, the presence and replication of virus and the host immune response that leads to clinical symptoms. For a successful therapy, addressing only one of these two facets is not enough. A Ranpirnase or Amphinase disclosed herein appear to have both antiviral and immunomodulatory mechanisms of action.

Aspects of the present disclosure comprise, in part, a Ranpirnase. Ranpirnase is an amphibian ribonuclease originally isolated from oocytes and/or early embryos of the *Rana pipiens* (the Northern Leopard frog). Originally called P-30 Protein or P-30, Ranpirnase is a member of the pancreatic ribonuclease (RNase A) protein superfamily. Initially expressed as a precursor polypeptide, Ranpirnase is processed to remove both the precursor peptide portion and the start methionine to produce a basic, lysine-rich, enzyme having a molecular weight of about 12 kD. The N-terminal pyroglutamyl residue is an integral part of Ranpirnase active site and significantly contributing to the catalytic and biological activities of Ranpirnase as well as to its unusually high conformational stability. Another structural feature of Ranpirnase is the C-terminal disulfide bond (87-104) that stabilizes the protein compact structure. This, in turn, makes Ranpirnase highly resistant to endogenous proteases. Another feature of Ranpirnase that makes it resistant to endogenous proteases is the low intracellular binding affinity observed for specific RNase inhibitors, allowing Ranpirnase to remain active inside the cell while the majority of mammalian RNases are inhibited.

Ranpirnase primarily targets rapidly replicating and/or growing cells by binding to cell surface receptors and internalizing into the cytoplasm via AP-2/clathrin-mediated endocytosis. The enzyme is then shuttled to the endoplasmic reticulum where it degrades RNA substrates with a sequence preference for uracil and guanine nucleotides. For example, cleavage site mapping using natural Transfer RNA (tRNA) substrates in vitro revealed predominant cleavage sites at UG and GG residues as well as cleavage at CG sites. Transfer RNA appears to be preferentially targeted as a substrate by Ranpirnase, which leaves messenger RNA (mRNA) and ribosomal RNA (rRNA) undamaged. The degradation of tRNA by Ranpirnase results in the inhibition of protein synthesis.

However, the biological effects of Ranpirnase cannot be explained solely by a decline in protein synthesis suggesting that additional or alternative RNA molecules may be targeted by Ranpirnase. One alternative mechanism has been attributed to the RNA interference pathway and the degradation of miRNAs and/or siRNAs. These small RNAs, similar to tRNAs, are unprotected by proteins and may also be degraded by Ranpirnase. Ranpirnase may also degrade the precursors of small RNAs and thus, generate siRNAs and affect gene expression. Recent findings revealed a new classes of regulatory RNAs (30-40 nt) that may be derived from small non-coding RNAs, especially tRNA, suggesting that Ranpirnase could generate siRNAs directly from its intracellular tRNA substrate.

Ranpirnase has also been shown to possess immunomodulatory mechanisms of action through interference with the nuclear factor kappa-light-chain-enhancer of activated B cells (NFκB) pathway. A small in vitro study showed that Ranpirnase inhibits translocation of NFκB into the nucleus. NFκB, a protein complex that controls transcription of DNA, is of a key master regulator of inflammation in response to proinflammatory stimulation. NFκB is found in almost all animal cells and regulates cellular responses to stimuli such as stress, free radicals, bacterial and/or viral antigens. Further, NFκB plays a key role in regulating the immune response to infection (κ light chains are important components of immunoglobulins). By inhibiting the translocation of NFκB into the nucleus, where it is required in order to enhance inflammation, the inflammatory process will be dampened. In addition, tumor necrosis factor alpha (TNFα) and Interleukin 1-b (IL-1b) are both activate and are activated by NFκB in a positive feedback loop in which genes that are regulated by NFκB also cause the activation of NFκB. Proinflammatory cytokines (including TNFα and IL-1b) attract inflammatory cells to sites of inflammation, enzymes which generate mediators of inflammation, immune receptors, and adhesion molecules that play an important role in the initial recruitment of neutrophils and macrophages to sites of inflammation. Thus, the activation and translocation of NFκB therefore leads to a coordinated increase in the expression of many genes whose products mediate inflammatory and immune responses. This type of positive regulatory loop may amplify and perpetuate local inflammatory responses. As such, the finding that Ranpirnase blocked the proinflammatory effects mediated by NFκB activity suggests that this enzyme could effectively suppress an inflammatory response. It is interesting to note that in both mice and humans with either an acute trauma (mice) or epidemic keratoconjunctivitis (patient that was diagnosed with adenoviral infection), NFκB translocated into the nucleus from the cytoplasm of conjunctival epithelial cells. This is of critical observation as a drug, such as Ranpirnase, that has the ability of block such translocation, has the ability to knock down the inflammatory response to such triggers. No direct studies have been found that evaluate the in vivo immunomodulation effects of Ranpirnase though.

Specific to the antiviral properties of Ranpirnase, a few studies help further understand how Ranpirnase can affect viral production. Ranpirnase has been shown to: 1) inhibit replication of HIV-1 (as an example) by up to 99.9% in the p24 antigen assay at final concentrations that are not cytotoxic; 2) inhibit syncytia formation which often occurs during active viral infections; 3) inhibit early transactivation of viral promoter sequences by tatIII protein; and 4) degrade intracellularly viral RNA, as well as various species of cellular tRNA but not cellular mRNA or rRNA. These findings suggest that extracellularly applied Ranpirnase is capable of entering the interior of infected cells and inhibit viral replication via at least two possible mechanisms: 1) direct degradation of the viral RNA, and 2) indirectly, via degradation of the tRNA. Since RNases are enzymes specializing in ribonucleolytic degradation of respective RNA substrates, it seems highly unlikely that the viral strains will develop resistance to its catalytic activity.

In an embodiment, a Ranpirnase disclosed herein comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26. In aspects of this embodiment, a Ranpirnase disclosed herein has an amino acid identity of, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26. In yet other aspects of this embodiment, a Ranpirnase disclosed herein has an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26.

In other aspects of this embodiment, a Ranpirnase disclosed herein has, e.g., at least 1, 2, 3, 4, 5, 6, 7, 8, 9, 10, 11, 12, 13, 14, or 15 contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26; or at most 1, 2, 3, 4, 5, 6, 7, 8, 9, 10, 11, 12, 13, 14, or 15 contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26. In yet other aspects of this embodiment, a Ranpirnase disclosed herein has, e.g., at least 1, 2, 3, 4, 5, 6, 7, 8, 9, 10, 11, 12, 13, 14, or 15 non-contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26; or at most 1, 2, 3, 4, 5, 6, 7, 8, 9, 10, 11, 12, 13, 14, or 15 non-contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26.

A Ranpirnase disclosed herein can have the N-terminus blocked with pyroglutamic acid (<Glu). In one aspect, the pyroglutamic acid N-terminus block is produced by auto-cyclization of glutamine (Gln). A Ranpirnase disclosed herein can also have the N-terminus blocked with pyrrolidone carboxylic acid. In aspects of this embodiment, a Ranpirnase comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26 has its N-terminus blocked with pyroglutamic acid or pyrrolidone carboxylic acid.

Aspects of the present disclosure comprise, in part, an Amphinase. Another member of the pancreatic RNase A protein superfamily, Amphinase was also isolated from amphibians and is a more basic variant of Ranpirnase. Initially expressed as a precursor polypeptide, Amphinase is processed to remove both the precursor peptide portion and the start methionine to produce an active enzyme having a molecular weight of about 13 kD. Like Ranpirnase, Amphinase primarily targets rapidly replicating and/or growing cells by degrading RNA and at a minimum inhibit protein synthesis.

In an embodiment, an Amphinase disclosed herein comprises SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39. In aspects of this embodiment, an Amphinase disclosed herein has an amino acid identity of, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, to SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39. In yet other aspects of this embodiment, an Amphinase disclosed herein has an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, to SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39.

In other aspects of this embodiment, an Amphinase disclosed herein has, e.g., at least 1, 2, 3, 4, 5, 6, 7, 8, 9, 10, 11, 12, 13, 14, or 15 contiguous amino acid deletions, additions, and/or substitutions relative to SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39; or at most 1, 2, 3, 4, 5, 6, 7, 8, 9, 10, 11, 12, 13, 14, or 15 contiguous amino acid deletions, additions, and/or substitutions relative to SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39. In yet other aspects of this embodiment, an Amphinase disclosed herein has, e.g., at least 1, 2, 3, 4, 5, 6, 7, 8, 9, 10, 11, 12, 13, 14, or 15 non-contiguous amino acid deletions, additions, and/or substitutions relative to SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39; or at most 1, 2, 3, 4, 5, 6, 7, 8, 9, 10, 11, 12, 13, 14, or 15 non-contiguous amino acid deletions, additions, and/or substitutions relative to SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39.

Other Ranpirnase and Amphinase useful in the compositions, methods and uses disclosed herein are described in, e.g., U.S. Pat. No. 5,559,212, U.S. Pat. No. 5,728,805, U.S. Pat. No. 6,239,257, U.S. Pat. No. 6,175,003, U.S. Pat. No. 6,423,515, U.S. Pat. No. 7,229,824, U.S. Pat. No. 7,442,535, U.S. Pat. No. 7,442,536, U.S. Pat. No. 7,473,542, U.S. Pat. No. 7,556,953, U.S. Pat. No. 7,585,655, U.S. Pat. No. 7,763,449, U.S. Pat. No. 7,556,951, U.S. Pat. No. 7,556,952, U.S. Pat. No. 7,585,654, U.S. Pat. No. 8,518,399, U.S. Pat. No. 8,663,964, U.S. Pat. No. 8,808,690, each of which is incorporated by reference in its entirety. Similarly, US Non-Provisional patent application titled "Methods of Treating Viral Infections, Particularly Rabies, Mers-Cov, Influenza, Ebola, Chikungunya, Venezuelan Equine Encephalitis, Canine Parvovirus, Adenovirus, Respiratory Syncytial Virus, Rhinovirus, and Poxvirus in Mammalian Patients", filed Mar. 24, 2015 is also incorporated by reference in its entirety.

In another embodiment, a Ranpirnase and/or Amphinase disclosed herein can be recombinantly engineered to add functional domains without inhibiting the endogenous activity of a Ranpirnase and/or Amphinase disclosed herein. For instance, an Eosinophilic Cationic Protein fragment can be added to a Ranpirnase and/or Amphinase disclosed herein in order to provide or significantly improve bactericidal properties. Such constructs are described in Torrent, et al., "Bactericidal Activity Engineered on Human Pancreatic Ribonuclease and Onconase", Mol. Pharm. 6(2): 531-542 (2009), which is incorporated by reference in its entirety. This could be of significant value if a single therapeutic could treat both bacterial and viral conjunctivitis, while still addressing the common underlying immune response to such stress.

The present specification describes various polypeptide variants where one amino acid is substituted for another, such as, e.g., a Ranpirnase disclosed herein or an Amphinase disclosed herein. A substitution can be assessed by a variety of factors, such as, e.g., the physic properties of the amino acid being substituted (Table 1) or how the original amino acid would tolerate a substitution (Table 2). The selections of which amino acid can be substituted for another amino acid in a polypeptide are known to a person of ordinary skill in the art.

TABLE 1

Amino Acid Properties

| Property | Amino Acids |
|---|---|
| Aliphatic | G, A, I, L, M, P, V |
| Aromatic | F, H, W, Y |
| C-beta branched | I, V, T |
| Hydrophobic | C, F, I, L, M, V, W |
| Small polar | D, N, P |
| Small non-polar | A, C, G, S, T |
| Large polar | E, H, K, Q, R, W, Y |
| Large non-polar | F, I, L, M, V |
| Charged | D, E, H, K, R |
| Uncharged | C, S, T |
| Negative | D, E |
| Positive | H, K, R |
| Acidic | D, E |
| Basic | K, R |
| Amide | N, Q |

TABLE 2

Amino Acid Substitutions

| Amino Acid | Favored Substitution | Neutral Substitutions | Disfavored substitution |
|---|---|---|---|
| A | G, S, T | C, E, I, K, M, L, P, Q, R, V | D, F, H, N, Y, W |
| C | F, S, Y, W | A, H, I, M, L, T, V | D, E, G, K, N, P, Q, R |
| D | E, N | G, H, K, P, Q, R, S, T | A, C, I, L, |
| E | D, K, Q | A, H, N, P, R, S, T | C, F, G, I, L, M, V, W, Y |
| F | M, L, W, Y | C, I, V | A, D, E, G, H, K, N, P, Q, R, S, T |
| G | A, S | D, K, N, P, Q, R | C, E, F, H, I, L, M, T, V, W, Y |
| H | N, Y | C, D, E, K, Q, R, S, T, W | A, F, G, I, L, M, P, V |
| I | V, L, M | A, C, T, F, Y | D, E, G, H, K, N, P, Q, R, S, W |
| K | Q, E, R | A, D, G, H, M, N, P, S, T | C, F, I, L, V, W, Y |
| L | F, I, M, V | A, C, W, Y | D, E, G, H, K, N, P, Q, R, S, T |
| M | F, I, L, V | A, C, R, Q, K, T, W, Y | D, E, G, H, N, P, S |
| N | D, H, S | E, G, K, Q, R, T | A, C, F, H, I, L, M, P, V, W, Y |
| P | — | A, D, E, G, K, Q, R, S, T | C, F, H, I, L, M, N, V, W, Y |
| Q | E, K, R | A, D, G, H, M, N, P, S, T | C, F, I, L, V, W, Y |
| R | K, Q | A, D, E, G, H, M, N, P, S, T | C, F, I, L, V, W, Y |
| S | A, N, T | C, D, E, G, H, K, P, Q, R, T | F, I, L, M, V, W, Y |
| T | S | A, C, D, E, H, I, K, M, N, P, Q, R, V | F, G, L, W, Y |
| V | I, L, M | A, C, F, T, Y | D, E, G, H, K, N, P, Q, R, S, W |
| W | F, Y | H, L, M | A, C, D, E, G, I, K, N, P, Q, R, S, T, V |
| Y | F, H, W | C, I, L, M, V | A, D, E, G, K, N, P, Q, R, S, T |

Matthew J. Betts and Robert, B. Russell, Amino Acid Properties and Consequences of Substitutions, pp. 289-316, In Bioinformatics for Geneticists, (eds Michael R. Barnes, Ian C. Gray, Wiley, 2003).

In aspects of this embodiment, a hydrophobic amino acid at one particular position in a Ranpirnase and/or Amphinase disclosed herein can be substituted with another hydrophobic amino acid. Examples of hydrophobic amino acids include, e.g., C, F, I, L, M, V and W. In another aspect of this embodiment, an aliphatic amino acid at one particular position in a Ranpirnase and/or Amphinase disclosed herein can be substituted with another aliphatic amino acid. Examples of aliphatic amino acids include, e.g., A, I, L, P, and V. In yet another aspect of this embodiment, an aromatic amino acid at one particular position in a Ranpirnase and/or Amphinase disclosed herein can be substituted with another aromatic amino acid. Examples of aromatic amino acids include, e.g., F, H, W and Y. In still another aspect of this embodiment, a stacking amino acid at one particular position in a Ranpirnase and/or Amphinase disclosed herein can be substituted with another stacking amino acid. Examples of stacking amino acids include, e.g., F, H, W and Y. In a further aspect of this embodiment, a polar amino acid at one particular position in a Ranpirnase and/or Amphinase disclosed herein can be substituted with another polar amino acid. Examples of polar amino acids include, e.g., D, E, K, N, Q, and R. In a further aspect of this embodiment, a less polar or indifferent amino acid at one particular position in a Ranpirnase and/or Amphinase disclosed herein can be substituted with another less polar or indifferent amino acid. Examples of less polar or indifferent amino acids include, e.g., A, H, G, P, S, T, and Y. In a yet further aspect of this embodiment, a positive charged amino acid at one particular position in a Ranpirnase and/or Amphinase disclosed herein can be substituted with another positive charged amino acid. Examples of positive charged amino acids include, e.g., K, R, and H. In a still further aspect of this embodiment, a negative charged amino acid at one particular position in a Ranpirnase and/or Amphinase disclosed herein can be substituted with another negative charged amino acid. Examples of negative charged amino acids include, e.g., D and E. In another aspect of this embodiment, a small amino acid at one particular position in a Ranpirnase and/or Amphinase disclosed herein can be substituted with another small amino acid. Examples of small amino acids include, e.g., A, D, G, N, P, S, and T. In yet another aspect of this embodiment, a C-beta branching amino acid at one particular position in a Ranpirnase and/or Amphinase disclosed herein can be substituted with another C-beta branching amino acid. Examples of C-beta branching amino acids include, e.g., I, T and V.

In an embodiment, a Ranpirnase and/or Amphinase disclosed herein has an anti-viral activity capable of reducing or suppressing a level of virus or viral titer. In aspects of this embodiment, a Ranpirnase and/or Amphinase disclosed herein has an anti-viral activity capable of reducing or suppressing a level of virus or viral titer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a Ranpirnase and/or Amphinase disclosed herein has an anti-viral activity capable of reducing or suppressing a level of virus or viral titer in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a Ranpirnase and/or Amphinase disclosed herein has an anti-viral activity capable of reducing or suppressing viral replication. In aspects of this embodiment, a Ranpirnase and/or Amphinase disclosed herein has an anti-viral activity capable of reducing or suppressing viral replication by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a Ranpirnase and/or Amphinase disclosed herein has an anti-viral activity capable of reducing or suppressing viral replication in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a Ranpirnase and/or Amphinase disclosed herein has an anti-viral activity capable of reducing or suppressing protein synthesis in one or more cells. In aspects of this embodiment, a Ranpirnase and/or Amphinase disclosed herein has an anti-viral activity capable of reducing or suppressing protein synthesis in one or more cells by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a Ranpirnase and/or Amphinase disclosed herein has an anti-viral activity capable of reducing or suppressing protein synthesis in one or more cells in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a Ranpirnase and/or Amphinase disclosed herein has an anti-viral activity capable of reducing or suppressing a level of tRNA in one or more cells. In aspects of this embodiment, a Ranpirnase and/or Amphinase disclosed herein has an anti-viral activity capable reducing or suppressing a level of tRNA in one or more cells by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a Ranpirnase and/or Amphinase disclosed herein has an anti-viral activity capable reducing or suppressing a level of tRNA in one or more cells in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, a Ranpirnase and/or Amphinase disclosed herein has an anti-inflammatory activity capable of reducing the levels of an inflammation inducing molecule. In an aspect of this embodiment, a Ranpirnase and/or Amphinase disclosed herein has an anti-inflammatory activity capable of reducing the levels of substance P (SP), calcitonin gene-related peptide (CGRP), glutamate, or a combination thereof. In other aspects of this embodiment, a Ranpirnase and/or Amphinase disclosed herein has an anti-inflammatory activity capable of reducing the levels of SP, CGRP, glutamate, or a combination thereof released from a sensory neuron by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a Ranpirnase and/or Amphinase disclosed herein has an anti-inflammatory activity capable of reducing the levels of SP, CGRP, glutamate, or a combination thereof released from a sensory neuron in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

Prostaglandins mediate a local inflammatory response and are involved in all inflammatory functions through action on prostaglandin receptors and mediate inflammatory signaling including chemotaxis (macrophages, neutrophils and eosinophils), vasodilation and algesia. However, the PG-mediated inflammatory response is self-limiting (resolving). The principle resolution factor is a prostaglandin called 15dPGJ2, which is an endogenous agonist of peroxisome proliferator-activator receptor gamma (PPAR-γ) signaling. PPARγ signaling pathway 1) induces apoptosis of Macrophage M1 cells, thereby reducing the levels of Th1 pro-inflammatory cytokines and 2) promotes differentiation of monocytes into Macrophage M2 cells. Macrophage M2 cells produce and release Th2 anti-inflammatory cytokines.

In an embodiment, a Ranpirnase and/or Amphinase disclosed herein has an anti-inflammatory activity capable of reducing the levels of an inflammation inducing prostaglandin. In other aspects of this embodiment, a Ranpirnase and/or Amphinase disclosed herein has an anti-inflammatory activity capable of reducing the levels of an inflammation inducing prostaglandin released from a sensory neuron by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a Ranpirnase and/or Amphinase disclosed herein has an anti-inflammatory activity capable of reducing the levels of an inflammation inducing prostaglandin released from a sensory neuron in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a Ranpirnase and/or Amphinase disclosed herein has an anti-inflammatory activity substantially similar to 15dPGJ2. In aspects of this embodiment, a Ranpirnase and/or Amphinase disclosed herein an anti-inflammatory activity that is, e.g., at least 5%, at least 15%, at least 25%, at least 50%, at least 55%, at least 60%, at least 65%, at least 70%, at least 75%, at least 80%, at least 85%, at least 90% or at least 95% of the activity observed for 15dPGJ2. In other aspects of this embodiment, a Ranpirnase and/or Amphinase disclosed herein an anti-inflammatory activity that is in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50% of the activity observed for 15dPGJ2.

The peroxisome proliferator-activated receptors (PPARs) are a group of nuclear receptor proteins that function as transcription factors regulating the expression of genes. All PPARs are known to heterodimerize with the retinoid X receptor (RXR) and bind to specific regions on the DNA of target genes called peroxisome proliferator hormone response elements (PPREs). PPARs play essential roles in the regulation of cellular differentiation, development, and metabolism (carbohydrate, lipid, protein), and tumorigenesis of higher organisms. The family comprises three members, PPAR-α, PPAR-γ, and PPAR-δ (also known as PPAR-β). PPAR-α is expressed in liver, kidney, heart, muscle, adipose tissue, as well as other tissues. PPAR-δ is expressed in many tissues but markedly in brain, adipose tissue, and skin. PPAR-γ comprises three alternatively-spliced forms, each with a different expression pattern. PPAR-γ1 is expressed in virtually all tissues, including heart, muscle, colon, kidney, pancreas, and spleen. PPAR-γ2 is expressed mainly in adipose tissue. PPAR-γ3 is expressed in macrophages, large intestine, and white adipose tissue. Endogenous ligands for the PPARs include free fatty acids and eicosanoids. PPAR-γ is activated by PGJ2 (a prostaglandin), whereas PPAR-α is activated by leukotriene B4.

In an embodiment, a Ranpirnase and/or Amphinase disclosed herein has an anti-inflammatory activity capable of stimulating or enhancing activity from all PPAR signaling pathways. In other embodiments, a Ranpirnase and/or Amphinase disclosed herein has an anti-inflammatory activity capable of stimulating or enhancing activity of one or two of the PPAR signaling pathways.

In another embodiment, a Ranpirnase and/or Amphinase disclosed herein has an anti-inflammatory activity capable of stimulating or enhancing a PPAR-α signaling pathway activity. In aspects of this embodiment, a Ranpirnase and/or Amphinase disclosed herein stimulates or enhances a PPAR-α signaling pathway activity by, e.g., at least 5%, at least 15%, at least 25%, at least 50%, at least 60%, at least 70%, at least 80%, or at least 90%. In other aspects of this embodiment, a Ranpirnase and/or Amphinase disclosed herein stimulates or enhances a PPAR-α signaling pathway activity in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50%.

In another embodiment, a Ranpirnase and/or Amphinase disclosed herein has an anti-inflammatory activity capable of stimulating or enhancing a PPAR-δ signaling pathway activity. In aspects of this embodiment, a Ranpirnase and/or Amphinase disclosed herein stimulates or enhances a PPAR-δ signaling pathway activity by, e.g., at least 5%, at least 15%, at least 25%, at least 50%, at least 60%, at least 70%, at least 80%, or at least 90%. In other aspects of this embodiment, a Ranpirnase and/or Amphinase disclosed herein stimulates or enhances a PPAR-δ signaling pathway activity in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50%.

In another embodiment, a Ranpirnase and/or Amphinase disclosed herein has an anti-inflammatory activity capable of stimulating or enhancing a PPARγ signaling pathway activity. In aspects of this embodiment, a Ranpirnase and/or Amphinase disclosed herein stimulates or enhances a PPARγ signaling pathway activity by, e.g., at least 5%, at least 15%, at least 25%, at least 50%, at least 60%, at least 70%, at least 80%, or at least 90%. In other aspects of this embodiment, a Ranpirnase and/or Amphinase disclosed herein stimulates or enhances a PPARγ signaling pathway activity in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50%.

Macrophages are activated and polarized into distinct phenotypes expressing unique cell surface molecules and secreting discrete sets of cytokines and chemokines. The classical M1 phenotype supports pro-inflammatory Th1 responses driven by cytokines such as, e.g., Interleukin-6 (IL-6), IL-12 and IL-23, while the alternate M2 phenotype is generally supportive of anti-inflammatory processes driven by IL-10. M2 cells can be further classified into subsets, M2a, M2b, and M2c, based on the type of stimulation and the subsequent expression of surface molecules and cytokines.

In yet another embodiment, a Ranpirnase and/or Amphinase disclosed herein has an anti-inflammatory activity capable of promoting the resolving phenotypic change of M1 to M2. In an aspect of this embodiment, a Ranpirnase and/or Amphinase disclosed herein has an anti-inflammatory activity capable of inducing apoptosis of Macrophage M1 cells. In another aspect of this embodiment, a Ranpirnase and/or Amphinase disclosed herein has an anti-inflammatory activity capable of promoting differentiation of Macrophage M2 cells. In yet another aspect of this embodiment, a Ranpirnase and/or Amphinase disclosed herein has an anti-inflammatory activity capable of inducing apoptosis of Macrophage M1 cells and promoting differentiation of Macrophage M2 cells.

In still another embodiment, a Ranpirnase and/or Amphinase disclosed herein has an anti-inflammatory activity capable of modulating the levels of a Th1 cytokine and/or Th2 cytokine. In an aspect of this embodiment, a Ranpirnase and/or Amphinase disclosed herein has an anti-inflammatory activity capable of reducing a level of Interferon-gamma (IFNγ), Tumor necrosis factor-alpha (TNF-α), Interleukin-1b (IL-1b), Interleukin-12 (IL-12), or a combination thereof released from a Th1 cell. In other aspects of this embodiment, a Ranpirnase and/or Amphinase disclosed herein has an anti-inflammatory activity capable of reducing a level of IFNγ, TNF-α, IL-1b, IL-12, or a combination thereof released from a Th1 cell by, e.g., at least 10%, at least 20%, at least 30%, at least 40%, at least 50%, at least 60%, at least 70%, at least 80%, or at least 90%. In yet other aspects of this embodiment, a Ranpirnase and/or Amphinase disclosed herein has an anti-inflammatory activity capable of reducing a level of IFNγ, TNF-α, IL-1b, IL-12, or a combination thereof released from a Th1 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another aspect of this embodiment, a Ranpirnase and/or Amphinase disclosed herein has an anti-inflammatory activity capable of increasing a level of IL-10 released from a Th2 cell. In other aspects of this embodiment, a Ranpirnase and/or Amphinase disclosed herein has an anti-inflammatory activity capable of increasing a level of IL-10 released from a Th2 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a Ranpirnase and/or Amphinase disclosed herein has an anti-inflammatory activity capable of increasing a level of IL-10 released from a Th2 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another aspect of this embodiment, a Ranpirnase and/or Amphinase disclosed herein has an anti-inflammatory activity capable of reducing a level of IFNγ, TNF-α, IL-1b, IL-12, or a combination thereof released from a Th1 cell and increasing a level of IL-10 released from a Th2 cell. In other aspects of this embodiment, a Ranpirnase and/or Amphinase disclosed herein has an anti-inflammatory activity capable of reducing a level of IFNγ, TNF-α, IL-1b, IL-12, or a combination thereof released from a Th1 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%, and capable of increasing a level of IL-10 released from a Th2 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a Ranpirnase and/or Amphinase disclosed herein has an anti-inflammatory activity capable of reducing a level of IFNγ, TNF-α, IL-1b, IL-12, or a combination thereof released from a Th1 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%, and capable of increasing a level of IL-10 released from a Th2 cell in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a Ranpirnase and/or Amphinase disclosed herein has an anti-inflammatory activity capable of reducing of suppressing a NFκB signaling pathway activity. In aspects of this embodiment, a Ranpirnase and/or Amphinase disclosed herein has an anti-inflammatory activity capable of reducing or suppressing a NFκB signaling pathway activity by, e.g., at least 10%, at least 20%, at least 30%, at least 40%, at least 50%, at least 60%, at least 70%, at least 80%, or at least 90%. In yet other aspects of this embodiment, a Ranpirnase and/or Amphinase disclosed herein has an anti-inflammatory activity capable of reducing of suppressing a NFκB signaling pathway activity in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

Aspects of the present specification disclose, in part, a composition. A composition disclosed herein is generally administered as a pharmaceutical acceptable composition. As used herein, the term "pharmaceutically acceptable" refers any molecular entity or composition that does not produce an adverse, allergic or other untoward or unwanted reaction when administered to an individual. As used herein, the term "pharmaceutically acceptable composition" is synonymous with "pharmaceutical composition" and means a therapeutically effective concentration of an active ingredient, such as, e.g., any one of the Ranpirnase and/or Amphinase disclosed herein. A pharmaceutical composition disclosed herein is useful for medical and veterinary applications. A pharmaceutical composition may be administered to an individual alone, or in combination with other supplementary active ingredients, agents, drugs or hormones.

Aspects of the present disclosure comprise, in part, a pharmaceutical composition. A pharmaceutical composition disclosed herein comprises one or more Ranpirnase disclosed herein and/or one or more Amphinase disclosed herein. A pharmaceutical composition comprising one or more Ranpirnase disclosed herein and/or one or more Amphinase disclosed herein, when administered to an individual, stimulates an anti-inflammatory response against the one or more viral strains causing a viral conjunctivitis.

In another aspect of this embodiment, a pharmaceutical composition is a medicament for the treatment of a viral conjunctivitis disclosed herein. In aspects of this embodiment, a one or more Ranpirnase disclosed herein and/or one or more Amphinase disclosed herein is used to manufacture a medicament for the treatment of a viral conjunctivitis disclosed herein. In aspects of this embodiment, use of a Ranpirnase and/or Amphinase disclosed herein is in an amount sufficient to treats a viral conjunctivitis disclosed herein by reducing one or more physiological conditions or symptom associated with a viral conjunctivitis disclosed herein.

In one embodiment, a pharmaceutical composition disclosed herein comprises a single Ranpirnase and/or Amphinase disclosed herein. In one embodiment, a pharmaceutical composition disclosed herein comprises a plurality of Ranpirnases and/or Amphinases disclosed herein. In aspects of this embodiment, a pharmaceutical composition disclosed herein comprises, e.g., 1, 2, 3, 4, 5, 6, 7, 8, 9, 10, 11, 12, 13, 14, or 15 Ranpirnases and/or Amphinases disclosed herein. In other aspects of this embodiment, a pharmaceutical composition disclosed herein comprises, e.g., at least 1, at least 2, at least 3, at least 4, at least 5, at least 6, at least 7, at least 8, at least 9, at least 10, at least 11, at least 12, at least 13, at least 14, or at least Ranpirnases and/or Amphinases disclosed herein. In yet other aspects of this embodiment, a pharmaceutical composition disclosed herein comprises, e.g., at most 1, at most 2, at most 3, at most 4, at most 5, at most 6, at most 7, at most 8, at most 9, at most 10, at most 11, at most 12, at most 13, at most 14, or at most Ranpirnases and/or Amphinases disclosed herein. In still other aspects of this embodiment, a pharmaceutical composition disclosed herein comprises, e.g., 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 3 to 4, 3 to 5, 3 to 6, 3 to 7, 3 to 8, 3 to 9, 3 to 10, 3 to 11, 3 to 12, 3 to 13, 3 to 14, 3 to 15, 4 to 5, 4 to 6, 4 to 7, 4 to 8, 4 to 9, 4 to 10, 4 to 11, 4 to 12, 4 to 13, 4 to 14, 4 to 15, 5 to 6, 5 to 7, 5 to 8, 5 to 9, 5 to 10, 5 to 11, 5 to 12, 5 to 13, 5 to 14, 5 to 15, 6 to 7, 6 to 8, 6 to 9, 6 to 10, 6 to 11, 6 to 12, 6 to 13, 6 to 14, 6 to 15, 7 to 8, 7 to 9, 7 to 10, 7 to 11, 7 to 12, 7 to 13, 7 to 14, 7 to 15, 8 to 9, 8 to 10, 8 to 11, 8 to 12, 8 to 13, 8 to 14, 8 to 15, 9 to 10, 9 to 11, 9 to 12, 9 to 13, 9 to 14, 9 to 15, 10 to 11, 10 to 12, 10 to 13, 10 to 14, 10 to 15, 11 to 12, 11 to 13, 11 to 14, 11 to 15, 12 to 13, 12 to 14, 12 to 15, 13 to 14, 13 to 15, or 14-15 Ranpirnases and/or Amphinases disclosed herein.

The amount of a Ranpirnase and/or Amphinase disclosed herein included in a pharmaceutical composition is an amount sufficient to elicit an appropriate anti-inflammatory response in the individual. Typically, this amount is also one that does not cause significant adverse side effects. Such amount will vary depending on which specific Ranpirnase and/or Amphinase is administered. An optimal amount for a particular pharmaceutical composition can be ascertained by standard studies involving observation of proinflammatory cytokine titers, anti-inflammatory cytokine titers, prostaglandin titers, reduction of one or more symptoms associated with a viral conjunctivitis, and other responses in individuals. A primary pharmaceutical composition course may include 1, 2, 3 or 4 doses of a pharmaceutical composition, given at intervals optimal for providing an anti-inflammatory response.

Generally, an effective and safe amount of a Ranpirnase and/or Amphinase disclosed herein included in a pharmaceutical composition varies from about 1 fg to 3,000 mg. In aspects of this embodiment, an amount of a Ranpirnase and/or Amphinase disclosed herein included in a pharmaceutical composition may be, e.g., about 1 fg, about 2 fg, about 3 fg, about 4 fg, about 5 fg, about 6 fg, about 7 fg, about 8 fg, about 9 fg, about 10 fg, about 15 fg, about 20 fg, about 25 fg, about 30 fg, about 35 fg, about 40 fg, about 45 fg, about 50 fg, about 55 fg, about 60 fg, about 65 fg, about 70 fg, about 75 fg, about 80 fg, about 85 fg, about 90 fg, about 95 fg, about 100 fg, about 110 fg, about 120 fg, about 130 fg, about 140 fg, about 150 fg, about 160 fg, about 170 fg, about 180 fg, about 190 fg, about 200 fg, about 210 fg, about 220 fg, about 230 fg, about 240 fg, about 250 fg, 260 fg, about 270 fg, about 280 fg, about 290 fg, about 300 fg, about 310 fg, about 320 fg, about 330 fg, about 340 fg, about 350 fg, 360 fg, about 370 fg, about 380 fg, about 390 fg, about 400 fg, about 410 fg, about 420 fg, about 430 fg, about 440 fg, about 450 fg, 460 fg, about 470 fg, about 480 fg, about 490 fg, about 500 fg, about 510 fg, about 520 fg, about 530 fg, about 540 fg, about 550 fg, 560 fg, about 570 fg, about 580 fg, about 590 fg, about 600 fg, about 610 fg, about 620 fg, about 630 fg, about 640 fg, about 650 fg, 660 fg, about 670 fg, about 680 fg, about 690 fg, about 700 fg, about 710 fg, about 720 fg, about 730 fg, about 740 fg, about 750 fg, 760 fg, about 770 fg, about 780 fg, about 790 fg, about 800 fg, about 810 fg, about 820 fg, about 830 fg, about 840 fg, about 850 fg, 860 fg, about 870 fg, about 880 fg, about 890 fg, about 900 fg, about 910 fg, about 920 fg, about 930 fg, about 940 fg, about 950 fg, 960 fg, about 970 fg, about 980 fg, about 990 fg, or about 1,000 fg.

In other aspects of this embodiment, an amount of a Ranpirnase and/or Amphinase disclosed herein included in a pharmaceutical composition may be, e.g., at least 1 fg, at least 2 fg, at least 3 fg, at least 4 fg, at least 5 fg, at least 6 fg, at least 7 fg, at least 8 fg, at least 9 fg, at least 10 fg, at least 15 fg, at least 20 fg, at least 25 fg, at least 30 fg, at least 35 fg, at least 40 fg, at least 45 fg, at least 50 fg, at least 55 fg, at least 60 fg, at least 65 fg, at least 70 fg, at least 75 fg, at least 80 fg, at least 85 fg, at least 90 fg, at least 95 fg, at least 100 fg, at least 110 fg, at least 120 fg, at least 130 fg, at least 140 fg, at least 150 fg, at least 160 fg, at least 170 fg, at least 180 fg, at least 190 fg, at least 200 fg, at least 210 fg, at least 220 fg, at least 230 fg, at least 240 fg, at least 250 fg, 260 fg, at least 270 fg, at least 280 fg, at least 290 fg, at least 300 fg, at least 310 fg, at least 320 fg, at least 330 fg, at least 340 fg, at least 350 fg, 360 fg, at least 370 fg, at least 380 fg, at least 390 fg, at least 400 fg, at least 410 fg, at least 420 fg, at least 430 fg, at least 440 fg, at least 450 fg, 460 fg, at least 470 fg, at least 480 fg, at least 490 fg, at least 500 fg, at least 510 fg, at least 520 fg, at least 530 fg, at least 540 fg, at least 550 fg, 560 fg, at least 570 fg, at least 580 fg, at least 590 fg, at least 600 fg, at least 610 fg, at least 620 fg, at least 630 fg, at least 640 fg, at least 650 fg, 660 fg, at least 670 fg, at least 680 fg, at least 690 fg, at least 700 fg, at least 710 fg, at least 720 fg, at least 730 fg, at least 740 fg, at least 750 fg, 760 fg, at least 770 fg, at least 780 fg, at least 790 fg, at least 800 fg, at least 810 fg, at least 820 fg, at least 830 fg, at least 840 fg, at least 850 fg, 860 fg, at least 870 fg, at least 880 fg, at least 890 fg, at least 900 fg, at least 910 fg, at least 920 fg, at least 930 fg, at least 940 fg, at least 950 fg, 960 fg, at least 970 fg, at least 980 fg, at least 990 fg, or at least 1,000 fg.

In yet other aspects of this embodiment, an amount of a Ranpirnase and/or Amphinase disclosed herein included in a pharmaceutical composition may be, e.g., at most 1 fg, at most 2 fg, at most 3 fg, at most 4 fg, at most 5 fg, at most 6 fg, at most 7 fg, at most 8 fg, at most 9 fg, at most 10 fg, at most 15 fg, at most 20 fg, at most 25 fg, at most 30 fg, at most 35 fg, at most 40 fg, at most 45 fg, at most 50 fg, at most 55 fg, at most 60 fg, at most 65 fg, at most 70 fg, at most 75 fg, at most 80 fg, at most 85 fg, at most 90 fg, at most 95 fg, at most 100 fg, at most 110 fg, at most 120 fg, at most 130 fg, at most 140 fg, at most 150 fg, at most 160 fg, at most 170 fg, at most 180 fg, at most 190 fg, at most 200 fg, at most 210 fg, at most 220 fg, at most 230 fg, at most 240 fg, at most 250 fg, 260 fg, at most 270 fg, at most 280 fg, at most 290 fg, at most 300 fg, at most 310 fg, at most 320 fg, at most 330 fg, at most 340 fg, at most 350 fg, 360 fg, at most 370 fg, at most 380 fg, at most 390 fg, at most 400 fg, at most 410 fg, at most 420 fg, at most 430 fg, at most 440 fg, at most 450 fg, 460 fg, at most 470 fg, at most 480 fg, at most 490 fg, at most 500 fg, at most 510 fg, at most 520 fg, at most 530 fg, at most 540 fg, at most 550 fg, 560 fg, at most 570 fg, at most 580 fg, at most 590 fg, at most 600 fg, at most 610 fg, at most 620 fg, at most 630 fg, at most 640 fg, at most 650 fg, 660 fg, at most 670 fg, at most 680 fg, at most 690 fg, at most 700 fg, at most 710 fg, at most 720 fg, at most 730 fg, at most 740 fg, at most 750 fg, 760 fg, at most 770 fg, at most 780 fg, at most 790 fg, at most 800 fg, at most 810 fg, at most 820 fg, at most 830 fg, at most 840 fg, at most 850 fg, 860 fg, at most 870 fg, at most 880 fg, at most 890 fg, at most 900 fg, at most 910 fg, at most 920 fg, at most 930 fg, at most 940 fg, at most 950 fg, 960 fg, at most 970 fg, at most 980 fg, at most 990 fg, or at most 1,000 fg.

In still other aspects of this embodiment, an amount of a Ranpirnase and/or Amphinase disclosed herein included in a pharmaceutical composition may be in the range of, e.g., about 1 fg to about 10 fg, about 1 fg to about 20 fg, about 1 fg to about 30 fg, about 1 fg to about 40 fg, about 1 fg to about 50 fg, about 1 fg to about 60 fg, about 1 fg to about 70 fg, about 1 fg to about 80 fg, about 1 fg to about 90 fg, about 1 fg to about 100 fg, about 1 fg to about 110 fg, about 1 fg to about 120 fg, about 1 fg to about 130 fg, about 1 fg to about 140 fg, about 1 fg to about 150 fg, about 5 fg to about 10 fg, about 5 fg to about 20 fg, about 5 fg to about 30 fg, about 5 fg to about 40 fg, about 5 fg to about 50 fg, about 5 fg to about 60 fg, about 5 fg to about 70 fg, about 5 fg to about 80 fg, about 5 fg to about 90 fg, about 5 fg to about 100 fg, about 5 fg to about 110 fg, about 5 fg to about 120 fg, about 5 fg to about 130 fg, about 5 fg to about 140 fg, about 5 fg to about 150 fg, about 10 fg to about 20 fg, about 10 fg to about 30 fg, about 10 fg to about 40 fg, about 10 fg to about 50 fg, about 10 fg to about 60 fg, about 10 fg to about 70 fg, about 10 fg to about 80 fg, about 10 fg to about 90 fg, about 10 fg to about 100 fg, about 10 fg to about 110 fg, about 10 fg to about 120 fg, about 10 fg to about 130 fg, about 10 fg to about 140 fg, about 10 fg to about 150 fg, about 10 fg to about 175 fg, about 10 fg to about 200 fg, about 10 fg to about 225 fg, about 10 fg to about 250 fg, about 25 fg to about 50 fg, about 25 fg to about 75 fg, about 25 fg to about 100 fg, about 25 fg to about 125 fg, about 25 fg to about 150 fg, about 25 fg to about 175 fg, about 25 fg to about 200 fg, about 25 fg to about 225 fg, about 25 fg to about 250 fg, about 50 fg to about 75 fg, about 50 fg to about 100 fg, about 50 fg to about 125 fg, about 50 fg to about 150 fg, about 50 fg to about 175 fg, about 50 fg to about 200 fg, about 50 fg to about 225 fg, about 50 fg to about 250 fg, about 75 fg to about 100 fg, about 75 fg to about 125 fg, about 75 fg to about 150 fg, about 75 fg to about 175 fg, about 75 fg to about 200 fg, about 75 fg to about 225 fg, or about 75 fg to about 250 fg.

In still other aspects of this embodiment, an amount of a Ranpirnase and/or Amphinase disclosed herein included in a pharmaceutical composition may be in the range of, e.g., about 100 fg to about 125 fg, about 100 fg to about 150 fg, about 100 fg to about 175 fg, about 100 fg to about 200 fg, about 100 fg to about 225 fg, about 100 fg to about 250 fg, about 100 fg to about 275 fg, about 100 fg to about 300 fg, about 100 fg to about 325 fg, about 100 fg to about 350 fg, about 100 fg to about 375 fg, about 100 fg to about 400 fg, about 100 fg to about 425 fg, about 100 fg to about 450 fg, about 100 fg to about 475 fg, about 100 fg to about 500 fg, about 100 fg to about 525 fg, about 100 fg to about 550 fg, about 100 fg to about 575 fg, about 100 fg to about 600 fg, about 125 fg to about 150 fg, about 125 fg to about 175 fg, about 125 fg to about 200 fg, about 125 fg to about 225 fg, about 125 fg to about 250 fg, about 125 fg to about 275 fg, about 125 fg to about 300 fg, about 125 fg to about 325 fg, about 125 fg to about 350 fg, about 125 fg to about 375 fg, about 125 fg to about 400 fg, about 125 fg to about 425 fg, about 125 fg to about 450 fg, about 125 fg to about 475 fg, about 125 fg to about 500 fg, about 125 fg to about 525 fg, about 125 fg to about 550 fg, about 125 fg to about 575 fg, about 125 fg to about 600 fg, about 150 fg to about 175 fg, about 150 fg to about 200 fg, about 150 fg to about 225 fg, about 150 fg to about 250 fg, about 150 fg to about 275 fg, about 150 fg to about 300 fg, about 150 fg to about 325 fg, about 150 fg to about 350 fg, about 150 fg to about 375 fg, about 150 fg to about 400 fg, about 150 fg to about 425 fg, about 150 fg to about 450 fg, about 150 fg to about 475 fg, about 150 fg to about 500 fg, about 150 fg to about 525 fg, about 150 fg to about 550 fg, about 150 fg to about 575 fg, about 150 fg to about 600 fg, about 200 fg to about 225 fg, about 200 fg to about 250 fg, about 200 fg to about 275 fg, about 200 fg to about 300 fg, about 200 fg to about 325 fg, about 200 fg to about 350 fg, about 200 fg to about 375 fg, about 200 fg to about 400 fg, about 200 fg to about 425 fg, about 200 fg to about 450 fg, about 200 fg to about 475 fg, about 200 fg to about 500 fg, about 200 fg to about 525 fg, about 200 fg to about 550 fg, about 200 fg to about 575 fg, about 200 fg to about 600 fg, about 200 fg to about 625 fg, about 200 fg to about 650 fg, about 200 fg to about 675 fg, about 200 fg to about 700 fg, about 200 fg to about 725 fg, about 200 fg to about 750 fg, about 200 fg to about 775 fg, about 200 fg to about 800 fg, about 200 fg to about 825 fg, about 200 fg to about 850 fg, about 200 fg to about 875 fg, about 200 fg to about 900 fg, about 200 fg to about 925 fg, about 200 fg to about 950 fg, about 200 fg to about 975 fg, about 200 fg to about 1,000 fg.

In still other aspects of this embodiment, an amount of a Ranpirnase and/or Amphinase disclosed herein included in a pharmaceutical composition may be in the range of, e.g., about 250 fg to about 275 fg, about 250 fg to about 300 fg, about 250 fg to about 325 fg, about 250 fg to about 350 fg, about 250 fg to about 375 fg, about 250 fg to about 400 fg, about 250 fg to about 425 fg, about 250 fg to about 450 fg, about 250 fg to about 475 fg, about 250 fg to about 500 fg, about 250 fg to about 525 fg, about 250 fg to about 550 fg, about 250 fg to about 575 fg, about 250 fg to about 600 fg, about 250 fg to about 625 fg, about 250 fg to about 650 fg, about 250 fg to about 675 fg, about 250 fg to about 700 fg, about 250 fg to about 725 fg, about 250 fg to about 750 fg, about 250 fg to about 775 fg, about 250 fg to about 800 fg, about 250 fg to about 825 fg, about 250 fg to about 850 fg, about 250 fg to about 875 fg, about 250 fg to about 900 fg, about 250 fg to about 925 fg, about 250 fg to about 950 fg, about 250 fg to about 975 fg, about 250 fg to about 1,000 fg, about 300 fg to about 325 fg, about 300 fg to about 350 fg, about 300 fg to about 375 fg, about 300 fg to about 400 fg, about 300 fg to about 425 fg, about 300 fg to about 450 fg, about 300 fg to about 475 fg, about 300 fg to about 500 fg, about 300 fg to about 525 fg, about 300 fg to about 550 fg, about 300 fg to about 575 fg, about 300 fg to about 600 fg, about 300 fg to about 625 fg, about 300 fg to about 650 fg, about 300 fg to about 675 fg, about 300 fg to about 700 fg, about 300 fg to about 725 fg, about 300 fg to about 750 fg, about 300 fg to about 775 fg, about 300 fg to about 800 fg, about 300 fg to about 825 fg, about 300 fg to about 850 fg, about 300 fg to about 875 fg, about 300 fg to about 900 fg, about 300 fg to about 925 fg, about 300 fg to about 950 fg, about 300 fg to about 975 fg, about 300 fg to about 1,000 fg, about 400 fg to about 425 fg, about 400 fg to about 450 fg, about 400 fg to about 475 fg, about 400 fg to about 500 fg, about 400 fg to about 525 fg, about 400 fg to about 550 fg, about 400 fg to about 575 fg, about 400 fg to about 600 fg, about 400 fg to about 625 fg, about 400 fg to about 650 fg, about 400 fg to about 675 fg, about 400 fg to about 700 fg, about 400 fg to about 725 fg, about 400 fg to about 750 fg, about 400 fg to about 775 fg, about 400 fg to about 800 fg, about 400 fg to about 825 fg, about 400 fg to about 850 fg, about 400 fg to about 875 fg, about 400 fg to about 900 fg, about 400 fg to about 925 fg, about 400 fg to about 950 fg, about 400 fg to about 975 fg, or about 400 fg to about 1,000 fg.

In still other aspects of this embodiment, an amount of a Ranpirnase and/or Amphinase disclosed herein included in a pharmaceutical composition may be in the range of, e.g., about 500 fg to about 525 fg, about 500 fg to about 550 fg, about 500 fg to about 575 fg, about 500 fg to about 600 fg, about 500 fg to about 625 fg, about 500 fg to about 650 fg, about 500 fg to about 675 fg, about 500 fg to about 700 fg, about 500 fg to about 725 fg, about 500 fg to about 750 fg, about 500 fg to about 775 fg, about 500 fg to about 800 fg, about 500 fg to about 825 fg, about 500 fg to about 850 fg, about 500 fg to about 875 fg, about 500 fg to about 900 fg, about 500 fg to about 925 fg, about 500 fg to about 950 fg, about 500 fg to about 975 fg, about 500 fg to about 1,000 fg, about 600 fg to about 625 fg, about 600 fg to about 650 fg, about 600 fg to about 675 fg, about 600 fg to about 700 fg, about 600 fg to about 725 fg, about 600 fg to about 750 fg, about 600 fg to about 775 fg, about 600 fg to about 800 fg, about 600 fg to about 825 fg, about 600 fg to about 850 fg, about 600 fg to about 875 fg, about 600 fg to about 900 fg, about 600 fg to about 925 fg, about 600 fg to about 950 fg, about 600 fg to about 975 fg, about 600 fg to about 1,000 fg, about 700 fg to about 725 fg, about 700 fg to about 750 fg, about 700 fg to about 775 fg, about 700 fg to about 800 fg, about 700 fg to about 825 fg, about 700 fg to about 850 fg, about 700 fg to about 875 fg, about 700 fg to about 900 fg, about 700 fg to about 925 fg, about 700 fg to about 950 fg, about 700 fg to about 975 fg, about 700 fg to about 1,000 fg, about 800 fg to about 825 fg, about 800 fg to about 850 fg, about 800 fg to about 875 fg, about 800 fg to about 900 fg, about 800 fg to about 925 fg, about 800 fg to about 950 fg, about 800 fg to about 975 fg, or about 800 fg to about 1,000 fg.

In aspects of this embodiment, an amount of a Ranpirnase and/or Amphinase disclosed herein included in a pharmaceutical composition may be, e.g., about 1 ng, about 2 ng, about 3 ng, about 4 ng, about 5 ng, about 6 ng, about 7 ng, about 8 ng, about 9 ng, about 10 ng, about 15 ng, about 20 ng, about 25 ng, about 30 ng, about 35 ng, about 40 ng, about 45 ng, about 50 ng, about 55 ng, about 60 ng, about 65 ng, about 70 ng, about 75 ng, about 80 ng, about 85 ng, about 90 ng, about 95 ng, about 100 ng, about 110 ng, about 120 ng, about 130 ng, about 140 ng, about 150 ng, about 160 ng, about 170 ng, about 180 ng, about 190 ng, about 200 ng, about 210 ng, about 220 ng, about 230 ng, about 240 ng, about 250 ng, 260 ng, about 270 ng, about 280 ng, about 290 ng, about 300 ng, about 310 ng, about 320 ng, about 330 ng, about 340 ng, about 350 ng, 360 ng, about 370 ng, about 380 ng, about 390 ng, about 400 ng, about 410 ng, about 420 ng, about 430 ng, about 440 ng, about 450 ng, 460 ng, about 470 ng, about 480 ng, about 490 ng, about 500 ng, about 510 ng, about 520 ng, about 530 ng, about 540 ng, about 550 ng, 560 ng, about 570 ng, about 580 ng, about 590 ng, about 600 ng, about 610 ng, about 620 ng, about 630 ng, about 640 ng, about 650 ng, 660 ng, about 670 ng, about 680 ng, about 690 ng, about 700 ng, about 710 ng, about 720 ng, about 730 ng, about 740 ng, about 750 ng, 760 ng, about 770 ng, about 780 ng, about 790 ng, about 800 ng, about 810 ng, about 820 ng, about 830 ng, about 840 ng, about 850 ng, 860 ng, about 870 ng, about 880 ng, about 890 ng, about 900 ng, about 910 ng, about 920 ng, about 930 ng, about 940 ng, about 950 ng, 960 ng, about 970 ng, about 980 ng, about 990 ng, or about 1,000 ng.

In other aspects of this embodiment, an amount of a Ranpirnase and/or Amphinase disclosed herein included in a pharmaceutical composition may be, e.g., at least 1 ng, at least 2 ng, at least 3 ng, at least 4 ng, at least 5 ng, at least 6 ng, at least 7 ng, at least 8 ng, at least 9 ng, at least 10 ng, at least 15 ng, at least 20 ng, at least 25 ng, at least 30 ng, at least 35 ng, at least 40 ng, at least 45 ng, at least 50 ng, at least 55 ng, at least 60 ng, at least 65 ng, at least 70 ng, at least 75 ng, at least 80 ng, at least 85 ng, at least 90 ng, at least 95 ng, at least 100 ng, at least 110 ng, at least 120 ng, at least 130 ng, at least 140 ng, at least 150 ng, at least 160 ng, at least 170 ng, at least 180 ng, at least 190 ng, at least 200 ng, at least 210 ng, at least 220 ng, at least 230 ng, at least 240 ng, at least 250 ng, 260 ng, at least 270 ng, at least 280 ng, at least 290 ng, at least 300 ng, at least 310 ng, at least 320 ng, at least 330 ng, at least 340 ng, at least 350 ng, 360 ng, at least 370 ng, at least 380 ng, at least 390 ng, at least 400 ng, at least 410 ng, at least 420 ng, at least 430 ng, at least 440 ng, at least 450 ng, 460 ng, at least 470 ng, at least 480 ng, at least 490 ng, at least 500 ng, at least 510 ng, at least 520 ng, at least 530 ng, at least 540 ng, at least 550 ng, 560 ng, at least 570 ng, at least 580 ng, at least 590 ng, at least 600 ng, at least 610 ng, at least 620 ng, at least 630 ng, at least 640 ng, at least 650 ng, 660 ng, at least 670 ng, at least 680 ng, at least 690 ng, at least 700 ng, at least 710 ng, at least 720 ng, at least 730 ng, at least 740 ng, at least 750 ng, 760 ng, at least 770 ng, at least 780 ng, at least 790 ng, at least 800 ng, at least 810 ng, at least 820 ng, at least 830 ng, at least 840 ng, at least 850 ng, 860 ng, at least 870 ng, at least 880 ng, at least 890 ng, at least 900 ng, at least 910 ng, at least 920 ng, at least 930 ng, at least 940 ng, at least 950 ng, 960 ng, at least 970 ng, at least 980 ng, at least 990 ng, or at least 1,000 ng.

In yet other aspects of this embodiment, an amount of a Ranpirnase and/or Amphinase disclosed herein included in a pharmaceutical composition may be, e.g., at most 1 ng, at most 2 ng, at most 3 ng, at most 4 ng, at most 5 ng, at most 6 ng, at most 7 ng, at most 8 ng, at most 9 ng, at most 10 ng, at most 15 ng, at most 20 ng, at most 25 ng, at most 30 ng, at most 35 ng, at most 40 ng, at most 45 ng, at most 50 ng, at most 55 ng, at most 60 ng, at most 65 ng, at most 70 ng, at most 75 ng, at most 80 ng, at most 85 ng, at most 90 ng, at most 95 ng, at most 100 ng, at most 110 ng, at most 120 ng, at most 130 ng, at most 140 ng, at most 150 ng, at most 160 ng, at most 170 ng, at most 180 ng, at most 190 ng, at most 200 ng, at most 210 ng, at most 220 ng, at most 230 ng, at most 240 ng, at most 250 ng, 260 ng, at most 270 ng, at most 280 ng, at most 290 ng, at most 300 ng, at most 310 ng, at most 320 ng, at most 330 ng, at most 340 ng, at most 350 ng, 360 ng, at most 370 ng, at most 380 ng, at most 390 ng, at most 400 ng, at most 410 ng, at most 420 ng, at most 430 ng, at most 440 ng, at most 450 ng, 460 ng, at most 470 ng, at most 480 ng, at most 490 ng, at most 500 ng, at most 510 ng, at most 520 ng, at most 530 ng, at most 540 ng, at most 550 ng, 560 ng, at most 570 ng, at most 580 ng, at most 590 ng, at most 600 ng, at most 610 ng, at most 620 ng, at most 630 ng, at most 640 ng, at most 650 ng, 660 ng, at most 670 ng, at most 680 ng, at most 690 ng, at most 700 ng, at most 710 ng, at most 720 ng, at most 730 ng, at most 740 ng, at most 750 ng, 760 ng, at most 770 ng, at most 780 ng, at most 790 ng, at most 800 ng, at most 810 ng, at most 820 ng, at most 830 ng, at most 840 ng, at most 850 ng, 860 ng, at most 870 ng, at most 880 ng, at most 890 ng, at most 900 ng, at most 910 ng, at most 920 ng, at most 930 ng, at most 940 ng, at most 950 ng, 960 ng, at most 970 ng, at most 980 ng, at most 990 ng, or at most 1,000 ng.

In still other aspects of this embodiment, an amount of a Ranpirnase and/or Amphinase disclosed herein included in a pharmaceutical composition may be in the range of, e.g., about 1 ng to about 10 ng, about 1 ng to about 20 ng, about 1 ng to about 30 ng, about 1 ng to about 40 ng, about 1 ng to about 50 ng, about 1 ng to about 60 ng, about 1 ng to about 70 ng, about 1 ng to about 80 ng, about 1 ng to about 90 ng, about 1 ng to about 100 ng, about 1 ng to about 110 ng, about 1 ng to about 120 ng, about 1 ng to about 130 ng, about 1 ng to about 140 ng, about 1 ng to about 150 ng, about 5 ng to about 10 ng, about 5 ng to about 20 ng, about 5 ng to about 30 ng, about 5 ng to about 40 ng, about 5 ng to about 50 ng, about 5 ng to about 60 ng, about 5 ng to about 70 ng, about 5 ng to about 80 ng, about 5 ng to about 90 ng, about 5 ng to about 100 ng, about 5 ng to about 110 ng, about 5 ng to about 120 ng, about 5 ng to about 130 ng, about 5 ng to about 140 ng, about 5 ng to about 150 ng, about 10 ng to about 20 ng, about 10 ng to about 30 ng, about 10 ng to about 40 ng, about 10 ng to about 50 ng, about 10 ng to about 60 ng, about 10 ng to about 70 ng, about 10 ng to about 80 ng, about 10 ng to about 90 ng, about 10 ng to about 100 ng, about 10 ng to about 110 ng, about 10 ng to about 120 ng, about 10 ng to about 130 ng, about 10 ng to about 140 ng, about 10 ng to about 150 ng, about 10 ng to about 175 ng, about 10 ng to about 200 ng, about 10 ng to about 225 ng, about 10 ng to about 250 ng, about 25 ng to about 50 ng, about 25 ng to about 75 ng, about 25 ng to about 100 ng, about 25 ng to about 125 ng, about 25 ng to about 150 ng, about 25 ng to about 175 ng, about 25 ng to about 200 ng, about 25 ng to about 225 ng, about 25 ng to about 250 ng, about 50 ng to about 75 ng, about 50 ng to about 100 ng, about 50 ng to about 125 ng, about 50 ng to about 150 ng, about 50 ng to about 175 ng, about 50 ng to about 200 ng, about 50 ng to about 225 ng, about 50 ng to about 250 ng, about 75 ng to about 100 ng, about 75 ng to about 125 ng, about 75 ng to about 150 ng, about 75 ng to about 175 ng, about 75 ng to about 200 ng, about 75 ng to about 225 ng, or about 75 ng to about 250 ng.

In still other aspects of this embodiment, an amount of a Ranpirnase and/or Amphinase disclosed herein included in a pharmaceutical composition may be in the range of, e.g., about 100 ng to about 125 ng, about 100 ng to about 150 ng, about 100 ng to about 175 ng, about 100 ng to about 200 ng, about 100 ng to about 225 ng, about 100 ng to about 250 ng, about 100 ng to about 275 ng, about 100 ng to about 300 ng, about 100 ng to about 325 ng, about 100 ng to about 350 ng, about 100 ng to about 375 ng, about 100 ng to about 400 ng, about 100 ng to about 425 ng, about 100 ng to about 450 ng, about 100 ng to about 475 ng, about 100 ng to about 500 ng, about 100 ng to about 525 ng, about 100 ng to about 550 ng, about 100 ng to about 575 ng, about 100 ng to about 600 ng, about 125 ng to about 150 ng, about 125 ng to about 175 ng, about 125 ng to about 200 ng, about 125 ng to about 225 ng, about 125 ng to about 250 ng, about 125 ng to about 275 ng, about 125 ng to about 300 ng, about 125 ng to about 325 ng, about 125 ng to about 350 ng, about 125 ng to about 375 ng, about 125 ng to about 400 ng, about 125 ng to about 425 ng, about 125 ng to about 450 ng, about 125 ng to about 475 ng, about 125 ng to about 500 ng, about 125 ng to about 525 ng, about 125 ng to about 550 ng, about 125 ng to about 575 ng, about 125 ng to about 600 ng, about 150 ng to about 175 ng, about 150 ng to about 200 ng, about 150 ng to about 225 ng, about 150 ng to about 250 ng, about 150 ng to about 275 ng, about 150 ng to about 300 ng, about 150 ng to about 325 ng, about 150 ng to about 350 ng, about 150 ng to about 375 ng, about 150 ng to about 400 ng, about 150 ng to about 425 ng, about 150 ng to about 450 ng, about 150 ng to about 475 ng, about 150 ng to about 500 ng, about 150 ng to about 525 ng, about 150 ng to about 550 ng, about 150 ng to about 575 ng, about 150 ng to about 600 ng, about 200 ng to about 225 ng, about 200 ng to about 250 ng, about 200 ng to about 275 ng, about 200 ng to about 300 ng, about 200 ng to about 325 ng, about 200 ng to about 350 ng, about 200 ng to about 375 ng, about 200 ng to about 400 ng, about 200 ng to about 425 ng, about 200 ng to about 450 ng, about 200 ng to about 475 ng, about 200 ng to about 500 ng, about 200 ng to about 525 ng, about 200 ng to about 550 ng, about 200 ng to about 575 ng, about 200 ng to about 600 ng, about 200 ng to about 625 ng, about 200 ng to about 650 ng, about 200 ng to about 675 ng, about 200 ng to about 700 ng, about 200 ng to about 725 ng, about 200 ng to about 750 ng, about 200 ng to about 775 ng, about 200 ng to about 800 ng, about 200 ng to about 825 ng, about 200 ng to about 850 ng, about 200 ng to about 875 ng, about 200 ng to about 900 ng, about 200 ng to about 925 ng, about 200 ng to about 950 ng, about 200 ng to about 975 ng, or about 200 ng to about 1,000 ng.

In still other aspects of this embodiment, an amount of a Ranpirnase and/or Amphinase disclosed herein included in a pharmaceutical composition may be in the range of, e.g., about 250 ng to about 275 ng, about 250 ng to about 300 ng, about 250 ng to about 325 ng, about 250 ng to about 350 ng, about 250 ng to about 375 ng, about 250 ng to about 400 ng, about 250 ng to about 425 ng, about 250 ng to about 450 ng, about 250 ng to about 475 ng, about 250 ng to about 500 ng, about 250 ng to about 525 ng, about 250 ng to about 550 ng, about 250 ng to about 575 ng, about 250 ng to about 600 ng, about 250 ng to about 625 ng, about 250 ng to about 650 ng, about 250 ng to about 675 ng, about 250 ng to about 700 ng, about 250 ng to about 725 ng, about 250 ng to about 750 ng, about 250 ng to about 775 ng, about 250 ng to about 800 ng, about 250 ng to about 825 ng, about 250 ng to about 850 ng, about 250 ng to about 875 ng, about 250 ng to about 900 ng, about 250 ng to about 925 ng, about 250 ng to about 950 ng, about 250 ng to about 975 ng, about 250 ng to about 1,000 ng, about 300 ng to about 325 ng, about 300 ng to about 350 ng, about 300 ng to about 375 ng, about 300 ng to about 400 ng, about 300 ng to about 425 ng, about 300 ng to about 450 ng, about 300 ng to about 475 ng, about 300 ng to about 500 ng, about 300 ng to about 525 ng, about 300 ng to about 550 ng, about 300 ng to about 575 ng, about 300 ng to about 600 ng, about 300 ng to about 625 ng, about 300 ng to about 650 ng, about 300 ng to about 675 ng, about 300 ng to about 700 ng, about 300 ng to about 725 ng, about 300 ng to about 750 ng, about 300 ng to about 775 ng, about 300 ng to about 800 ng, about 300 ng to about 825 ng, about 300 ng to about 850 ng, about 300 ng to about 875 ng, about 300 ng to about 900 ng, about 300 ng to about 925 ng, about 300 ng to about 950 ng, about 300 ng to about 975 ng, about 300 ng to about 1,000 ng, about 400 ng to about 425 ng, about 400 ng to about 450 ng, about 400 ng to about 475 ng, about 400 ng to about 500 ng, about 400 ng to about 525 ng, about 400 ng to about 550 ng, about 400 ng to about 575 ng, about 400 ng to about 600 ng, about 400 ng to about 625 ng, about 400 ng to about 650 ng, about 400 ng to about 675 ng, about 400 ng to about 700 ng, about 400 ng to about 725 ng, about 400 ng to about 750 ng, about 400 ng to about 775 ng, about 400 ng to about 800 ng, about 400 ng to about 825 ng, about 400 ng to about 850 ng, about 400 ng to about 875 ng, about 400 ng to about 900 ng, about 400 ng to about 925 ng, about 400 ng to about 950 ng, about 400 ng to about 975 ng, or about 400 ng to about 1,000 ng.

In still other aspects of this embodiment, an amount of a Ranpirnase and/or Amphinase disclosed herein included in a pharmaceutical composition may be in the range of, e.g., about 500 ng to about 525 ng, about 500 ng to about 550 ng, about 500 ng to about 575 ng, about 500 ng to about 600 ng, about 500 ng to about 625 ng, about 500 ng to about 650 ng, about 500 ng to about 675 ng, about 500 ng to about 700 ng, about 500 ng to about 725 ng, about 500 ng to about 750 ng, about 500 ng to about 775 ng, about 500 ng to about 800 ng, about 500 ng to about 825 ng, about 500 ng to about 850 ng, about 500 ng to about 875 ng, about 500 ng to about 900 ng, about 500 ng to about 925 ng, about 500 ng to about 950 ng, about 500 ng to about 975 ng, about 500 ng to about 1,000 ng, about 600 ng to about 625 ng, about 600 ng to about 650 ng, about 600 ng to about 675 ng, about 600 ng to about 700 ng, about 600 ng to about 725 ng, about 600 ng to about 750 ng, about 600 ng to about 775 ng, about 600 ng to about 800 ng, about 600 ng to about 825 ng, about 600 ng to about 850 ng, about 600 ng to about 875 ng, about 600 ng to about 900 ng, about 600 ng to about 925 ng, about 600 ng to about 950 ng, about 600 ng to about 975 ng, about 600 ng to about 1,000 ng, about 700 ng to about 725 ng, about 700 ng to about 750 ng, about 700 ng to about 775 ng, about 700 ng to about 800 ng, about 700 ng to about 825 ng, about 700 ng to about 850 ng, about 700 ng to about 875 ng, about 700 ng to about 900 ng, about 700 ng to about 925 ng, about 700 ng to about 950 ng, about 700 ng to about 975 ng, about 700 ng to about 1,000 ng, about 800 ng to about 825 ng, about 800 ng to about 850 ng, about 800 ng to about 875 ng, about 800 ng to about 900 ng, about 800 ng to about 925 ng, about 800 ng to about 950 ng, about 800 ng to about 975 ng, or about 800 ng to about 1,000 ng.

In aspects of this embodiment, an amount of a Ranpirnase and/or Amphinase disclosed herein included in a pharmaceutical composition may be, e.g., about 1 µg, about 2 µg, about 3 µg, about 4 µg, about 5 µg, about 6 µg, about 7 µg, about 8 µg, about 9 µg, about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, about 230 µg, about 240 µg, about 250 µg, 260 µg, about 270 µg, about 280 µg, about 290 µg, about 300 µg, about 310 µg, about 320 µg, about 330 µg, about 340 µg, about 350 µg, 360 µg, about 370 µg, about 380 µg, about 390 µg, about 400 µg, about 410 µg, about 420 µg, about 430 µg, about 440 µg, about 450 µg, 460 µg, about 470 µg, about 480 µg, about 490 µg, about 500 µg, about 510 µg, about 520 µg, about 530 µg, about 540 µg, about 550 µg, 560 µg, about 570 µg, about 580 µg, about 590 µg, about 600 µg, about 610 µg, about 620 µg, about 630 µg, about 640 µg, about 650 µg, 660 µg, about 670 µg, about 680 µg, about 690 µg, about 700 µg, about 710 µg, about 720 µg, about 730 µg, about 740 µg, about 750 µg, 760 µg, about 770 µg, about 780 µg, about 790 µg, about 800 µg, about 810 µg, about 820 µg, about 830 µg, about 840 µg, about 850 µg, 860 µg, about 870 µg, about 880 µg, about 890 µg, about 900 µg, about 910 µg, about 920 µg, about 930 µg, about 940 µg, about 950 µg, 960 µg, about 970 µg, about 980 µg, about 990 µg, or about 1,000 µg.

In other aspects of this embodiment, an amount of a Ranpirnase and/or Amphinase disclosed herein included in a pharmaceutical composition may be, e.g., at least 1 µg, at least 2 µg, at least 3 µg, at least 4 µg, at least 5 µg, at least 6 µg, at least 7 µg, at least 8 µg, at least 9 µg, at least 10 µg, at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, at least 100 µg, at least 110 µg, at least 120 µg, at least 130 µg, at least 140 µg, at least 150 µg, at least 160 µg, at least 170 µg, at least 180 µg, at least 190 µg, at least 200 µg, at least 210 µg, at least 220 µg, at least 230 µg, at least 240 µg, at least 250 µg, 260 µg, at least 270 µg, at least 280 µg, at least 290 µg, at least 300 µg, at least 310 µg, at least 320 µg, at least 330 µg, at least 340 µg, at least 350 µg, 360 µg, at least 370 µg, at least 380 µg, at least 390 µg, at least 400 µg, at least 410 µg, at least 420 µg, at least 430 µg, at least 440 µg, at least 450 µg, 460 µg, at least 470 µg, at least 480 µg, at least 490 µg, at least 500 µg, at least 510 µg, at least 520 µg, at least 530 µg, at least 540 µg, at least 550 µg, 560 µg, at least 570 µg, at least 580 µg, at least 590 µg, at least 600 µg, at least 610 µg, at least 620 µg, at least 630 µg, at least 640 µg, at least 650 µg, 660 µg, at least 670 µg, at least 680 µg, at least 690 µg, at least 700 µg, at least 710 µg, at least 720 µg, at least 730 µg, at least 740 µg, at least 750 µg, 760 µg, at least 770 µg, at least 780 µg, at least 790 µg, at least 800 µg, at least 810 µg, at least 820 µg, at least 830 µg, at least 840 µg, at least 850 µg, 860 µg, at least 870 µg, at least 880 µg, at least 890 µg, at least 900 µg, at least 910 µg, at least 920 µg, at least 930 µg, at least 940 µg, at least 950 µg, 960 µg, at least 970 µg, at least 980 µg, at least 990 µg, or at least 1,000 µg.

In yet other aspects of this embodiment, an amount of a Ranpirnase and/or Amphinase disclosed herein included in a pharmaceutical composition may be, e.g., at most 1 µg, at most 2 µg, at most 3 µg, at most 4 µg, at most 5 µg, at most 6 µg, at most 7 µg, at most 8 µg, at most 9 µg, at most 10 µg, at most 15 µg, at most 20 µg, at most 25 µg, at most 30 µg, at most 35 µg, at most 40 µg, at most 45 µg, at most 50 µg, at most 55 µg, at most 60 µg, at most 65 µg, at most 70 µg, at most 75 µg, at most 80 µg, at most 85 µg, at most 90 µg, at most 95 µg, at most 100 µg, at most 110 µg, at most 120 µg, at most 130 µg, at most 140 µg, at most 150 µg, at most 160 µg, at most 170 µg, at most 180 µg, at most 190 µg, at most 200 µg, at most 210 µg, at most 220 µg, at most 230 µg, at most 240 µg, at most 250 µg, 260 µg, at most 270 µg, at most 280 µg, at most 290 µg, at most 300 µg, at most 310 µg, at most 320 µg, at most 330 µg, at most 340 µg, at most 350 µg, 360 µg, at most 370 µg, at most 380 µg, at most 390 µg, at most 400 µg, at most 410 µg, at most 420 µg, at most 430 µg, at most 440 µg, at most 450 µg, 460 µg, at most 470 µg, at most 480 µg, at most 490 µg, at most 500 µg, at most 510 µg, at most 520 µg, at most 530 µg, at most 540 µg, at most 550 µg, 560 µg, at most 570 µg, at most 580 µg, at most 590 µg, at most 600 µg, at most 610 µg, at most 620 µg, at most 630 µg, at most 640 µg, at most 650 µg, 660 µg, at most 670 µg, at most 680 µg, at most 690 µg, at most 700 µg, at most 710 µg, at most 720 µg, at most 730 µg, at most 740 µg, at most 750 µg, 760 µg, at most 770 µg, at most 780 µg, at most 790 µg, at most 800 µg, at most 810 µg, at most 820 µg, at most 830 µg, at most 840 µg, at most 850 µg, 860 µg, at most 870 µg, at most 880 µg, at most 890 µg, at most 900 µg, at most 910 µg, at most 920 µg, at most 930 µg, at most 940 µg, at most 950 µg, 960 µg, at most 970 µg, at most 980 µg, at most 990 µg, or at most 1,000 µg.

In still other aspects of this embodiment, an amount of a Ranpirnase and/or Amphinase disclosed herein included in a pharmaceutical composition may be in the range of, e.g., about 1 µg to about 10 µg, about 1 µg to about 20 µg, about 1 µg to about 30 µg, about 1 µg to about 40 µg, about 1 µg to about 50 µg, about 1 µg to about 60 µg, about 1 µg to about 70 µg, about 1 µg to about 80 µg, about 1 µg to about 90 µg, about 1 µg to about 100 µg, about 1 µg to about 110 µg, about 1 µg to about 120 µg, about 1 µg to about 130 µg, about 1 µg to about 140 µg, about 1 µg to about 150 µg, about 5 µg to about 10 µg, about 5 µg to about 20 µg, about 5 µg to about 30 µg, about 5 µg to about 40 µg, about 5 µg to about 50 µg, about 5 µg to about 60 µg, about 5 µg to about 70 µg, about 5 µg to about 80 µg, about 5 µg to about 90 µg, about 5 µg to about 100 µg, about 5 µg to about 110 µg, about 5 µg to about 120 µg, about 5 µg to about 130 µg, about 5 µg to about 140 µg, about 5 µg to about 150 µg, about 10 µg to about 20 µg, about 10 µg to about 30 µg, about 10 µg to about 40 µg, about 10 µg to about 50 µg, about 10 µg to about 60 µg, about 10 µg to about 70 µg, about 10 µg to about 80 µg, about 10 µg to about 90 µg, about 10 µg to about 100 µg, about 10 µg to about 110 µg, about 10 µg to about 120 µg, about 10 µg to about 130 µg, about 10 µg to about 140 µg, about 10 µg to about 150 µg, about 10 µg to about 175 µg, about 10 µg to about 200 µg, about 10 µg to about 225 µg, about 10 µg to about 250 µg, about 25 µg to about 50 µg, about 25 µg to about 75 µg, about 25 µg to about 100 µg, about 25 µg to about 125 µg, about 25 µg to about 150 µg, about 25 µg to about 175 µg, about 25 µg to about 200 µg, about 25 µg to about 225 µg, about 25 µg to about 250 µg, about 50 µg to about 75 µg, about 50 µg to about 100 µg, about 50 µg to about 125 µg, about 50 µg to about 150 µg, about 50 µg to about 175 µg, about 50 µg to about 200 µg, about 50 µg to about 225 µg, about 50 µg to about 250 µg, about 75 µg to about 100 µg, about 75 µg to about 125 µg, about 75 µg to about 150 µg, about 75 µg to about 175 µg, about 75 µg to about 200 µg, about 75 µg to about 225 µg, or about 75 µg to about 250 µg.

In still other aspects of this embodiment, an amount of a Ranpirnase and/or Amphinase disclosed herein included in a pharmaceutical composition may be in the range of, e.g., about 100 µg to about 125 µg, about 100 µg to about 150 µg, about 100 µg to about 175 µg, about 100 µg to about 200 µg, about 100 µg to about 225 µg, about 100 µg to about 250 µg, about 100 µg to about 275 µg, about 100 µg to about 300 µg, about 100 µg to about 325 µg, about 100 µg to about 350 µg, about 100 µg to about 375 µg, about 100 µg to about 400 µg, about 100 µg to about 425 µg, about 100 µg to about 450 µg, about 100 µg to about 475 µg, about 100 µg to about 500 µg, about 100 µg to about 525 µg, about 100 µg to about 550 µg, about 100 µg to about 575 µg, about 100 µg to about 600 µg, about 125 µg to about 150 µg, about 125 µg to about 175 µg, about 125 µg to about 200 µg, about 125 µg to about 225 µg, about 125 µg to about 250 µg, about 125 µg to about 275 µg, about 125 µg to about 300 µg, about 125 µg to about 325 µg, about 125 µg to about 350 µg, about 125 µg to about 375 µg, about 125 µg to about 400 µg, about 125 µg to about 425 µg, about 125 µg to about 450 µg, about 125 µg to about 475 µg, about 125 µg to about 500 µg, about 125 µg to about 525 µg, about 125 µg to about 550 µg, about 125 µg to about 575 µg, about 125 µg to about 600 µg, about 150 µg to about 175 µg, about 150 µg to about 200 µg, about 150 µg to about 225 µg, about 150 µg to about 250 µg, about 150 µg to about 275 µg, about 150 µg to about 300 µg, about 150 µg to about 325 µg, about 150 µg to about 350 µg, about 150 µg to about 375 µg, about 150 µg to about 400 µg, about 150 µg to about 425 µg, about 150 µg to about 450 µg, about 150 µg to about 475 µg, about 150 µg to about 500 µg, about 150 µg to about 525 µg, about 150 µg to about 550 µg, about 150 µg to about 575 µg, about 150 µg to about 600 µg, about 200 µg to about 225 µg, about 200 µg to about 250 µg, about 200 µg to about 275 µg, about 200 µg to about 300 µg, about 200 µg to about 325 µg, about 200 µg to about 350 µg, about 200 µg to about 375 µg, about 200 µg to about 400 µg, about 200 µg to about 425 µg, about 200 µg to about 450 µg, about 200 µg to about 475 µg, about 200 µg to about 500 µg, about 200 µg to about 525 µg, about 200 µg to about 550 µg, about 200 µg to about 575 µg, about 200 µg to about 600 µg, about 200 µg to about 625 µg, about 200 µg to about 650 µg, about 200 µg to about 675 µg, about 200 µg to about 700 µg, about 200 µg to about 725 µg, about 200 µg to about 750 µg, about 200 µg to about 775 µg, about 200 µg to about 800 µg, about 200 µg to about 825 µg, about 200 µg to about 850 µg, about 200 µg to about 875 µg, about 200 µg to about 900 µg, about 200 µg to about 925 µg, about 200 µg to about 950 µg, about 200 µg to about 975 µg, about 200 µg to about 1,000 µg.

In still other aspects of this embodiment, an amount of a Ranpirnase and/or Amphinase disclosed herein included in a pharmaceutical composition may be in the range of, e.g., about 250 µg to about 275 µg, about 250 µg to about 300 µg, about 250 µg to about 325 µg, about 250 µg to about 350 µg, about 250 µg to about 375 µg, about 250 µg to about 400 µg, about 250 µg to about 425 µg, about 250 µg to about 450 µg, about 250 µg to about 475 µg, about 250 µg to about 500 µg, about 250 µg to about 525 µg, about 250 µg to about 550 µg, about 250 µg to about 575 µg, about 250 µg to about 600 µg, about 250 µg to about 625 µg, about 250 µg to about 650 µg, about 250 µg to about 675 µg, about 250 µg to about 700 µg, about 250 µg to about 725 µg, about 250 µg to about 750 µg, about 250 µg to about 775 µg, about 250 µg to about 800 µg, about 250 µg to about 825 µg, about 250 µg to about 850 µg, about 250 µg to about 875 µg, about 250 µg to about 900 µg, about 250 µg to about 925 µg, about 250 µg to about 950 µg, about 250 µg to about 975 µg, about 250 µg to about 1,000 µg, about 300 µg to about 325 µg, about 300 µg to about 350 µg, about 300 µg to about 375 µg, about 300 µg to about 400 µg, about 300 µg to about 425 µg, about 300 µg to about 450 µg, about 300 µg to about 475 µg, about 300 µg to about 500 µg, about 300 µg to about 525 µg, about 300 µg to about 550 µg, about 300 µg to about 575 µg, about 300 µg to about 600 µg, about 300 µg to about 625 µg, about 300 µg to about 650 µg, about 300 µg to about 675 µg, about 300 µg to about 700 µg, about 300 µg to about 725 µg, about 300 µg to about 750 µg, about 300 µg to about 775 µg, about 300 µg to about 800 µg, about 300 µg to about 825 µg, about 300 µg to about 850 µg, about 300 µg to about 875 µg, about 300 µg to about 900 µg, about 300 µg to about 925 µg, about 300 µg to about 950 µg, about 300 µg to about 975 µg, about 300 µg to about 1,000 µg, about 400 µg to about 425 µg, about 400 µg to about 450 µg, about 400 µg to about 475 µg, about 400 µg to about 500 µg, about 400 µg to about 525 µg, about 400 µg to about 550 µg, about 400 µg to about 575 µg, about 400 µg to about 600 µg, about 400 µg to about 625 µg, about 400 µg to about 650 µg, about 400 µg to about 675 µg, about 400 µg to about 700 µg, about 400 µg to about 725 µg, about 400 µg to about 750 µg, about 400 µg to about 775 µg, about 400 µg to about 800 µg, about 400 µg to about 825 µg, about 400 µg to about 850 µg, about 400 µg to about 875 µg, about 400 µg to about 900 µg, about 400 µg to about 925 µg, about 400 µg to about 950 µg, about 400 µg to about 975 µg, about 400 µg to about 1,000 µg.

In still other aspects of this embodiment, an amount of a Ranpirnase and/or Amphinase disclosed herein included in a pharmaceutical composition may be in the range of, e.g., about 500 µg to about 525 µg, about 500 µg to about 550 µg, about 500 µg to about 575 µg, about 500 µg to about 600 µg, about 500 µg to about 625 µg, about 500 µg to about 650 µg, about 500 µg to about 675 µg, about 500 µg to about 700 µg, about 500 µg to about 725 µg, about 500 µg to about 750 µg, about 500 µg to about 775 µg, about 500 µg to about 800 µg, about 500 µg to about 825 µg, about 500 µg to about 850 µg, about 500 µg to about 875 µg, about 500 µg to about 900 µg, about 500 µg to about 925 µg, about 500 µg to about 950 µg, about 500 µg to about 975 µg, about 500 µg to about 1,000 µg, about 600 µg to about 625 µg, about 600 µg to about 650 µg, about 600 µg to about 675 µg, about 600 µg to about 700 µg, about 600 µg to about 725 µg, about 600 µg to about 750 µg, about 600 µg to about 775 µg, about 600 µg to about 800 µg, about 600 µg to about 825 µg, about 600 µg to about 850 µg, about 600 µg to about 875 µg, about 600 µg to about 900 µg, about 600 µg to about 925 µg, about 600 µg to about 950 µg, about 600 µg to about 975 µg, about 600 µg to about 1,000 µg, about 700 µg to about 725 µg, about 700 µg to about 750 µg, about 700 µg to about 775 µg, about 700 µg to about 800 µg, about 700 µg to about 825 µg, about 700 µg to about 850 µg, about 700 µg to about 875 µg, about 700 µg to about 900 µg, about 700 µg to about 925 µg, about 700 µg to about 950 µg, about 700 µg to about 975 µg, about 700 µg to about 1,000 µg, about 800 µg to about 825 µg, about 800 µg to about 850 µg, about 800 µg to about 875 µg, about 800 µg to about 900 µg, about 800 µg to about 925 µg, about 800 µg to about 950 µg, about 800 µg to about 975 µg, about 800 µg to about 1,000 µg.

In aspects of this embodiment, an amount of a Ranpirnase and/or Amphinase disclosed herein included in a pharmaceutical composition may be, e.g., about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, 260 mg, about 270 mg, about 280 mg, about 290 mg, about 300 mg, about 310 mg, about 320 mg, about 330 mg, about 340 mg, about 350 mg, 360 mg, about 370 mg, about 380 mg, about 390 mg, about 400 mg, about 410 mg, about 420 mg, about 430 mg, about 440 mg, about 450 mg, 460 mg, about 470 mg, about 480 mg, about 490 mg, about 500 mg, about 510 mg, about 520 mg, about 530 mg, about 540 mg, about 550 mg, 560 mg, about 570 mg, about 580 mg, about 590 mg, about 600 mg, about 610 mg, about 620 mg, about 630 mg, about 640 mg, about 650 mg, 660 mg, about 670 mg, about 680 mg, about 690 mg, about 700 mg, about 710 mg, about 720 mg, about 730 mg, about 740 mg, about 750 mg, 760 mg, about 770 mg, about 780 mg, about 790 mg, about 800 mg, about 810 mg, about 820 mg, about 830 mg, about 840 mg, about 850 mg, 860 mg, about 870 mg, about 880 mg, about 890 mg, about 900 mg, about 910 mg, about 920 mg, about 930 mg, about 940 mg, about 950 mg, 960 mg, about 970 mg, about 980 mg, about 990 mg, about 1,000 mg, about 1,250 mg, about 1,500 mg, about 1,750 mg, about 2,000 mg, about 2,250 mg, about 2,500 mg, about 2,750 mg, or about 3,000 mg.

In other aspects of this embodiment, an amount of a Ranpirnase and/or Amphinase disclosed herein included in a pharmaceutical composition may be, e.g., at least 1 mg, at least 2 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, at least 240 mg, at least 250 mg, 260 mg, at least 270 mg, at least 280 mg, at least 290 mg, at least 300 mg, at least 310 mg, at least 320 mg, at least 330 mg, at least 340 mg, at least 350 mg, 360 mg, at least 370 mg, at least 380 mg, at least 390 mg, at least 400 mg, at least 410 mg, at least 420 mg, at least 430 mg, at least 440 mg, at least 450 mg, 460 mg, at least 470 mg, at least 480 mg, at least 490 mg, at least 500 mg, at least 510 mg, at least 520 mg, at least 530 mg, at least 540 mg, at least 550 mg, 560 mg, at least 570 mg, at least 580 mg, at least 590 mg, at least 600 mg, at least 610 mg, at least 620 mg, at least 630 mg, at least 640 mg, at least 650 mg, 660 mg, at least 670 mg, at least 680 mg, at least 690 mg, at least 700 mg, at least 710 mg, at least 720 mg, at least 730 mg, at least 740 mg, at least 750 mg, 760 mg, at least 770 mg, at least 780 mg, at least 790 mg, at least 800 mg, at least 810 mg, at least 820 mg, at least 830 mg, at least 840 mg, at least 850 mg, 860 mg, at least 870 mg, at least 880 mg, at least 890 mg, at least 900 mg, at least 910 mg, at least 920 mg, at least 930 mg, at least 940 mg, at least 950 mg, 960 mg, at least 970 mg, at least 980 mg, at least 990 mg, at least 1,000 mg, at least 1,250 mg, at least 1,500 mg, at least 1,750 mg, at least 2,000 mg, at least 2,250 mg, at least 2,500 mg, at least 2,750 mg, or at least 3,000 mg.

In yet other aspects of this embodiment, an amount of a Ranpirnase and/or Amphinase disclosed herein included in a pharmaceutical composition may be, e.g., at most 1 mg, at most 2 mg, at most 3 mg, at most 4 mg, at most 5 mg, at most 6 mg, at most 7 mg, at most 8 mg, at most 9 mg, at most 10 mg, at most 15 mg, at most 20 mg, at most 25 mg, at most 30 mg, at most 35 mg, at most 40 mg, at most 45 mg, at most 50 mg, at most 55 mg, at most 60 mg, at most 65 mg, at most 70 mg, at most 75 mg, at most 80 mg, at most 85 mg, at most 90 mg, at most 95 mg, at most 100 mg, at most 110 mg, at most 120 mg, at most 130 mg, at most 140 mg, at most 150 mg, at most 160 mg, at most 170 mg, at most 180 mg, at most 190 mg, at most 200 mg, at most 210 mg, at most 220 mg, at most 230 mg, at most 240 mg, at most 250 mg, 260 mg, at most 270 mg, at most 280 mg, at most 290 mg, at most 300 mg, at most 310 mg, at most 320 mg, at most 330 mg, at most 340 mg, at most 350 mg, 360 mg, at most 370 mg, at most 380 mg, at most 390 mg, at most 400 mg, at most 410 mg, at most 420 mg, at most 430 mg, at most 440 mg, at most 450 mg, 460 mg, at most 470 mg, at most 480 mg, at most 490 mg, at most 500 mg, at most 510 mg, at most 520 mg, at most 530 mg, at most 540 mg, at most 550 mg, 560 mg, at most 570 mg, at most 580 mg, at most 590 mg, at most 600 mg, at most 610 mg, at most 620 mg, at most 630 mg, at most 640 mg, at most 650 mg, 660 mg, at most 670 mg, at most 680 mg, at most 690 mg, at most 700 mg, at most 710 mg, at most 720 mg, at most 730 mg, at most 740 mg, at most 750 mg, 760 mg, at most 770 mg, at most 780 mg, at most 790 mg, at most 800 mg, at most 810 mg, at most 820 mg, at most 830 mg, at most 840 mg, at most 850 mg, 860 mg, at most 870 mg, at most 880 mg, at most 890 mg, at most 900 mg, at most 910 mg, at most 920 mg, at most 930 mg, at most 940 mg, at most 950 mg, 960 mg, at most 970 mg, at most 980 mg, at most 990 mg, at most 1,000 mg, at most 1,250 mg, at most 1,500 mg, at most 1,750 mg, at most 2,000 mg, at most 2,250 mg, at most 2,500 mg, at most 2,750 mg, or at most 3,000 mg.

In still other aspects of this embodiment, an amount of a Ranpirnase and/or Amphinase disclosed herein included in a pharmaceutical composition may be in the range of, e.g., about 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, about 1 mg to about 90 mg, about 1 mg to about 100 mg, about 1 mg to about 110 mg, about 1 mg to about 120 mg, about 1 mg to about 130 mg, about 1 mg to about 140 mg, about 1 mg to about 150 mg, about 5 mg to about 10 mg, about 5 mg to about 20 mg, about 5 mg to about 30 mg, about 5 mg to about 40 mg, about 5 mg to about 50 mg, about 5 mg to about 60 mg, about 5 mg to about 70 mg, about 5 mg to about 80 mg, about 5 mg to about 90 mg, about 5 mg to about 100 mg, about 5 mg to about 110 mg, about 5 mg to about 120 mg, about 5 mg to about 130 mg, about 5 mg to about 140 mg, about 5 mg to about 150 mg, about 10 mg to about 20 mg, about 10 mg to about 30 mg, about 10 mg to about 40 mg, about 10 mg to about 50 mg, about 10 mg to about 60 mg, about 10 mg to about 70 mg, about 10 mg to about 80 mg, about 10 mg to about 90 mg, about 10 mg to about 100 mg, about 10 mg to about 110 mg, about 10 mg to about 120 mg, about 10 mg to about 130 mg, about 10 mg to about 140 mg, about 10 mg to about 150 mg, about 10 mg to about 175 mg, about 10 mg to about 200 mg, about 10 mg to about 225 mg, about 10 mg to about 250 mg, about 25 mg to about 50 mg, about 25 mg to about 75 mg, about 25 mg to about 100 mg, about 25 mg to about 125 mg, about 25 mg to about 150 mg, about 25 mg to about 175 mg, about 25 mg to about 200 mg, about 25 mg to about 225 mg, about 25 mg to about 250 mg, about 50 mg to about 75 mg, about 50 mg to about 100 mg, about 50 mg to about 125 mg, about 50 mg to about 150 mg, about 50 mg to about 175 mg, about 50 mg to about 200 mg, about 50 mg to about 225 mg, about 50 mg to about 250 mg, about 75 mg to about 100 mg, about 75 mg to about 125 mg, about 75 mg to about 150 mg, about 75 mg to about 175 mg, about 75 mg to about 200 mg, about 75 mg to about 225 mg, or about 75 mg to about 250 mg.

In still other aspects of this embodiment, an amount of a Ranpirnase and/or Amphinase disclosed herein included in a pharmaceutical composition may be in the range of, e.g., about 100 mg to about 125 mg, about 100 mg to about 150 mg, about 100 mg to about 175 mg, about 100 mg to about 200 mg, about 100 mg to about 225 mg, about 100 mg to about 250 mg, about 100 mg to about 275 mg, about 100 mg to about 300 mg, about 100 mg to about 325 mg, about 100 mg to about 350 mg, about 100 mg to about 375 mg, about 100 mg to about 400 mg, about 100 mg to about 425 mg, about 100 mg to about 450 mg, about 100 mg to about 475 mg, about 100 mg to about 500 mg, about 100 mg to about 525 mg, about 100 mg to about 550 mg, about 100 mg to about 575 mg, about 100 mg to about 600 mg, about 125 mg to about 150 mg, about 125 mg to about 175 mg, about 125 mg to about 200 mg, about 125 mg to about 225 mg, about 125 mg to about 250 mg, about 125 mg to about 275 mg, about 125 mg to about 300 mg, about 125 mg to about 325 mg, about 125 mg to about 350 mg, about 125 mg to about 375 mg, about 125 mg to about 400 mg, about 125 mg to about 425 mg, about 125 mg to about 450 mg, about 125 mg to about 475 mg, about 125 mg to about 500 mg, about 125 mg to about 525 mg, about 125 mg to about 550 mg, about 125 mg to about 575 mg, about 125 mg to about 600 mg, about 150 mg to about 175 mg, about 150 mg to about 200 mg, about 150 mg to about 225 mg, about 150 mg to about 250 mg, about 150 mg to about 275 mg, about 150 mg to about 300 mg, about 150 mg to about 325 mg, about 150 mg to about 350 mg, about 150 mg to about 375 mg, about 150 mg to about 400 mg, about 150 mg to about 425 mg, about 150 mg to about 450 mg, about 150 mg to about 475 mg, about 150 mg to about 500 mg, about 150 mg to about 525 mg, about 150 mg to about 550 mg, about 150 mg to about 575 mg, about 150 mg to about 600 mg, about 200 mg to about 225 mg, about 200 mg to about 250 mg, about 200 mg to about 275 mg, about 200 mg to about 300 mg, about 200 mg to about 325 mg, about 200 mg to about 350 mg, about 200 mg to about 375 mg, about 200 mg to about 400 mg, about 200 mg to about 425 mg, about 200 mg to about 450 mg, about 200 mg to about 475 mg, about 200 mg to about 500 mg, about 200 mg to about 525 mg, about 200 mg to about 550 mg, about 200 mg to about 575 mg, about 200 mg to about 600 mg, about 200 mg to about 625 mg, about 200 mg to about 650 mg, about 200 mg to about 675 mg, about 200 mg to about 700 mg, about 200 mg to about 725 mg, about 200 mg to about 750 mg, about 200 mg to about 775 mg, about 200 mg to about 800 mg, about 200 mg to about 825 mg, about 200 mg to about 850 mg, about 200 mg to about 875 mg, about 200 mg to about 900 mg, about 200 mg to about 925 mg, about 200 mg to about 950 mg, about 200 mg to about 975 mg, about 200 mg to about 1,000 mg, about 200 mg to about 1,250 mg, about 200 mg to about 1,500 mg, about 200 mg to about 1,750 mg, about 200 mg to about 2,000 mg, about 200 mg to about 2,250 mg, about 200 mg to about 2,500 mg, about 200 mg to about 2,750 mg, or about 200 mg to about 3,000 mg.

In still other aspects of this embodiment, an amount of a Ranpirnase and/or Amphinase disclosed herein included in a pharmaceutical composition may be in the range of, e.g., about 250 mg to about 275 mg, about 250 mg to about 300 mg, about 250 mg to about 325 mg, about 250 mg to about 350 mg, about 250 mg to about 375 mg, about 250 mg to about 400 mg, about 250 mg to about 425 mg, about 250 mg to about 450 mg, about 250 mg to about 475 mg, about 250 mg to about 500 mg, about 250 mg to about 525 mg, about 250 mg to about 550 mg, about 250 mg to about 575 mg, about 250 mg to about 600 mg, about 250 mg to about 625 mg, about 250 mg to about 650 mg, about 250 mg to about 675 mg, about 250 mg to about 700 mg, about 250 mg to about 725 mg, about 250 mg to about 750 mg, about 250 mg to about 775 mg, about 250 mg to about 800 mg, about 250 mg to about 825 mg, about 250 mg to about 850 mg, about 250 mg to about 875 mg, about 250 mg to about 900 mg, about 250 mg to about 925 mg, about 250 mg to about 950 mg, about 250 mg to about 975 mg, about 250 mg to about 1,000 mg, about 300 mg to about 325 mg, about 300 mg to about 350 mg, about 300 mg to about 375 mg, about 300 mg to about 400 mg, about 300 mg to about 425 mg, about 300 mg to about 450 mg, about 300 mg to about 475 mg, about 300 mg to about 500 mg, about 300 mg to about 525 mg, about 300 mg to about 550 mg, about 300 mg to about 575 mg, about 300 mg to about 600 mg, about 300 mg to about 625 mg, about 300 mg to about 650 mg, about 300 mg to about 675 mg, about 300 mg to about 700 mg, about 300 mg to about 725 mg, about 300 mg to about 750 mg, about 300 mg to about 775 mg, about 300 mg to about 800 mg, about 300 mg to about 825 mg, about 300 mg to about 850 mg, about 300 mg to about 875 mg, about 300 mg to about 900 mg, about 300 mg to about 925 mg, about 300 mg to about 950 mg, about 300 mg to about 975 mg, about 300 mg to about 1,000 mg, about 400 mg to about 425 mg, about 400 mg to about 450 mg, about 400 mg to about 475 mg, about 400 mg to about 500 mg, about 400 mg to about 525 mg, about 400 mg to about 550 mg, about 400 mg to about 575 mg, about 400 mg to about 600 mg, about 400 mg to about 625 mg, about 400 mg to about 650 mg, about 400 mg to about 675 mg, about 400 mg to about 700 mg, about 400 mg to about 725 mg, about 400 mg to about 750 mg, about 400 mg to about 775 mg, about 400 mg to about 800 mg, about 400 mg to about 825 mg, about 400 mg to about 850 mg, about 400 mg to about 875 mg, about 400 mg to about 900 mg, about 400 mg to about 925 mg, about 400 mg to about 950 mg, about 400 mg to about 975 mg, about 400 mg to about 1,000 mg, about 400 mg to about 1,250 mg, about 400 mg to about 1,500 mg, about 400 mg to about 1,750 mg, about 400 mg to about 2,000 mg, about 400 mg to about 2,250 mg, about 400 mg to about 2,500 mg, about 400 mg to about 2,750 mg, or about 400 mg to about 3,000 mg.

In still other aspects of this embodiment, an amount of a Ranpirnase and/or Amphinase disclosed herein included in a pharmaceutical composition may be in the range of, e.g., about 500 mg to about 525 mg, about 500 mg to about 550 mg, about 500 mg to about 575 mg, about 500 mg to about 600 mg, about 500 mg to about 625 mg, about 500 mg to about 650 mg, about 500 mg to about 675 mg, about 500 mg to about 700 mg, about 500 mg to about 725 mg, about 500 mg to about 750 mg, about 500 mg to about 775 mg, about 500 mg to about 800 mg, about 500 mg to about 825 mg, about 500 mg to about 850 mg, about 500 mg to about 875 mg, about 500 mg to about 900 mg, about 500 mg to about 925 mg, about 500 mg to about 950 mg, about 500 mg to about 975 mg, about 500 mg to about 1,000 mg, about 600 mg to about 625 mg, about 600 mg to about 650 mg, about 600 mg to about 675 mg, about 600 mg to about 700 mg, about 600 mg to about 725 mg, about 600 mg to about 750 mg, about 600 mg to about 775 mg, about 600 mg to about 800 mg, about 600 mg to about 825 mg, about 600 mg to about 850 mg, about 600 mg to about 875 mg, about 600 mg to about 900 mg, about 600 mg to about 925 mg, about 600 mg to about 950 mg, about 600 mg to about 975 mg, about 600 mg to about 1,000 mg, about 700 mg to about 725 mg, about 700 mg to about 750 mg, about 700 mg to about 775 mg, about 700 mg to about 800 mg, about 700 mg to about 825 mg, about 700 mg to about 850 mg, about 700 mg to about 875 mg, about 700 mg to about 900 mg, about 700 mg to about 925 mg, about 700 mg to about 950 mg, about 700 mg to about 975 mg, about 700 mg to about 1,000 mg, about 800 mg to about 825 mg, about 800 mg to about 850 mg, about 800 mg to about 875 mg, about 800 mg to about 900 mg, about 800 mg to about 925 mg, about 800 mg to about 950 mg, about 800 mg to about 975 mg, about 800 mg to about 1,000 mg, about 800 mg to about 1,250 mg, about 800 mg to about 1,500 mg, about 800 mg to about 1,750 mg, about 800 mg to about 2,000 mg, about 800 mg to about 2,250 mg, about 800 mg to about 2,500 mg, about 800 mg to about 2,750 mg, or about 800 mg to about 3,000 mg.

A pharmaceutical composition disclosed herein may optionally include a pharmaceutically-acceptable carrier that facilitates processing of an active ingredient into pharmaceutically-acceptable compositions. As used herein, the term "pharmacologically-acceptable carrier" is synonymous with "pharmacological carrier" and means any carrier that has substantially no long term or permanent detrimental effect when administered and encompasses terms such as "pharmacologically acceptable vehicle, stabilizer, diluent, additive, auxiliary or excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., PURITE® and chelants, such as, e.g., DTPA or DTPA-bisamide, calcium DTPA, and CaNaDTPA-bisamide. Many of these preservatives have bactericidal properties. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

A pharmaceutical composition disclosed herein may be formulated for either local or systemic delivery using topical, ophthalmic, enteral or parenteral routes of administration. In addition, a pharmaceutical composition disclosed herein may be produced as a liquid formulation, a semi-solid formulation, or a solid formulation. A formulation disclosed herein can be produced in a manner to form one phase, such as, e.g., an oil or a solid. Alternatively, a formulation disclosed herein can be produced in a manner to form two phase, such as, e.g., a colloidal formulation. A pharmaceutical composition disclosed herein intended for such administration may be prepared according to any method known to the art for the manufacture of pharmaceutical compositions. Liquid formulations suitable for topical and ophthalmologic administration include, without limitation, solutions and emulsions. Semi-solid formulations suitable for topical and ophthalmologic administration include, without limitation, ointments, creams, salves, foams, and gels. Solid formulations suitable for topical and ophthalmologic administration include, without limitation, gel implants, solid sol implants and solid implants.

A formulation disclosed herein may be a simple one or as part of a more complex drug delivery system. Regardless of the formulation, a Ranpirnase and/or Amphinase disclosed herein as well as the pharmaceutically acceptable excipients and components must be compatible with an ophthalmic formulation because the eye is very sensitive to irritants. This includes factors such as osmolarity, pH, temperature and others. A formulation disclosed herein could include pre-optimized ocular wetting solutions such as Refresh artificial tears or other over-the-counter (OTC) tears available today. If more advanced formulations are to be required to extend residence time on the ocular surface, adding co-solvents, surfactants, osmotic agents, complexing agents (such as cyclodextrins), buffers, and viscosity agents or combinations of the above, have successfully been used previously for other therapeutics. Additionally, a Ranpirnase and/or Amphinase disclosed herein may be formulated by itself in a pharmaceutical composition, or may be formulated together with one or more other therapeutic compounds disclosed herein in a single pharmaceutical composition.

A Ranpirnase and/or Amphinase disclosed herein may be formulated in a controlled release delivery platform including a sustained release formulation and an extended release formulation. The ocular surface is a tough target tissue to administer a drug to as tear production immediately dilutes any active ingredient. Further, blinking provides another source of immediately dilution and removal of any active ingredient being delivered. The use of a controlled release delivery platform adheres of the ocular surface to ensure that a Ranpirnase and/or Amphinase disclosed herein remains for a time sufficient to deliver the required dose necessary for therapeutic effect. Such controlled release delivery platform can improve the delivery kinetics of a Ranpirnase and/or Amphinase disclosed herein by releasing in a time controlled fashion, potentially minimizing the number of instillations required over a course of treatment.

An extended release formulation refers to the release of a Ranpirnase and/or Amphinase disclosed herein over a period of time of less than about seven days. A sustained release formulation refers to the release of a Ranpirnase and/or Amphinase disclosed herein over a period of about seven days or more.

In aspects of this embodiment, a sustained release formulation releases a Ranpirnase and/or Amphinase disclosed herein or a pharmaceutical composition disclosed herein with substantially zero order release kinetics over a period of, e.g., about 7 days, about 15 days after administration, about 30 days, about 45 days, about 60 days, about 75 days, or about 90 days after administration. In other aspects of this embodiment, a sustained release formulation releases a Ranpirnase and/or Amphinase disclosed herein or a pharmaceutical composition disclosed herein with substantially zero order release kinetics over a period of, e.g., at least 7 days, at least 15 days, at least 30 days, at least 45 days, at least 60 days, at least 75 days, or at least 90 days after administration. In yet other aspects of this embodiment, a sustained release formulation releases a Ranpirnase and/or Amphinase disclosed herein or a pharmaceutical composition disclosed herein with substantially first order release kinetics over a period of, e.g., about 7 days, about 15 days after administration, about 30 days, about 45 days, about 60 days, about 75 days, or about 90 days after administration. In still other aspects of this embodiment, a sustained release formulation releases a Ranpirnase and/or Amphinase disclosed herein or a pharmaceutical composition disclosed herein with substantially first order release kinetics over a period of, e.g., at least 7 days, at least 15 days, at least 30 days, at least 45 days, at least 60 days, at least 75 days, or at least 90 days after administration.

In aspects of this embodiment, an extended release formulation releases a Ranpirnase and/or Amphinase disclosed herein or a pharmaceutical composition disclosed herein with substantially zero order release kinetics over a period of, e.g., about 1 day, about 2 days, about 3 days, about 4 days, about 5 days, about 6 days, or about 7 days after administration. In other aspects of this embodiment, an extended release formulation releases a Ranpirnase and/or Amphinase disclosed herein or a pharmaceutical composition disclosed herein with substantially zero order release kinetics over a period of, e.g., at most 1 day, at most 2 days, at most 3 days, at most 4 days, at most 5 days, at most 6 days, or at most 7 days after administration. In yet other aspects of this embodiment, an extended release formulation releases a Ranpirnase and/or Amphinase disclosed herein or a pharmaceutical composition disclosed herein with substantially first order release kinetics over a period of, e.g., about 1 day, about 2 days, about 3 days, about 4 days, about 5 days, about 6 days, or about 7 days after administration. In still other aspects of this embodiment, an extended release formulation releases a Ranpirnase and/or Amphinase disclosed herein or a pharmaceutical composition disclosed herein with substantially first order release kinetics over a period of, e.g., at most 1 day, at most 2 days, at most 3 days, at most 4 days, at most 5 days, at most 6 days, or at most 7 days after administration.

Aspects of the present specification disclose, in part, a method of treating an individual with a viral conjunctivitis. In one embodiment, the method comprises the step of administering to an individual in need thereof a Ranpirnase and/or Amphinase disclosed herein or a pharmaceutical composition disclosed herein, wherein administration reduces a symptom associated with the viral conjunctivitis, thereby treating the individual. Other aspects of the present specification disclose, in part, use of a Ranpirnase and/or Amphinase disclosed herein in the treatment an individual with a viral conjunctivitis.

Aspects of the present specification disclose, in part, treating an individual suffering from a viral conjunctivitis. As used herein, the term "treating," refers to reducing or eliminating in an individual a clinical symptom of a viral conjunctivitis; or delaying or preventing in an individual the onset of a clinical symptom of a viral conjunctivitis. For example, the term "treating" can mean reducing a symptom of a condition characterized by a viral conjunctivitis by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with a viral conjunctivitis are well known and can be determined by a person of ordinary skill in the art by taking into account factors, including, without limitation, the duration of the viral conjunctivitis, the particular viral pathogen, and/or the severity of the viral conjunctivitis. Non-limiting examples of symptoms associated with a viral conjunctivitis disclosed herein include scleral redness, scleral swelling, scleral leakage, inner eyelid redness, inner eyelid swelling, inner eyelid leakage, ocular itching (itchy eyes), foreign body sensation (gritty or scratchy eyes), burning eyes, painful eyes, blurred vision, increased sensitivity to light or photophobia, subepithelial infiltrates, increased tear production, watery discharge, mucopurulent discharge and eyelash crusting. Those of skill in the art will know the appropriate symptoms or indicators associated with a specific type of viral conjunctivitis and will know how to determine if an individual is a candidate for treatment as disclosed herein.

Aspects of the present disclosure comprise, in part, a viral conjunctivitis. Viral conjunctivitis is the most common infectious eye condition today. It is estimated to comprise up to 70% of total conjunctivitis cases seen annually. A viral conjunctivitis disclosed herein includes an epidemic keratoconjunctivitis, a pharyngoconjunctival fever, a nonspecific sporadic follicular conjunctivitis, or a chronic papillary conjunctivitis. Of the virus families that cause human disease, adenoviruses are responsible for up to 90% of the cases. However, other viruses that can also be responsible for conjunctival infection include herpes simplex virus (HSV), varicella-zoster virus (VZV), picornavirus (enterovirus 70, Coxsackie A24), and poxvirus (*Molluscum contagiosum* virus, vaccinia).

Adenoviruses (members of the family Adenoviridae) are medium-sized (90 to 100 nm), non-enveloped viruses with an icosahedral nucleocapsid containing a double-stranded DNA genome. Adenoviruses have a broad range of vertebrate hosts. About 60 distinct adenoviral serotypes have been found to cause a wide range of illnesses in humans, from mild respiratory infections in young children (known as the common cold) to life-threatening multi-organ disease in people with a weakened immune system.

With respect to viral conjunctivitis adenovirus serotypes 3, 4, 7, 8, 11, 13, 19 and 37 appear to be the primary causative agents, although other adenovirus serotypes may also cause viral conjunctivitis. Adenovirus serotypes 3, 7 and 11 are classified as Human adenovirus B; serotype 8, 13, 19 and 37 are classified as Human adenovirus D; and serotype 4 is classified as Human adenovirus E. Because of low natural immunity against adenovirus in the general population, every individual is considered to be susceptible to infection. In addition, conjunctival viral infections initiate a strong immune response. The ability to regulate this response will aid in reducing many of the clinical symptoms associated with viral conjunctivitis.

Clinically, these adenoviruses can cause multiple distinct syndromes, with epidemic keratoconjunctivitis (EKC—primarily serotypes 8, 19, 37) and pharyngoconjunctival fever (PCF—primarily serotypes 3, 4, 7) being the most common. Epidemic Keratoconjunctivitis (EKC) is one of the most common syndromes of acute conjunctivitis, with characteristic clinical features such as sudden onset of acute follicular conjunctivitis, with watery discharge, hyperemia (redness), chemosis, and ipsilateral preauricular lymphadenopathy. Corneal involvement can occur in the form of diffuse, fine, and/or superficial keratitis, epithelial defects, and even subepithelial opacities. In 20-50% of cases, corneal opacities can persist for a few weeks to months. This phenomenon can significantly decrease visual acuity and cause glare symptoms. Treatment is mostly intended to control symptoms through the use of cold compresses and artificial tears. Antivirals (such as cidofovir) and cyclosporine eye drops were tested clinically but no definitive benefit was observed. In very specific cases with severe membranous conjunctivitis, mild topical corticosteroids can be used to control inflammation.

EKC is usually a self-limiting disease. The incubation period is 2-14 days, and the person may remain infectious for 10-14 days after symptoms develop. Symptoms tend to last for 7-21 days. The fellow eye tends to be involved in more than 50% of the cases within 7 days of onset. The signs and symptoms are typically less severe in the fellow eye. It tends to resolve spontaneously without significant complications. However during this period, the patient is usually confined to their homes in effort not to propagate the infection. In rare cases, conjunctival scarring and conjunctival adhesions can occur secondary to membranous conjunctivitis.

EKC epidemics tend to occur in closed institutions (such as schools, hospitals, camps, nursing homes, workplaces). Direct contact with eye secretions is the major mode of transmission. Other possible methods of transmission are air droplets and possibly swimming pools. Adenovirus can be recovered from the eye for as long as 14 days after the onset of clinical symptoms. Also, the role of medical clinics in spreading the disease is well documented. Many epidemics have been initiated in ophthalmology outpatient clinics by direct contact with contaminated diagnostic instruments. Some of the reasons behind the infectious transmission of EKC in hospitals and clinics include the fact that: (1) the virus can remain "viable" for 5 weeks; (2) the virus is resistant to standard disinfectants, such as 70% isopropyl alcohol and ammonia; and (3) the virus sheds from the eye three (3) days before and fourteen (14) days after symptom onset.

Pharyngoconjunctival Fever (PCF) is an acute and highly infectious illness characterized by its associated systemic manifestations, such as fever, pharyngitis, acute follicular conjunctivitis, and regional lymphoid hyperplasia with tender, enlarged preauricular adenopathy. Patients experience a sudden or gradual onset of fever ranging from 100-104° F., lasting up to 10 days. Myalgia, malaise, and GI disturbances frequently are associated with the fever. The pharyngitis may be mild or quite painful. Initial symptoms of conjunctivitis range from slight itching and burning to marked irritation and tearing, but little photophobia. Swelling of the lids may occur within 48 hours. Signs of disease include epiphora, conjunctival hyperemia (redness) and chemosis, subconjunctival hemorrhage, follicular or mild papillary conjunctival reaction, and eyelid edema. Mild crusting of the lids and discharge may occur. PCF most frequently is bilateral, with one eye typically having onset 1-3 days prior to the second eye. With bilateral disease, the first eye generally is affected more severely.

Viral conjunctivitis has two main attributes that need mitigation, the presence and replication of virus and the host immune response that leads to clinical symptoms. For a successful therapy, addressing only one of these two facets is not enough. A Ranpirnase or Amphinase disclosed herein appear to have both antiviral and immunomodulatory mechanisms of action.

In an embodiment, the present specification discloses a method or use of treating a viral conjunctivitis cause by a Human adenovirus B in an individual in need thereof with by administering to the individual a Ranpirnase and/or Amphinase disclosed herein or a pharmaceutical composition disclosed herein, wherein administration reduces a symptom associated with the viral conjunctivitis, thereby treating the individual. In an aspect of this embodiment, the method disclosed herein treats a viral conjunctivitis cause by Human adenovirus B serotype 3, Human adenovirus B serotype 7, Human adenovirus B serotype 11, or any combination thereof.

In an embodiment, the present specification discloses a method or use of treating an epidemic keratoconjunctivitis cause by a Human adenovirus B in an individual in need thereof with by administering to the individual a Ranpirnase and/or Amphinase disclosed herein or a pharmaceutical composition disclosed herein, wherein administration reduces a symptom associated with the viral conjunctivitis, thereby treating the individual. In an aspect of this embodiment, the method disclosed herein treats an epidemic keratoconjunctivitis cause by Human adenovirus B serotype 3, Human adenovirus B serotype 7, Human adenovirus B serotype 11, or any combination thereof.

In an embodiment, the present specification discloses a method or use of treating a pharyngoconjunctival fever cause by a Human adenovirus B in an individual in need thereof with by administering to the individual a Ranpirnase and/or Amphinase disclosed herein or a pharmaceutical composition disclosed herein, wherein administration reduces a symptom associated with the viral conjunctivitis, thereby treating the individual. In an aspect of this embodiment, the method disclosed herein treats a pharyngoconjunctival fever cause by Human adenovirus B serotype 3, Human adenovirus B serotype 7, Human adenovirus B serotype 11, or any combination thereof.

In an embodiment, the present specification discloses a method or use of treating a viral conjunctivitis cause by a Human adenovirus D in an individual in need thereof with by administering to the individual a Ranpirnase and/or Amphinase disclosed herein or a pharmaceutical composition disclosed herein, wherein administration reduces a symptom associated with the viral conjunctivitis, thereby treating the individual. In an aspect of this embodiment, the method disclosed herein treats a viral conjunctivitis cause by Human adenovirus D serotype 8, Human adenovirus D serotype 13, Human adenovirus D serotype 19, Human adenovirus D serotype 37, or any combination thereof.

In an embodiment, the present specification discloses a method or use of treating an epidemic keratoconjunctivitis cause by a Human adenovirus D in an individual in need thereof with by administering to the individual a Ranpirnase and/or Amphinase disclosed herein or a pharmaceutical composition disclosed herein, wherein administration reduces a symptom associated with the viral conjunctivitis, thereby treating the individual. In an aspect of this embodiment, the method disclosed herein treats an epidemic keratoconjunctivitis cause by Human adenovirus D serotype 8, Human adenovirus D serotype 13, Human adenovirus D serotype 19, Human adenovirus D serotype 37, or any combination thereof.

In an embodiment, the present specification discloses a method or use of treating a pharyngoconjunctival fever cause by a Human adenovirus D in an individual in need thereof with by administering to the individual a Ranpirnase and/or Amphinase disclosed herein or a pharmaceutical composition disclosed herein, wherein administration reduces a symptom associated with the viral conjunctivitis, thereby treating the individual. In an aspect of this embodiment, the method disclosed herein treats a pharyngoconjunctival fever cause by Human adenovirus D serotype 8, Human adenovirus D serotype 13, Human adenovirus D serotype 19, Human adenovirus D serotype 37, or any combination thereof.

In an embodiment, the present specification discloses a method or use of treating a viral conjunctivitis cause by a Human adenovirus E in an individual in need thereof with by administering to the individual a Ranpirnase and/or Amphinase disclosed herein or a pharmaceutical composition disclosed herein, wherein administration reduces a symptom associated with the viral conjunctivitis, thereby treating the individual. In an aspect of this embodiment, the method disclosed herein treats a viral conjunctivitis cause by Human adenovirus E serotype 4.

In an embodiment, the present specification discloses a method or use of treating an epidemic keratoconjunctivitis cause by a Human adenovirus E in an individual in need thereof with by administering to the individual a Ranpirnase and/or Amphinase disclosed herein or a pharmaceutical composition disclosed herein, wherein administration reduces a symptom associated with the viral conjunctivitis, thereby treating the individual. In an aspect of this embodiment, the method disclosed herein treats an epidemic keratoconjunctivitis cause by Human adenovirus E serotype 4.

In an embodiment, the present specification discloses a method or use of treating a pharyngoconjunctival fever cause by a Human adenovirus E in an individual in need thereof by administering the individual a Ranpirnase and/or Amphinase disclosed herein or a pharmaceutical composition disclosed herein, wherein administration reduces a symptom associated with the viral conjunctivitis, thereby treating the individual. In an aspect of this embodiment, the method disclosed herein treats a pharyngoconjunctival fever cause by Human adenovirus E serotype 4.

In an embodiment, the present specification discloses a method or use of reducing or suppressing a level of virus or viral titer in an individual in need thereof by administering to the individual a Ranpirnase and/or Amphinase disclosed herein or a pharmaceutical composition disclosed herein, wherein administration reduces or suppresses a level of virus or viral titer. In aspects of this embodiment, the method disclosed herein a virus whose level or viral titer is reduced or suppressed is a Human adenovirus B, a Human adenovirus D, Human adenovirus E, or any combination thereof. In other aspects of this embodiment, the Human adenovirus B may be, e.g., a Human adenovirus B serotype 3, Human adenovirus B serotype 7, Human adenovirus B serotype 11, or any combination thereof. In yet other aspects of this embodiment, the Human adenovirus D may be, e.g., a Human adenovirus D serotype 8, Human adenovirus D serotype 13, Human adenovirus D serotype 19, Human adenovirus D serotype 37, or any combination thereof. In still other aspects of this embodiment, the Human adenovirus E may be, e.g., a Human adenovirus E serotype 4. In other aspects of this embodiment, a method or use disclosed herein reduces or suppresses a level of virus or viral titer in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a method or use disclosed herein reduces or suppresses a level of virus or viral titer in an individual in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, the present specification discloses a method or use of reducing or suppressing viral replication in an individual in need thereof by administering to the individual a Ranpirnase and/or Amphinase disclosed herein or a pharmaceutical composition disclosed herein, wherein administration reduces or suppresses viral replication. In aspects of this embodiment, the method disclosed herein a virus whose viral replication is reduced or suppressed is a Human adenovirus B, a Human adenovirus D, Human adenovirus E, or any combination thereof. In other aspects of this embodiment, the Human adenovirus B may be, e.g., a Human adenovirus B serotype 3, Human adenovirus B serotype 7, Human adenovirus B serotype 11, or any combination thereof. In yet other aspects of this embodiment, the Human adenovirus D may be, e.g., a Human adenovirus D serotype 8, Human adenovirus D serotype 13, Human adenovirus D serotype 19, Human adenovirus D serotype 37, or any combination thereof. In still other aspects of this embodiment, the Human adenovirus E may be, e.g., a Human adenovirus E serotype 4. In other aspects of this embodiment, a method or use disclosed herein reduces or suppresses viral replication in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a method or use disclosed herein reduces or suppresses viral replication in an individual in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, the present specification discloses a method or use of reducing or suppressing protein synthesis in one or more cells of an individual in need thereof by administering to the individual a Ranpirnase and/or Amphinase disclosed herein or a pharmaceutical composition disclosed herein, wherein administration reduces or suppresses protein synthesis in one or more cells. In aspects of this embodiment, a method or use disclosed herein reduces or suppresses protein synthesis in one or more cells of an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a method or use disclosed herein reduces or suppresses protein synthesis in one or more cells of an individual in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, the present specification discloses a method or use of reducing or suppressing level of tRNA in one or more cells of an individual in need thereof by administering to the individual a Ranpirnase and/or Amphinase disclosed herein or a pharmaceutical composition disclosed herein, wherein administration reduces or suppresses level of tRNA in one or more cells of an individual. In aspects of this embodiment, a method or use disclosed herein reduces or suppresses a level of tRNA in one or more cells of an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a method or use disclosed herein reduces or suppresses a level of tRNA in one or more cells of an individual in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, the present specification discloses a method or use of reducing or suppressing a level of an inflammation inducing molecule in an individual in need thereof by administering to the individual a Ranpirnase and/or Amphinase disclosed herein or a pharmaceutical composition disclosed herein, wherein administration reduces or suppresses a level of an inflammation inducing molecule. In aspects of this embodiment, an inflammation inducing molecule disclosed herein is a substance P (SP), a calcitonin gene-related peptide (CGRP), a glutamate, or a combination thereof. In other aspects of this embodiment, a method or use disclosed herein reduces or suppresses a level of an inflammation inducing molecule in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a method or use disclosed herein reduces or suppresses a level of an inflammation inducing molecule in an individual in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, the present specification discloses a method or use of reducing or suppressing a level of an inflammation inducing prostaglandin in an individual in need thereof by administering to the individual a Ranpirnase and/or Amphinase disclosed herein or a pharmaceutical composition disclosed herein, wherein administration reduces or suppresses a level of an inflammation inducing prostaglandin. In aspects of this embodiment, an inflammation inducing prostaglandin disclosed herein is a 15dPGJ2. In other aspects of this embodiment, a method or use disclosed herein reduces or suppresses a level of an inflammation inducing prostaglandin in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a method or use disclosed herein reduces or suppresses a level of an inflammation inducing prostaglandin in an individual in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, the present specification discloses a method or use of stimulating or enhancing a peroxisome proliferator-activated receptor (PPAR) signaling pathway activity in an individual in need thereof by administering to the individual a Ranpirnase and/or Amphinase disclosed herein or a pharmaceutical composition disclosed herein, wherein administration stimulates or enhances a PPAR pathway signal. In aspects of this embodiment, a PPAR signaling pathway activity disclosed herein is a PPAR-α signaling pathway activity, PPAR-γ signaling pathway activity, PPAR-δ (also known as PPAR-β) signaling pathway activity, or any combination thereof. In other aspects of this embodiment, a method or use disclosed herein stimulates or enhances a PPAR signaling pathway activity in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a method or use disclosed herein stimulates or enhances a PPAR signaling pathway activity in an individual in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, the present specification discloses a method or use of promoting the resolving phenotypic change of M1 to M2 in an individual in need thereof by administering to the individual a Ranpirnase and/or Amphinase disclosed herein or a pharmaceutical composition disclosed herein, wherein administration induces apoptosis of Macrophage M1 cells, promotes differentiation of Macrophage M2 cells or both, thereby promoting the resolving phenotypic change of M1 to M2. In an embodiment, the present specification discloses a method or use of modulating a level of a Th1 cytokine and/or a level of a Th2 cytokine in an individual in need thereof by administering to the individual a Ranpirnase and/or Amphinase disclosed herein or a pharmaceutical composition disclosed herein, wherein administration reduces or suppresses a level of Interferon-gamma (IFNγ), Tumor necrosis factor-alpha (TNF-α), Interleukin-1b (IL-1b), Interleukin-12 (IL-12), or a combination thereof released from a Th1 cell, increases or enhances a level of IL-10 released from a Th2 cell, or both, thereby modulating a level of a Th1 cytokine and/or Th2 cytokine. In other aspects of this embodiment, a method or use disclosed herein reduces or suppresses a level of Interferon-gamma (IFNγ), Tumor necrosis factor-alpha (TNF-α), Interleukin-1b (IL-1b), Interleukin-12 (IL-12), or a combination thereof released from a Th1 cell, or increases or enhances a level of IL-10 released from a Th2 cell, or both in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a method or use disclosed herein reduces or suppresses a level of Interferon-gamma (IFNγ), Tumor necrosis factor-alpha (TNF-α), Interleukin-1b (IL-1b), Interleukin-12 (IL-12), or a combination thereof released from a Th1 cell, or increases or enhances a level of IL-10 released from a Th2 cell, or both in an individual in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In an embodiment, the present specification discloses a method or use of reducing or suppressing a NFκB signaling pathway activity in an individual in need thereof by administering to the individual a Ranpirnase and/or Amphinase disclosed herein or a pharmaceutical composition disclosed herein, wherein administration reduces or suppresses the NFκB signaling pathway activity. In other aspects of this embodiment, a method or use disclosed herein stimulates or enhances a NFκB signaling pathway activity in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a method or use disclosed herein stimulates or enhances a NFκB signaling pathway activity in an individual in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

Aspects of the present invention provide, in part, administering a Ranpirnase and/or Amphinase disclosed herein or a pharmaceutical composition disclosed herein. As used herein, the term "administering" refers to any delivery mechanism that provides a Ranpirnase and/or Amphinase disclosed herein or a pharmaceutical composition disclosed herein to an individual that potentially results in a clinically, therapeutically, or experimentally beneficial result. The actual delivery mechanism used to administer a composition disclosed herein to an individual can be determined by a person of ordinary skill in the art by taking into account factors, including, without limitation, the type of viral conjunctivitis, the location of the viral conjunctivitis, the cause of the viral conjunctivitis, the severity of the viral conjunctivitis, the degree of relief desired for viral conjunctivitis, the duration of relief desired for viral conjunctivitis, the level of virus, viral titer, viral replication, protein synthesis, or tRNA desired to be reduced or suppressed, the particular signally pathway, inflammatory molecule, prostaglandin, and/or cytokine being modulated, the particular viral pathogen, Ranpirnase and/or Amphinase, and/or pharmaceutical composition used, the rate of excretion of the particular Ranpirnase and/or Amphinase used, the pharmacodynamics of the particular Ranpirnase and/or Amphinase used, the nature of the other compounds to be included in the pharmaceutical composition, the particular route of administration, the particular characteristics, history and risk factors of the individual, such as, e.g., age, weight, general health and the like, or any combination thereof.

In an embodiment, administering an individual a Ranpirnase and/or Amphinase disclosed herein or a pharmaceutical composition disclosed herein includes administering to a surface of a conjunctiva of an individual, administering to a surface of an eye of an individual, or administering to a surface of a conjunctiva and/or an eye of an individual.

In an embodiment, administering an individual a Ranpirnase and/or Amphinase disclosed herein or a pharmaceutical composition disclosed herein includes administering an implant to a conjunctiva of an individual, administering an implant to an eye of an individual, or administering an implant to a conjunctiva and/or an eye of an individual.

A Ranpirnase and/or Amphinase disclosed herein or a pharmaceutical composition disclosed herein can be administered to an individual using a cellular uptake approach. Administration of a composition disclosed herein using a cellular uptake approach comprise a variety of enteral or parenteral approaches including, without limitation, ophthalmic administration, oral administration in any acceptable form, such as, e.g., tablet, liquid, capsule, powder, or the like; topical administration in any acceptable form, such as, e.g., drops, spray, creams, gels or ointments; intravascular administration in any acceptable form, such as, e.g., intravenous injection, intravenous infusion, intra-arterial injection, intra-arterial infusion and catheter instillation into the vasculature; perk and intra-tissue administration in any acceptable form, such as, e.g., intraperitoneal injection, intramuscular injection, subcutaneous injection, subcutaneous infusion, intraocular injection, retinal injection, or subretinal injection or epidural injection; intravesicular administration in any acceptable form, such as, e.g., catheter instillation; and by placement device, such as, e.g., an implant, a patch, a pellet, a catheter, an osmotic pump, a suppository, a bioerodible delivery system, a non-bioerodible delivery system or another implanted extended or slow release system. An exemplary list of biodegradable polymers and methods of use are described in, e.g., *Handbook of Biodegradable Polymers* (Abraham J. Domb et al., eds., Overseas Publishers Association, 1997).

A Ranpirnase and/or Amphinase disclosed herein or a pharmaceutical composition disclosed herein is typically administered using an ophthalmic formulation and an ophthalmic route of delivery. For example, a Ranpirnase and/or Amphinase disclosed herein or a pharmaceutical composition disclosed herein can be formulated as a topical formulation, such as, e.g., an eye drop, a punctal plug, a salve, an ointment, a lotion, as an enteral formulation, such as, e.g., a tablet, capsule, syrup, or as a parenteral formulation, such as, e.g., an injectable or an intraocular plug. Such formulations can be administered, e.g., ophthalmically via ocular instillation, ocular irrigation or topical implant (punctal plug) or parenterally via intraocular injection or implant, intravitreal injection, intracorneal injection or implant or subconjunctival injection or implant.

A Ranpirnase and/or Amphinase disclosed herein or a pharmaceutical composition disclosed herein is administered in an amount sufficient to treat a viral conjunctivitis, an epidemic keratoconjunctivitis, and/or a pharyngoconjunctival fever, reduce a level of an inflammation inducing molecule and/or an inflammation inducing prostaglandin, stimulate or enhance a peroxisome proliferator-activated receptor (PPAR) pathway signal, promote the resolving phenotypic change of M1 to M2, modulate Th1 and Th2 cytokines, and/or reduce or suppress a NFκB pathway signal. In aspects of this embodiment, the amount of a Ranpirnase and/or Amphinase disclosed herein or a pharmaceutical composition disclosed herein administered is an amount sufficient to reduce one or more physiological conditions or symptom associated with a viral conjunctivitis, an epidemic keratoconjunctivitis, and/or a pharyngoconjunctival fever, reduce a level of an inflammation inducing molecule and/or an inflammation inducing prostaglandin, stimulate or enhance a peroxisome proliferator-activated receptor (PPAR) pathway signal, promote the resolving phenotypic change of M1 to M2, modulate Th1 and Th2 cytokines, and/or reduce or suppress a NFκB pathway signal. As used herein, the term "amount sufficient" includes "effective amount", "effective dose", "therapeutically effective amount" or "therapeutically effective dose" and refers to the minimum amount of a Ranpirnase and/or Amphinase disclosed herein or a pharmaceutical composition disclosed herein necessary to achieve the desired therapeutic effect and includes an amount sufficient to reduce one or more physiological conditions or symptom associated with a viral conjunctivitis, an epidemic keratoconjunctivitis, and/or a pharyngoconjunctival fever, an amount sufficient to reduce a level of an inflammation inducing molecule and/or an inflammation inducing prostaglandin, an amount sufficient to stimulate or enhance a peroxisome proliferator-activated receptor (PPAR) pathway signal, an amount sufficient to promote the resolving phenotypic change of M1 to M2, an amount sufficient to modulate Th1 and Th2 cytokines, and/or an amount sufficient to reduce or suppress a NFκB pathway signal.

In aspects of this embodiment, an effective amount of a Ranpirnase and/or Amphinase disclosed herein or a pharmaceutical composition disclosed herein modulates one or more physiological conditions or symptoms associated with treating a viral conjunctivitis, an epidemic keratoconjunctivitis, and/or a pharyngoconjunctival fever, reducing a level of an inflammation inducing molecule and/or an inflammation inducing prostaglandin, stimulating or enhancing a peroxisome proliferator-activated receptor (PPAR) pathway signal, promoting the resolving phenotypic change of M1 to M2, modulate Th1 and Th2 cytokines, and/or reducing or suppressing a NFκB pathway signal by, e.g., at least 10%, at least 20%, at least 30%, at least 40%, at least 50%, at least 60%, at least 70%, at least 80%, at least 90% or at least 100%. In other aspects of this embodiment, an effective amount of a Ranpirnase and/or Amphinase disclosed herein or a pharmaceutical composition disclosed herein modulates one or more physiological conditions or symptom associated with treating a viral conjunctivitis, an epidemic keratoconjunctivitis, and/or a pharyngoconjunctival fever, reducing a level of an inflammation inducing molecule and/or an inflammation inducing prostaglandin, stimulating or enhancing a peroxisome proliferator-activated receptor (PPAR) pathway signal, promoting the resolving phenotypic change of M1 to M2, modulate Th1 and Th2 cytokines, and/or reducing or suppressing a NFκB pathway signal by, e.g., at most 10%, at most 20%, at most 30%, at most 40%, at most 50%, at most 60%, at most 70%, at most 80%, at most 90% or at most 100%. In yet other aspects of this embodiment, an effective amount of a Ranpirnase and/or Amphinase disclosed herein or a pharmaceutical composition disclosed herein modulates one or more physiological conditions or symptom associated with treating a viral conjunctivitis, an epidemic keratoconjunctivitis, and/or a pharyngoconjunctival fever, reducing a level of an inflammation inducing molecule and/or an inflammation inducing prostaglandin, stimulating or enhancing a peroxisome proliferator-activated receptor (PPAR) pathway signal, promoting the resolving phenotypic change of M1 to M2, modulate Th1 and Th2 cytokines, and/or reducing or suppressing a NFκB pathway signal by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In still other aspects of this embodiment, an effective amount of a Ranpirnase and/or Amphinase disclosed herein or a pharmaceutical composition disclosed herein modulates one or more physiological conditions or symptom associated with treating a viral conjunctivitis, an epidemic keratoconjunctivitis, and/or a pharyngoconjunctival fever, reducing a level of an inflammation inducing molecule and/or an inflammation inducing prostaglandin, stimulating or enhancing a peroxisome proliferator-activated receptor (PPAR) pathway signal, promoting the resolving phenotypic change of M1 to M2, modulate Th1 and Th2 cytokines, and/or reducing or suppressing a NFκB pathway signal for, e.g., at least one week, at least two weeks, at least three weeks, at least one month, at least two months, at least three months, at least four months, at least five months, at least six months, at least seven months, at least eight months, at least nine months, at least ten months, at least eleven months, or at least twelve months.

The actual effective amount of a Ranpirnase and/or Amphinase disclosed herein or a pharmaceutical composition disclosed herein to be administered to an individual can be determined by a person of ordinary skill in the art by taking into account factors, including, without limitation, the type of viral conjunctivitis, the location of the viral conjunctivitis, the cause of the viral conjunctivitis, the severity of the viral conjunctivitis, the degree of relief desired for viral conjunctivitis, the duration of relief desired for viral conjunctivitis, the level of virus, viral titer, viral replication, protein synthesis, or tRNA desired to be reduced or suppressed, the particular signally pathway, inflammatory molecule, prostaglandin, and/or cytokine being modulated, the particular viral pathogen, Ranpirnase and/or Amphinase, and/or pharmaceutical composition used, the rate of excretion of the particular Ranpirnase and/or Amphinase used, the pharmacodynamics of the particular Ranpirnase and/or Amphinase used, the nature of the other compounds to be included in the pharmaceutical composition, the particular route of administration, the particular characteristics, history and risk factors of the individual, such as, e.g., age, weight, general health and the like, or any combination thereof. Additionally, where repeated administration of a Ranpirnase and/or Amphinase disclosed herein or a pharmaceutical composition disclosed herein is used, the actual therapeutically effective amount will further depend upon factors, including, without limitation, the frequency of administration, the half-life of a Ranpirnase and/or Amphinase or a pharmaceutical composition, or any combination thereof. It is known by a person of ordinary skill in the art that an effective amount of a Ranpirnase and/or Amphinase disclosed herein or a pharmaceutical composition disclosed herein can be extrapolated from in vitro assays and in vivo administration studies using animal models prior to administration to humans. Wide variations in the necessary effective amount are to be expected in view of the differing efficiencies of the various routes of administration. For instance, ophthalmic administration generally would be expected to require higher dosage levels than by oral administration, and oral administration generally would be expected to require higher dosage levels than administration by intravenous or intravitreal injection. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors.

In other aspects of this embodiment, an effective amount of a Ranpirnase and/or Amphinase disclosed herein generally is in the range of about 0.001 mg/kg/day to about 100 mg/kg/day. In aspects of this embodiment, an effective amount of a Ranpirnase and/or Amphinase disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day.

In other aspects of this embodiment, an effective amount of a Ranpirnase and/or Amphinase disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a Ranpirnase and/or Amphinase disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a Ranpirnase and/or Amphinase disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a Ranpirnase and/or Amphinase disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a Ranpirnase and/or Amphinase disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In other aspects of this embodiment, an effective amount of a Ranpirnase and/or Amphinase disclosed herein generally is in the range of about 0.001 mg/day to about 100 mg/day. In aspects of this embodiment, an effective amount of a Ranpirnase and/or Amphinase disclosed herein may be, e.g., at least 0.001 mg/day, at least 0.01 mg/day, at least 0.1 mg/day, at least 1.0 mg/day, at least 5.0 mg/day, at least 10 mg/day, at least 15 mg/day, at least 20 mg/day, at least 25 mg/day, at least 30 mg/day, at least 35 mg/day, at least 40 mg/day, at least 45 mg/day, or at least 50 mg/day.

In other aspects of this embodiment, an effective amount of a Ranpirnase and/or Amphinase disclosed herein may be in the range of, e.g., about 0.001 mg/day to about 10 mg/day, about 0.001 mg/day to about 15 mg/day, about 0.001 mg/day to about 20 mg/day, about 0.001 mg/day to about 25 mg/day, about 0.001 mg/day to about 30 mg/day, about 0.001 mg/day to about 35 mg/day, about 0.001 mg/day to about 40 mg/day, about 0.001 mg/day to about 45 mg/day, about 0.001 mg/day to about 50 mg/day, about 0.001 mg/day to about 75 mg/day, or about 0.001 mg/day to about 100 mg/day. In yet other aspects of this embodiment, an effective amount of a Ranpirnase and/or Amphinase disclosed herein may be in the range of, e.g., about 0.01 mg/day to about 10 mg/day, about 0.01 mg/day to about 15 mg/day, about 0.01 mg/day to about 20 mg/day, about 0.01 mg/day to about 25 mg/day, about 0.01 mg/day to about 30 mg/day, about 0.01 mg/day to about 35 mg/day, about 0.01 mg/day to about 40 mg/day, about 0.01 mg/day to about 45 mg/day, about 0.01 mg/day to about 50 mg/day, about 0.01 mg/day to about 75 mg/day, or about 0.01 mg/day to about 100 mg/day. In still other aspects of this embodiment, an effective amount of a Ranpirnase and/or Amphinase disclosed herein may be in the range of, e.g., about 0.1 mg/day to about 10 mg/day, about 0.1 mg/day to about 15 mg/day, about 0.1 mg/day to about 20 mg/day, about 0.1 mg/day to about 25 mg/day, about 0.1 mg/day to about 30 mg/day, about 0.1 mg/day to about 35 mg/day, about 0.1 mg/day to about 40 mg/day, about 0.1 mg/day to about 45 mg/day, about 0.1 mg/day to about 50 mg/day, about 0.1 mg/day to about 75 mg/day, or about 0.1 mg/day to about 100 mg/day.

In other aspects of this embodiment, an effective amount of a Ranpirnase and/or Amphinase disclosed herein may be in the range of, e.g., about 1 mg/day to about 10 mg/day, about 1 mg/day to about 15 mg/day, about 1 mg/day to about 20 mg/day, about 1 mg/day to about 25 mg/day, about 1 mg/day to about 30 mg/day, about 1 mg/day to about 35 mg/day, about 1 mg/day to about 40 mg/day, about 1 mg/day to about 45 mg/day, about 1 mg/day to about 50 mg/day, about 1 mg/day to about 75 mg/day, or about 1 mg/day to about 100 mg/day. In yet other aspects of this embodiment, an effective amount of a Ranpirnase and/or Amphinase disclosed herein may be in the range of, e.g., about 5 mg/day to about 10 mg/day, about 5 mg/day to about 15 mg/day, about 5 mg/day to about 20 mg/day, about 5 mg/day to about 25 mg/day, about 5 mg/day to about 30 mg/day, about 5 mg/day to about 35 mg/day, about 5 mg/day to about 40 mg/day, about 5 mg/day to about 45 mg/day, about 5 mg/day to about 50 mg/day, about 5 mg/day to about 75 mg/day, or about 5 mg/day to about 100 mg/day.

Dosing can be single dosage or cumulative (serial dosing), and can be readily determined by one skilled in the art. For instance, treatment of a viral conjunctivitis, an epidemic keratoconjunctivitis, and/or a pharyngoconjunctival fever, reduction or suppression of a level of an inflammation inducing molecule and/or an inflammation inducing prostaglandin, stimulation or enhancement of a peroxisome proliferator-activated receptor (PPAR) pathway signal, promotion of the resolving phenotypic change of M1 to M2, modulation of Th1 and Th2 cytokines, and/or reduction or suppression of a NFκB pathway signal may comprise a one-time administration of an effective amount of a Ranpirnase and/or Amphinase disclosed herein or a pharmaceutical composition disclosed herein. As a non-limiting example, an effective amount of a Ranpirnase and/or Amphinase disclosed herein or a pharmaceutical composition disclosed herein can be administered once to an individual, e.g., as a single application. Alternatively, treatment of a viral conjunctivitis, an epidemic keratoconjunctivitis, and/or a pharyngoconjunctival fever, reduction or suppression of a level of an inflammation inducing molecule and/or an inflammation inducing prostaglandin, stimulation or enhancement of a peroxisome proliferator-activated receptor (PPAR) pathway signal, promotion of the resolving phenotypic change of M1 to M2, modulation of Th1 and Th2 cytokines, and/or reduction or suppression of a NFκB pathway signal may comprise multiple administrations of an effective amount of a Ranpirnase and/or Amphinase disclosed herein or a pharmaceutical composition disclosed herein carried out over a range of time periods, such as, e.g., one or more times daily, once every few days, weekly, monthly or yearly. As a non-limiting example, a Ranpirnase and/or Amphinase disclosed herein or a pharmaceutical composition disclosed herein can be administered one, two, three, four, five or six times daily to an individual. The timing of administration can vary from individual to individual, depending upon such factors as the severity of an individual's symptoms. For example, an effective amount of a Ranpirnase and/or Amphinase disclosed herein or a pharmaceutical composition disclosed herein can be administered to an individual three to six time daily for an indefinite period of time, or until the individual no longer requires therapy. A person of ordinary skill in the art will recognize that the condition of the individual can be monitored throughout the course of treatment and that the effective amount of a Ranpirnase and/or Amphinase disclosed herein or a pharmaceutical composition disclosed herein that is administered can be adjusted accordingly.

A method or use of treating a viral conjunctivitis disclosed herein substantially affects virally-infected cells. In aspects of this embodiment, a method or use of treating a viral conjunctivitis affects, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, of virally-infected cells. In other aspects of this embodiment, a method or use of treating a viral conjunctivitis affects, e.g., at most 75%, at most 80%, at least 85%, at most 86%, at most 87%, at least 88%, at most 89%, at most 90%, at most 91%, at most 92%, at most 93%, at most 94%, at most 95%, at most 96%, at most 97%, at most 98%, or at most 99%, of virally-infected cells. In yet other aspects of this embodiment, a method or use of treating a viral conjunctivitis affects, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, of virally-infected cells.

A method or use of treating a viral conjunctivitis disclosed herein does not substantially affect nonvirally-infected cells. In aspects of this embodiment, a method or use of treating a viral conjunctivitis does not affect, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, of nonvirally-infected cells. In other aspects of this embodiment, a method or use of treating a viral conjunctivitis does not affect, e.g., at most 75%, at most 80%, at least 85%, at most 86%, at most 87%, at least 88%, at most 89%, at most 90%, at most 91%, at most 92%, at most 93%, at most 94%, at most 95%, at most 96%, at most 97%, at most 98%, or at most 99%, of nonvirally-infected cells. In yet other aspects of this embodiment, a method or use of treating a viral conjunctivitis does not affect, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, of nonvirally-infected cells.

A Ranpirnase and/or Amphinase disclosed herein or a pharmaceutical composition disclosed herein can also be administered to an individual in combination with other therapeutic compounds to increase the overall therapeutic effect of the treatment. The use of multiple compounds to treat an indication can increase the beneficial effects while reducing the presence of side effects. For example, a Ranpirnase and/or Amphinase disclosed herein can either be co-formulated with or administered sequentially with immunomodulatory drugs such as steroids, NSAIDs, cyclosporine A or other therapeutics in order to enhance the immunomodulation achieved using a Ranpirnase and/or Amphinase alone. As another example, a Ranpirnase and/or Amphinase disclosed herein can either be co-formulated with or administered sequentially with antibiotics currently prescribed for bacterial conjunctivitis.

Aspects of the present specification can also be described as follows:

1. A method of treating a viral conjunctivitis in an individual in need thereof, the method comprising administering to a surface of a conjunctiva and/or an eye of the individual a pharmaceutical composition comprising a therapeutic effective amount of one or more Ranpirnases and/or a therapeutic effective amount of one or more Amphinase, wherein administration reduces a symptom associated with the viral conjunctivitis, thereby treating the individual.
2. Use of a pharmaceutical composition comprising one or more Ranpirnases and/or one or more Amphinase for treating of a viral conjunctivitis.
3. The method according to embodiment 1 or the use according to embodiment 2, wherein the viral conjunctivitis is an epidemic keratoconjunctivitis, a pharyngoconjunctival fever, a nonspecific sporadic follicular conjunctivitis, or a chronic papillary conjunctivitis.
4. A method of reducing or suppressing replication of a virus infecting an individual in need thereof, the method comprising administering to a surface of a conjunctiva and/or an eye of the individual a pharmaceutical composition comprising a therapeutic effective amount of one or more Ranpirnases and/or a therapeutic effective amount of one or more Amphinase, wherein administration reduces or suppresses replication of the virus infecting the individual.
5. Use of a pharmaceutical composition comprising one or more Ranpirnases and/or one or more Amphinase for reducing or suppressing replication of a virus infecting an individual.
6. A method of reducing or suppressing protein synthesis in one or more cells of an individual in need thereof, the method comprising administering to a surface of a conjunctiva and/or an eye of the individual a pharmaceutical composition comprising a therapeutic effective amount of one or more Ranpirnases and/or a therapeutic effective amount of one or more Amphinase, wherein administration reduces or suppresses protein synthesis in one or more cells of the individual.
7. Use of a pharmaceutical composition comprising one or more Ranpirnases and/or one or more Amphinase for reducing or suppressing protein synthesis in one or more cells of an individual.
8. A method of reducing or suppressing a level of tRNA in one or more cells of an individual in need thereof, the method comprising administering to a surface of a conjunctiva and/or an eye of the individual a pharmaceutical composition comprising a therapeutic effective amount of one or more Ranpirnases and/or a therapeutic effective amount of one or more Amphinase, wherein administration reduces or suppresses a level of tRNA in one or more cells of the individual.
9. Use of a pharmaceutical composition comprising one or more Ranpirnases and/or one or more Amphinase for reducing or suppressing a level of tRNA in one or more cells of an individual.
10. The method according to any one of embodiments 1, 3, 4, 6 or 8 the use according to according to any one of embodiments 2, 3, 5, 7 or 9 wherein the viral conjunctivitis is cause by a Human adenovirus B.
11. The method or use according to embodiment 10, wherein the Human adenovirus B is a Human adenovirus B serotype 3, a Human adenovirus B serotype 7, a Human adenovirus B serotype 11, or any combination thereof.
12. The method according to any one of embodiments 1, 3, 4, 6, 8, 10 or 11 or the use according to any one of embodiments 2, 3, 5, 7 or 9-11, wherein the viral conjunctivitis is cause by a Human adenovirus D.
13. The method or use according to embodiment 12, wherein the Human adenovirus D is a Human adenovirus D serotype 8, a Human adenovirus D serotype 13, a Human adenovirus D serotype 19, a Human adenovirus D serotype 37, or any combination thereof.
14. The method according to any one of embodiments 1, 3, 4, 6, 8 or 10-13 or the use according to any one of embodiments 2, 3, 5, 7 or 9-13, wherein the viral conjunctivitis is cause by a Human adenovirus E.
15. The method or use according to embodiment 14, wherein the Human adenovirus E is a Human adenovirus E serotype 4.
16. A method of reducing or suppressing a level of an inflammation inducing molecule in an individual in need thereof by administering to a surface of a conjunctiva and/or an eye of the individual a pharmaceutical composition comprising a therapeutic effective amount of one or more Ranpirnases and/or a therapeutic effective amount of one or more Amphinase, wherein administration reduces or suppresses the level of the inflammation inducing molecule in the individual.
17. Use of a pharmaceutical composition comprising one or more Ranpirnases and/or one or more Amphinase for reducing or suppressing a level of an inflammation inducing molecule.
18. The method according to embodiment 16 or use according to embodiment 17, wherein the inflammation inducing molecule is a substance P, a calcitonin gene-related peptide, a glutamate, or a combination thereof.
19. A method of reducing or suppressing a level of an inflammation inducing prostaglandin in an individual in need thereof by administering to a surface of a conjunctiva and/or an eye of the individual a pharmaceutical composition comprising a therapeutic effective amount of one or more Ranpirnases and/or a therapeutic effective amount of one or more Amphinase, wherein administration reduces or suppresses the level of the inflammation inducing prostaglandin in the individual.

20. Use of a pharmaceutical composition comprising one or more Ranpirnases and/or one or more Amphinase for reducing or suppressing a level of an inflammation inducing prostaglandin.

21. The method according to embodiment 19 or use according to embodiment 20, wherein the inflammation inducing prostaglandin is a 15dPGJ2.

22. A method of stimulating or enhancing a peroxisome proliferator-activated receptor (PPAR) signaling pathway activity in an individual in need thereof by administering to a surface of a conjunctiva and/or an eye of the individual a pharmaceutical composition comprising a therapeutic effective amount of one or more Ranpirnases and/or a therapeutic effective amount of one or more Amphinase, wherein administration stimulates or enhances the PPAR signaling pathway activity in the individual.

23. Use of a pharmaceutical composition comprising one or more Ranpirnases and/or one or more Amphinase for stimulating or enhancing a peroxisome proliferator-activated receptor (PPAR) pathway signal.

24. The method according to embodiment 22 or use according to embodiment 23, wherein the PPAR signaling pathway activity is a PPAR-α signaling pathway activity, a PPAR-γ signaling pathway activity, a PPAR-δ (also known as PPAR-β) signaling pathway activity, or any combination thereof 25. A method of promoting the resolving phenotypic change of M1 to M2 in an individual in need thereof by administering to a surface of a conjunctiva and/or an eye of the individual a pharmaceutical composition comprising a therapeutic effective amount of one or more Ranpirnases and/or a therapeutic effective amount of one or more Amphinase, wherein administration induces apoptosis of Macrophage M1 cells, promotes differentiation of Macrophage M2 cells or both, thereby promoting the resolving phenotypic change of M1 to M2 in the individual.

26. Use of a pharmaceutical composition comprising one or more Ranpirnases and/or one or more Amphinase for promoting the resolving phenotypic change of M1 to M2.

27. The use according to embodiment 26, which induces apoptosis of Macrophage M1 cells, promotes differentiation of Macrophage M2 cells or both, thereby promoting the resolving phenotypic change of M1 to M2

28. A method of modulating a level of a Th1 cytokine and/or a level of a Th2 cytokine in an individual in need thereof administering to a surface of a conjunctiva and/or an eye of the individual a pharmaceutical composition comprising a therapeutic effective amount of one or more Ranpirnases and/or a therapeutic effective amount of one or more Amphinase, wherein administration reduces the levels of Interferon-gamma (IFNγ), Tumor necrosis factor-alpha (TNF-α), Interleukin-1b (IL-1b), Interleukin-12 (IL-12), or a combination thereof released from a Th1 cell, increases the level of IL-10 released from a Th2 cell, or both, thereby modulating the level of the Th1 cytokine and/or the Th2 cytokine in the individual.

29. Use of a pharmaceutical composition comprising one or more Ranpirnases and/or one or more Amphinase for modulating a level of a Th1 cytokine and/or a level of a Th2 cytokine.

30. The use according to embodiment 29, which reduces the levels of Interferon-gamma (IFNγ), Tumor necrosis factor-alpha (TNF-α), Interleukin-1b (IL-1b), Interleukin-12 (IL-12), or a combination thereof released from a Th1 cell, increases the level of IL-10 released from a Th2 cell, or both, thereby modulating Th1 and Th2 cytokines.

31. A method of reducing or suppressing a NFκB signaling pathway activity in an individual in need thereof by administering to a surface of a conjunctiva and/or an eye of the individual a pharmaceutical composition comprising a therapeutic effective amount of one or more Ranpirnases and/or a therapeutic effective amount of one or more Amphinase, wherein administration reduces or suppresses the NFκB signaling pathway activity in the individual.

32. Use of a pharmaceutical composition comprising one or more Ranpirnases and/or one or more Amphinase for reducing or suppressing a NFκB signaling pathway activity.

33. The method according to any one of embodiments 1, 3, 4, 6, 8 or 10-16, 18, 19, 21, 22, 24, 25, 28 or 31, or the use according to any one of embodiments 2, 3, 5, 7 or 9-15, 17, 18, 20, 21, 23, 24, 26, 27, 29, 30 or 32, wherein the one or more Ranpirnases comprise the amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26; a sequence having an amino acid identity of at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26; or a sequence having an amino acid identity of about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97% to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26.

34 The method according to any one of embodiments 1, 3, 4, 6, 8 or 10-16, 18, 19, 21, 22, 24, 25, 28, 31 or 33, or the use according to any one of embodiments 2, 3, 5, 7 or 9-15, 17, 18, 20, 21, 23, 24, 26, 27, 29, 30, 32 or 33, wherein the one or more Ranpirnases comprise an amino acid sequence having at least 1, 2, 3, 4, 5, 6, 7, 8, 9, 10, 11, 12, 13, 14, or 15 contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26; or an amino acid sequence having at most 1, 2, 3, 4, 5, 6, 7, 8, 9, 10, 11, 12, 13, 14, or 15 contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26; or an amino acid sequence having at least 1, 2, 3, 4, 5, 6, 7, 8, 9, 10, 11, 12, 13, 14, or 15 non-contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26; or an amino acid sequence having at most 1, 2, 3, 4, 5, 6, 7, 8, 9, 10, 11, 12, 13, 14, or 15 non-contiguous amino acid deletions, additions, and/or substitutions relative to SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26.

35. The method according to any one of embodiments 1, 3, 4, 6, 8 or 10-16, 18, 19, 21, 22, 24, 25, 28, 31, 33 or 34, or the use according to any one of embodiments 2, 3, 5, 7 or 9-15, 17, 18, 20, 21, 23, 24, 26, 27, 29, 30 or 32-34, wherein the one or more Amphinase comprise the amino acid sequence of SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39; or a sequence having an amino acid identity of at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, to SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39; or a sequence having an amino acid identity in the range of about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, to SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39.

36. The method according to any one of embodiments 1, 3, 4, 6, 8 or 10-16, 18, 19, 21, 22, 24, 25, 28, 31 or 33-35, or the use according to any one of embodiments 2, 3, 5, 7 or 9-15, 17, 18, 20, 21, 23, 24, 26, 27, 29, 30 or 32-35, wherein the one or more Amphinase comprise an amino acid sequence having at least 1, 2, 3, 4, 5, 6, 7, 8, 9, 10, 11, 12, 13, 14, or 15 contiguous amino acid deletions, additions, and/or substitutions relative to SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39; or an amino acid sequence having at most 1, 2, 3, 4, 5, 6, 7, 8, 9, 10, 11, 12, 13, 14, or 15 contiguous amino acid deletions, additions, and/or substitutions relative to SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39; or an amino acid sequence having at least 1, 2, 3, 4, 5, 6, 7, 8, 9, 10, 11, 12, 13, 14, or 15 non-contiguous amino acid deletions, additions, and/or substitutions relative to SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39; or an amino acid sequence having at most 1, 2, 3, 4, 5, 6, 7, 8, 9, 10, 11, 12, 13, 14, or 15 non-contiguous amino acid deletions, additions, and/or substitutions relative to SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, or SEQ ID NO: 39.

37. The method according to any one of embodiments 1, 3, 4, 6, 8 or 10-16, 18, 19, 21, 22, 24, 25, 28, 31 or 33-36, or the use according to any one of embodiments 2, 3, 5, 7 or 9-15, 17, 18, 20, 21, 23, 24, 26, 27, 29, 30 or 32-36, wherein administration or use of the one or more Ranpirnase and/or the one or more Amphinase has an antiviral activity that reduces or suppresses a level of virus or viral titer in an individual.

38. The method or use according to embodiment 37, wherein administration or use of the one or more Ranpirnase and/or the one or more Amphinase reduces or suppresses a level of virus or viral titer in an individual by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%; or reduces or suppresses a level of virus or viral titer in an individual in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

39. The method according to any one of embodiments 1, 3, 4, 6, 8 or 10-16, 18, 19, 21, 22, 24, 25, 28, 31 or 33-38, or the use according to any one of embodiments 2, 3, 5, 7 or 9-15, 17, 18, 20, 21, 23, 24, 26, 27, 29, 30 or 32-38, wherein administration or use of the one or more Ranpirnase and/or the one or more Amphinase has an antiviral activity that reduces or suppresses viral replication.

40. The method or use according to embodiment 39, wherein administration or use of the one or more Ranpirnase and/or the one or more Amphinase reduces or suppresses viral replication by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%; or reduces or suppresses viral replication in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

41. The method according to any one of embodiments 1, 3, 4, 6, 8 or 10-16, 18, 19, 21, 22, 24, 25, 28, 31 or 33-40, or the use according to any one of embodiments 2, 3, 5, 7 or 9-15, 17, 18, 20, 21, 23, 24, 26, 27, 29, 30 or 32-40, wherein administration or use of the one or more Ranpirnase and/or the one or more Amphinase has an antiviral activity that reduces or suppresses protein synthesis in one or more cells of an individual.

42. The method or use according to embodiment 41, wherein administration or use of the one or more Ranpirnase and/or the one or more Amphinase reduces or suppresses protein synthesis in one or more cells of an individual by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%; or reduces or suppresses protein synthesis in one or more cells of an individual in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

43. The method according to any one of embodiments 1, 3, 4, 6, 8 or 10-16, 18, 19, 21, 22, 24, 25, 28, 31 or 33-42, or the use according to any one of embodiments 2, 3, 5, 7 or 9-15, 17, 18, 20, 21, 23, 24, 26, 27, 29, 30 or 32-42, wherein administration or use of the one or more Ranpirnase and/or the one or more Amphinase has an antiviral activity that reduces or suppresses a level of tRNA in one or more cells of an individual.

44. The method or use according to embodiment 43, wherein administration or use of the one or more Ranpirnase and/or the one or more Amphinase reduces or suppresses a level of tRNA in one or more cells of an individual by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%; or reduces or suppresses a level of tRNA in one or more cells of an individual in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

45. The method according to any one of embodiments 1, 3, 4, 6, 8 or 10-16, 18, 19, 21, 22, 24, 25, 28, 31 or 33-44, or the use according to any one of embodiments 2, 3, 5, 7 or 9-15, 17, 18, 20, 21, 23, 24, 26, 27, 29, 30 or 32-44, wherein administration or use of the one or more Ranpirnase and/or the one or more Amphinase has an anti-inflammatory activity that reducing a level of an inflammation inducing molecule.

46. The method or use according to embodiment 45, wherein the inflammation inducing molecule is a substance P (SP), calcitonin gene-related peptide (CGRP), glutamate, or a combination thereof.

47. The method or use according to embodiment 45 or embodiment 46, wherein administration or use of the one or more Ranpirnase and/or the one or more Amphinase reduces or suppresses the level of the inflammation inducing molecule by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%; or reduces or suppresses the level of the inflammation inducing molecule in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

48. The method according to any one of embodiments 1, 3, 4, 6, 8 or 10-16, 18, 19, 21, 22, 24, 25, 28, 31 or 33-47, or the use according to any one of embodiments 2, 3, 5, 7 or 9-15, 17, 18, 20, 21, 23, 24, 26, 27, 29, 30 or 32-47, wherein administration or use of the one or more Ranpirnase and/or the one or more Amphinase has an anti-inflammatory activity that reducing a level of an inflammation inducing prostaglandin.

49. The method or use according to embodiment 48, wherein the inflammation inducing prostaglandin is a 15d PGJ2.

50. The method or use according to embodiment 48 or embodiment 49, wherein administration or use of the one or more Ranpirnase and/or the one or more Amphinase reduces or suppresses the level of the inflammation inducing prostaglandin by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%; or reduces or suppresses the level of the inflammation inducing prostaglandin in a range from about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

51. The method according to any one of embodiments 1, 3, 4, 6, 8 or 10-16, 18, 19, 21, 22, 24, 25, 28, 31 or 33-50, or the use according to any one of embodiments 2, 3, 5, 7 or 9-15, 17, 18, 20, 21, 23, 24, 26, 27, 29, 30 or 32-50, wherein administration or use of the one or more Ranpirnase and/or the one or more Amphinase has an anti-inflammatory activity that stimulates or enhances a PPAR signaling pathway activity.

52. The method or use according to embodiment 51, wherein the PPAR signaling pathway activity is a PPAR-α signaling pathway activity, a PPAR-δ signaling pathway activity, a PPAR-γ signaling pathway activity, or a combination thereof.

53. The method or use according to embodiment 51 or embodiment 52, wherein administration or use of the one or more Ranpirnase and/or the one or more Amphinase stimulates or enhances a PPAR signaling pathway activity by at least 5%, at least 15%, at least 25%, at least 50%, at least 60%, at least 70%, at least 80%, or at least 90%; or stimulates or enhances a PPAR signaling pathway activity in a range from about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50%.

54. The method according to any one of embodiments 1, 3, 4, 6, 8 or 10-16, 18, 19, 21, 22, 24, 25, 28, 31 or 33-53, or the use according to any one of embodiments 2, 3, 5, 7 or 9-15, 17, 18, 20, 21, 23, 24, 26, 27, 29, 30 or 32-53, wherein administration or use of the one or more Ranpirnase and/or the one or more Amphinase has an anti-inflammatory activity that promotes a resolving phenotypic change of M1 to M2.

55. The method or use according to embodiment 53, wherein the resolving phenotypic change of M1 to M2 is induction of apoptosis of Macrophage M1 cells, promotion of differentiation of Macrophage M2 cells, or a combination thereof.

56. The method according to any one of embodiments 1, 3, 4, 6, 8 or 10-16, 18, 19, 21, 22, 24, 25, 28, 31 or 33-55, or the use according to any one of embodiments 2, 3, 5, 7 or 9-15, 17, 18, 20, 21, 23, 24, 26, 27, 29, 30 or 32-55, wherein administration or use of the one or more Ranpirnase and/or the one or more Amphinase has an anti-inflammatory activity that modulates a level of a Th1 cytokine and/or a Th2 cytokine.

57. The method or use according to embodiment 56, wherein the modulation of the level of the Th1 cytokine and/or the Th2 cytokine comprises reducing the level of Interferon-gamma (IFNγ), Tumor necrosis factor-alpha (TNF-α), Interleukin-1b (IL-1b), Interleukin-12 (IL-12), or a combination thereof released from a Th1 cell, increasing the level of IL-10 released from a Th2 cell, or any combination thereof.

58. The method or use according to embodiment 56 or embodiment 57, wherein administration or use of the one or more Ranpirnase and/or the one or more Amphinase reduces or suppresses the level of IFNγ, TNF-α, IL-1b, IL-12, or a combination thereof released from a Th1 cell by at least 10%, at least 20%, at least 30%, at least 40%, at least 50%, at least 60%, at least 70%, at least 80%, or at least 90%, or reduces or suppresses the level of IFNγ, TNF-α, IL-1b, IL-12, or a combination thereof released from a Th1 cell in a range from about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

59. The method or use according to any one of embodiments 56-58, wherein administration or use of the one or more Ranpirnase and/or the one or more Amphinase increases or enhances the level of IL-10 released from a Th2 cell by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%; or increases or enhances the level of IL-10 released from a Th2 cell in a range from about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

60. The method according to any one of embodiments 1, 3, 4, 6, 8 or 10-16, 18, 19, 21, 22, 24, 25, 28, 31 or 33-59, or the use according to any one of embodiments 2, 3, 5, 7 or 9-15, 17, 18, 20, 21, 23, 24, 26, 27, 29, 30 or 32-59, wherein administration or use of the one or more Ranpirnase and/or the one or more Amphinase has an anti-inflammatory activity that reduces or suppresses a NFκB signaling pathway activity.

61. The method or use according to embodiment 60, wherein administration or use of the one or more Ranpirnase and/or the one or more Amphinase reduces or suppresses a NFκB signaling pathway activity by at least 10%, at least 20%, at least 30%, at least 40%, at least 50%, at least 60%, at least 70%, at least 80%, or at least 90%; or reduces or suppresses a NFκB signaling pathway activity in a range from about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

62. The method according to any one of embodiments 1, 3, 4, 6, 8 or 10-16, 18, 19, 21, 22, 24, 25, 28, 31 or 33-61, or the use according to any one of embodiments 2, 3, 5, 7 or 9-15, 17, 18, 20, 21, 23, 24, 26, 27, 29, 30 or 32-61, wherein the pharmaceutical composition is formulated for an ophthalmic route of administration.

63. The method or use according to embodiment 62, wherein the pharmaceutical composition further comprises one or more pharmaceutically-acceptable carriers and optionally one or more pharmaceutically-acceptable components.

64. The method or use according to embodiment 62 or embodiment 63, wherein the ophthalmic formulation is a liquid formulation, a colloidal formulation, a semi-solid formulation or a solid formulation.

65. The method or use according to any one of embodiments 62-64, wherein the ophthalmic formulation is administered by an ocular instillation, an ocular irrigation, an intraocular injection, an intracorneal injection, intravitreal injection or a subconjunctival injection.

66. The method or use according to any one of embodiments 62-64, wherein the ophthalmic formulation is a controlled release delivery platform.

67. The method or use according to embodiment 66, wherein the controlled release delivery platform is an extended release formulation or a sustained release formulation.

68. The method or use according to any one of embodiments 62-64, wherein the ophthalmic formulation is an ocular implant, an ophthalmic implant, a punctal plug, an intraocular implant, an intracorneal implant or a subconjunctival implant.

69. The method according to any one of embodiments 1, 3, 4, 6, 8 or 10-16, 18, 19, 21, 22, 24, 25, 28, 31 or 33-68, or the use according to any one of embodiments 2, 3, 5, 7 or 9-15, 17, 18, 20, 21, 23, 24, 26, 27, 29, 30 or 32-68, wherein the Ranpirnase has the N-terminus blocked pyroglutamic acid or pyrrolidone carboxylic acid.

70. Use of a pharmaceutical composition comprising one or more Ranpirnases and/or one or more Amphinase as a medicament for the treatment of a viral conjunctivitis.

71. Use of a pharmaceutical composition comprising one or more Ranpirnases and/or one or more Amphinase as a medicament for reducing or suppressing replication of a virus infecting an individual.

72. Use of a pharmaceutical composition comprising one or more Ranpirnases and/or one or more Amphinase as a medicament for reducing or suppressing protein synthesis in one or more cells of an individual.

73. Use of a pharmaceutical composition comprising one or more Ranpirnases and/or one or more Amphinase as a medicament for reducing or suppressing a level of tRNA in one or more cells of an individual.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to Ranpirnase, Amphinase, compositions comprising Ranpirnase and/or Amphinase, and methods and uses to treat a viral conjunctivitis, an epidemic keratoconjunctivitis, and/or a pharyngoconjunctival fever, reduce a level of an inflammation inducing molecule and/or an inflammation inducing prostaglandin, stimulate or enhance a peroxisome proliferator-activated receptor (PPAR) pathway signal, promote the resolving phenotypic change of M1 to M2, modulate Th1 and Th2 cytokines, and/or reduce or suppress a NFκB pathway signal using Ranpirnase, Amphinase or compositions comprising Ranpirnase and/or Amphinase.

Example 1

In Vitro Antiviral Effects of Ranpirnase

The antiviral activity of Ranpirnase was evaluated using three in vitro assays. In each assay, Human Adenovirus 5 (AD5 strain NYS #98-1836) or Human Adenovirus 8 (Ad8 strain 13306) was used to infect cells in order to determine whether Ranpirnase could inhibited the cytopathic effects of virus in infected cells and/or could reduce the amount of virus being produced from those infected cells.

To assess in vitro cytotoxicity, both a cytopathic effects of a virus (CPE) regression assay and a neutral red lysosomal uptake cell viability assay was performed essentially as described in, e.g., Repetto, et al., *Neutral Red Uptake Assay for the Estimation of Cell Viability/Cytotoxicity*, Nat. Protoc. 3: 1125-1131 (2008), the content of which is hereby incorporated by reference in its entirety. Ninety-six-well plates were seeded with MA-104 cells at $1\times10^5$ cells/mL and incubated overnight at 37° C. with 5% $CO_2$. Ranpirnase was serially diluted in the prescribed test medium using eight half-log dilutions. Each dilution was added to 5 wells of a 96-well plate with 80% to 100% confluent cells, and three wells of each dilution were then infected with one of the two test viruses. Two wells remained uninfected as controls for toxicity. Six wells per plate were set aside as uninfected, untreated cell controls, and six wells per plate were infected with no treatment as virus controls. 2', 3'-Dideoxycytidine (ddC), a known active compound, was assayed in parallel as a positive control. Assay plates were incubated at 37° C. with 5% $CO_2$. After cytopathic effects by microscopic observation were noted, a CPE reduction assay was performed by scoring each well for cytopathic effect on a scale of 1-4 with a score of 4 meaning that all cells showed CPE. After CPE reduction assay was completed, a neutral red lysosomal uptake assay was conducted by filling each well with 0.011% (m/v) neutral red, a vital stain. The plates then were incubated for about 2 hours at 37° C. in the dark. The unincorporated neutral red solution was removed from the wells and the incorporated dye was then eluted by adding Sorensen's citrate-buffered ethanol. The plates were then read on a spectrophotometer at 540 nm to quantify the neutral red taken up by the healthy cells. The optical density of test wells was converted to percent of cell control and normalized to the virus controls.

The concentration of test compound required to inhibit CPE by 50% or reduce red uptake into cells by 50% ($EC_{50}$) was calculated by regression analysis. The toxicity of the compound without virus present was similarly calculated using the uninfected wells treated with test compounds compared with untreated cell controls. The concentration of compound that would cause 50% cytotoxic effects in the absence of virus ($CC_{50}$) was estimated by linear regression analysis. The selectivity index (SI) is the $CC_{50}$ divided by $EC_{50}$. Assays were repeated using four 10-fold dilutions to verify inactive results. When antiviral activity was observed, the CPE/neutral red assay format was used with 8 half-log dilutions plated in triplicate, followed by the harvest of supernatant fluid from these wells to be assayed for infectious virus using the virus yield reduction assay in triplicate to confirm and quantify the antiviral activity of Ranpirnase.

The virus yield reduction assay was used to determine actual virus amounts in the presence and absence of the test compound; this is the confirmatory assay for antiviral activity. After a 5-day incubation at 37° C. in an incubator infused with 5% $CO_2$ (time when maximum CPE was observed in virus-infected control cells), an aliquot of supernatant fluid was removed from each test well. Replicate wells of each compound concentration or control were pooled and frozen at −80° C. Samples were thawed and diluted by 10-fold serial dilutions. A 100 μL aliquot of each dilution was then plated onto 4 replicate wells of 96-well plates seeded with the applicable cells for each virus strain. Plates were incubated as noted above until viral CPE reached its endpoint, then each well was scored microscopically for the presence of viral CPE. The virus titer was determined based on the endpoint using the Reed-Muench method. Test wells were compared with virus control wells, and the concentration of compound required to reduce virus yield by 90% or 1 $log_{10}$ ($EC_{90}$) was calculated by regression analysis.

The experiments revealed that Ranpirnase was found not to inhibit any adenovirus tested, regardless of antiviral assay used (Table 1). For example, over 100 μg/mL of Ranpirnase was required to achieve an EC50 in the CPE reduction assay for both Ad5 and Ad8 infected cells. This is in contrast to ddC for which an EC50 was achieved at 2.1 μg/mL. Similarly, this assay showed that Ranpirnase exhibited significantly high cytotoxicity relative to ddC. Not surprisingly, the SI values for Ranpirnase were very poor while those for ddC were very good (compare 0 vs. >2400). Similar results were observed in the neutral red lysosomal uptake cell viability assay (Table 1).

TABLE 1

In vitro Anti-Adenovirus Effects of Ranpirnase

| | CPE Reduction Assay (μg/mL) | | | Neutral Red Assay (μg/mL) | | | Yield Reduction Assay (μg/mL) | | |
|---|---|---|---|---|---|---|---|---|---|
| | $EC_{50}$ | $CC_{50}$ | SI | $EC_{50}$ | $CC_{50}$ | SI | $EC_{50}$ | $CC_{50}$ | SI |
| Adenovirus 5 | | | | | | | | | |
| Ranpirnase | >100 | 75 | 0[a] | <100 | 52 | 0 | 21.54 | 52 | <2 |
| ddC | 2.1 | <5000 | <2400 | 2.7 | <5000 | <1900 | - | - | - |
| Adenovirus 8 | | | | | | | | | |
| Ranpirnase | <100 | 59 | 0 | <100 | 44 | 0 | 25.1 | 59 | <2 |
| ddC | 2.1 | <5000 | <2400 | 2.7 | <5000 | <1900 | - | - | - |

[a]Cannot be defined.

The in vitro effects of a Ranpirnase or an Amphinase disclosed herein on other Adenovirus serotypes can be assessed in a manner similar to the one discussed above. Other Adenovirus serotypes include, without limitation, a Human adenovirus B serotype 3 (Ad3), Human adenovirus B serotype 7 (Ad7), Human adenovirus B serotype 11 (Ad11), a Human adenovirus D serotype 13 (Ad13), a Human adenovirus D serotype 19 (Ad19), a Human adenovirus D serotype 37 (Ad37) or a Human adenovirus E serotype 4 (Ad4). In addition, the in vivo effects of a Ranpirnase or an Amphinase disclosed herein on other viruses can be assessed in a manner similar to the one discussed above. Other viruses include, without limitation, a herpes simplex virus (HSV), a varicella-zoster virus (VZV), a picornavirus (enterovirus 70, coxsackie A24) or a poxvirus (*Molluscum contagiosum* virus, vaccinia).

Example 2

Cytotoxicity Effects of Ranpirnase

To confirm the cytotoxicity effects of Ranpirnase a plaque reduction assay was performed essentially as described in, e.g., Romanowski, et al., *The In Vitro and In Vivo Evaluation of ddC as a Topical Antiviral for Ocular Adenovirus Infections*, Invest. Ophthalmol. Vis. Sci. 50: 5295-5299 (2009), which is hereby incorporated by reference in its entirety.

To assess in vitro cytotoxicity, 96-well plates were seeded with A549 cells at 1×10⁵ cells/mL and incubated overnight at 37° C. with 5% $CO_2$. Ranpirnase was serially diluted to concentrations of 1.0 μM, 10 μM and 50 μM. After removal of the tissue culture media, 100 μL of each dilution was added to 3 wells of a 96-well plate with 80% to 100% confluent cells. As controls, 100 μL of a lysis buffer containing 0.25% TRITON X-100 was added to 6 wells (positive cytotoxicity control) and 100 μL of tissue culture media with no Ranpirnase was added to 6 wells (negative cytotoxicity control). Each test and control treatment was incubated on the A549 monolayers for 2 days at 37° C. with 5% $CO_2$. A 100 µL aliquot of the fluorometric stain was then added to each well, and the cells incubated for 1 hour at 37° C. with 5% $CO_2$. The fluorometric stain (ALAMARBLUE®, Invitrogen, Carlsbad, Calif.) acts as a redox indicator that is reduced to a fluorescent form by metabolically active living cells. Fluorescence was then be read with a plate reader (Biotek Synergy 2; Biotek), with a 500/27-nm excitation filter and a 620/40-nm emission filter, at a sensitivity of 35. Cytotoxicity was determined by the percentage of residual viable cells after exposure to Ranpirnase (% cytotoxicity=100−[(median florescence drug/median fluorescence no drug)×100], where "drug" was either one of the three concentrations of Ranpirnase or the lysis buffer and "no drug" was the negative control. The observed differences were evaluated statistically using the non-parametric Kruskal-Wallis ANOVA and Duncan's Multiple Comparisons and significance was established at the P≤0.05 confidence level.

The experiments revealed that Ranpirnase produced significant cytotoxicity in A549 cells after 2 days of exposure (Table 2). For example, 50 µM Ranpirnase treatment of A549 cells resulted in cytotoxicity of about 75% of the cells, which is only 7% lower than lysis buffer treatment which served as the positive control. Although cytotoxicity dropped to about 66% for the 10 µM Ranpirnase treatment and about 62% for the 1 µM Ranpirnase treatment, this degree of cytotoxicity is still significantly high.

TABLE 2

Cytotoxic Effects of Ranpirnase

| Assay | Ranpirnase 1.0 µM | Ranpirnase 10 µM | Ranpirnase 50 µM | Lysis Buffer |
|---|---|---|---|---|
| 1 | 60.9% | 65.7% | 75.1% | 82.7% |
| 2 | 61.3% | 66.5% | 74.0% | 82.6% |
| 3 | 63.7% | 67.1% | 75.1% | 82.4% |
| Mean | 62.0% | 66.4% | 75.0% | 82.6% |

To further extend this analysis to assess at what concentration Ranpirnase is not cytotoxic, an additional plaque reduction assay was performed using lower concentrations of Ranpirnase. These experiments were conducts as described above, except that the Ranpirnase concentrations used were 0.001 µM, 0.01 µM, 0.1 µM, 1.0 µM, 10 µM and 50 µM.

The experiments confirmed that Ranpirnase produced significant cytotoxicity in A549 cells after 2 days of exposure (Table 3). For example, 50 µM Ranpirnase treatment of A549 cells resulted in cytotoxicity of about 87% of the cells, which was the same degree of cytotoxicity as observed for the lysis buffer treatment which served as the positive control. Although cytotoxicity dropped to about 33% for the 10 µM Ranpirnase treatment and about 15% for the 1 µM Ranpirnase treatment, this degree of cytotoxicity is still moderately high. Lower degrees of cytotoxicity was observed for the 0.001 µM, 0.01 µM and 0.1 µM Ranpirnase treatment, ranging from 3.2% to 7.4%. However, as any degree of cytotoxicity above 2.5% is deemed problematic, even at these lower concentrations, Ranpirnase exhibited unsatisfactory degrees of cytotoxicity. This is exacerbated by the fact that these lower concentrations are also subtherapeutic amounts.

TABLE 3

Cytotoxic Effects of Ranpirnase

| Assay | Ranpirnase 0.001 µM | 0.01 µM | 0.1 µM | 1.0 µM | 10 µM | 50 µM | Lysis Buffer |
|---|---|---|---|---|---|---|---|
| 1 | 5.7% | 8.6% | 6.0% | 11.1% | 29.1% | 86.7% | 85.5% |
| 2 | 2.3% | 11.7% | 5.3% | 14.6% | 32.7% | 86.7% | 87.5% |
| 3 | 1.6% | 7.9% | 6.1% | 18.1% | 37.3% | 86.4% | 86.7% |
| Mean | 3.2% | 7.4% | 5.8% | 14.6% | 33.0% | 86.6% | 86.6% |

Example 3

In Vivo Antiviral Effects of Ranpirnase

It spite of its poor cytotoxicity profile, the antiviral activity of Ranpirnase was evaluated in vivo using an ocular rabbit replication model. See, e.g., Romanowski, et al., *The In Vitro and In Vivo Evaluation of ddC as a Topical Antiviral for Ocular Adenovirus Infections*, Invest. Ophthalmol. Vis. Sci. 50: 5295-5299 (2009), which is hereby incorporated by reference in its entirety.

To conduct this in vivo assay, 25 NZW rabbit were anesthetized using the general anesthesia ketamine and xylazine and the topical anesthesia proparacaine. Each rabbit was then topically inoculated with 50 µL of Adenovirus serotype Ad5 ($3\times10^7$ pfu/mL) in both eyes after corneal epithelial scarification (12 cross-hatched strokes of a 25 sterile needle). Eyes were closed and gently rubbed for 5 seconds to ensure contact of the virus on all ocular surfaces. Inoculation of both eyes allowed for the reduction in the number of animals needed without jeopardizing statistical validity. Twenty-four hours later, rabbits will be randomly assigned to one of five topical treatment groups: (1A) 25 µM Ranpirnase (n=5), (1B) 2.5 µM Ranpirnase (n=5), (1C) 0.25 µM Ranpirnase (n=5), (1 D) 0.9% saline, as the negative control (n=5) and (CDV) 0.5% Cidofovir, as the positive control (n=4). Ranpirnase and saline control rabbits were treated in both eyes eight times daily for 9 days, whereas cidofovir rabbits were treated in both eyes twice daily for 7 days. All topical solutions (37 µL drops) were instilled with an electronic pipette (EDP; Rainin, Oakland, Calif.) set in the multi-dispense mode. Ocular swabbing to recover adenovirus from tear film and corneal and conjunctival surfaces, after topical anesthesia with proparacaine, was performed at least 1 hour after the final dose on days 0, 1, 3, 4, 5, 7, 9, 11, and 14 after inoculation. The ocular samples from each eye was placed individually into tubes containing 1 mL of medium and were frozen at −70° C. pending viral plaque assay.

The animals were assayed for eye irritation using a Draize scale for ocular lesions. Classification of eye irritation was evaluated for both eyes of each rabbit on day 3 and day 9 using the maximum mean total score (MMTS; Table 4). See, e.g., Kay and Calandra, *Interpretation of Eye Irritation Tests*, J. Soc. Cos. Chem. 13: 281-289 (1962), the content of which is hereby incorporated by reference in its entirety. The MMTS score used was as follows: 0.0-0.5, Non-Irritating (N); 0.6-2.5, Practically Non-Irritating (PN); 2.6-15.0, Minimally Irritating ($M_1$); 15.1-25.0, Mildly Irritating ($M_2$); 25.1-50.0, Moderately Irritating ($M_3$); 50.1-80.0, Severely Irritating (S); 80.1-100.0, Extremely Irritating (E); and 100.1-110.0, Maximally Irritating ($M_x$).

The assessment of eye irritation in shown in Table 4. Ranpirnase also demonstrated dose dependent ocular toxicity when compared to Saline (negative control) and CDV (positive control) in the Ad5/NZW rabbit ocular model. The toxicity was demonstrated by increased ocular surface inflammation (conjunctival redness, chemosis, and discharge) and corneal toxicity manifested by corneal opacity. The 25 μM Ranpirnase treatment demonstrated the most ocular toxicity followed by the 2.5 μM Ranpirnase concentration. The 0.25 μM Ranpirnase concentration demonstrated similar Draize scores to the negative and positive antiviral controls. These experimental results show that treatment with 0.25 μM Ranpirnase showed no eye irritation as compared to both the saline and Cidofovir controls.

TABLE 4

Assessment of Ocular Irritation

| Group | Day 3 | Day 9 |
|---|---|---|
| 1A | 22.0-$M_2$ (Mildly Irritating) | 85.0-E (Extremely Irritating) |
| 1B | 14.6-$M_1$ (Minimally Irritating) | 60.7-S (Severely Irritating) |
| 1C | 7.5-$M_1$ (Minimally Irritating) | 22.5-$M_2$ (Mildly Irritating) |
| 1D | 7.5-$M_1$ (Minimally Irritating) | 22.4-$M_2$ (Mildly Irritating) |
| CDV | 5.9-$M_1$ (Minimally Irritating) | 27.5-$M_3$ (Moderately Irritating) |

1A, 25 μM Ranpirnase;
1B, 25 μM Ranpirnase;
1C, 25 μM Ranpirnase;
1D, 0.9% saline;
CDV, 0.5% Cidofovir The animals were also assayed on day 21 for nasolacrimal duct blockage by performing a Jones Dye test. On Day 21, a drop of sodium fluorescein was placed in each eye and the time to the dye appearing in the ipsilateral nostril was measured. An eye that did not have dye appearing in the ipsilateral nostril after 5 minutes was considered to have a blocked nasolacrimal duct. This assay showed that no Ranpirnase treated rabbits, regardless of concentration, resulted in blocked nasolacrimal ducts. Similarly, negative and positive control rabbits also did not demonstrate occlusive ducts.

The ocular samples were assayed for Ad5 titers by performing a plaque reduction assay. Samples were diluted 1:10 and these dilutions were inoculated onto duplicate wells of a 24 well multi-plate containing A549 monolayers. The virus was adsorbed for 3 hours at 37° C. in a 5% $CO_2$-water vapor atmosphere without constant rocking. After adsorption, 1 mL of medium plus 0.5% methylcellulose was added to each well, and the plates were incubated at 37° C. in a 5% $CO_2$-water vapor atmosphere. After 7 days, the cells were stained with 0.5% gentian violet, and the number of plaques counted using a dissecting microscope (25×). The viral titers were then calculated, and will be expressed as plaque-forming units per milliliter (PFU/mL). Data from the study were analyzed using analysis of variance (ANOVA) with Fisher's pair-wise comparisons and $X^2$ analyses using True Epistat and/or Minitab statistical software. Significance was established at the $P \leq 0.05$ confidence level.

TABLE 5

In vivo Anti-Adenovirus Effects of Ranpirnase

| Group | Day | | | | | | | Total |
|---|---|---|---|---|---|---|---|---|
| | 1 | 3 | 4 | 5 | 7 | 11 | 14 | |
| 1A | 10/10 | 10/10 | 10/10 | 9/10 | 3/10 | 0/10 | 0/10 | 42/70 |
| | 100% | 100% | 100% | 90% | 30% | 0% | 0% | 60% |
| 1B | 10/10 | 10/10 | 10/10 | 8/10 | 7/10 | 0/10 | 0/10 | 45/70 |
| | 100% | 100% | 100% | 80% | 70% | 0% | 0% | 64.3% |
| 1C | 10/10 | 10/10 | 8/8 | 8/8 | 7/8 | 3/8 | 0/8 | 46/60 |
| | 100% | 100% | 100% | 100% | 88% | 38% | 0% | 76.7% |
| 1D | 10/10 | 10/10 | 10/10 | 10/10 | 9/10 | 3/10 | 1/10 | 53/70 |
| | 100% | 100% | 100% | 100% | 90% | 30% | 10% | 75.7% |
| CDV | 8/8 | 8/8 | 8/8 | 8/8 | 5/8 | 0/8 | 0/8 | 37/56 |
| | 100% | 100% | 100% | 100% | 63% | 0% | 0% | 66.1% |

1A, 25 μM Ranpirnase;
1B, 25 μM Ranpirnase;
1C, 25 μM Ranpirnase;
1D, 0.9% saline;
CDV, 0.5% Cidofovir The assessment of cytotoxicity in shown in Table 5. Ranpirnase demonstrated dose dependent antiviral efficacy when compared to the Saline (negative) control in the Ad5/NZW rabbit ocular model. A treatment using 25 μM Ranpirnase demonstrated the most antiviral efficacy followed by the 2.5 μM Ranpirnase concentration. These Ranpirnase concentrations demonstrated similar antiviral activity to that of the Positive Antiviral Control, 0.5% Cidofovir. The treatment using 0.25 μM Ranpirnase demonstrated some antiviral efficacy, but was not as effective as the higher Ranpirnase concentrations and 0.5% Cidofovir.

The in vivo effects of a Ranpirnase or an Amphinase disclosed herein on other Adenovirus serotypes can be assessed in a manner similar to the one discussed above. Other Adenovirus serotypes include, without limitation, a Human adenovirus B serotype 3 (Ad3), Human adenovirus B serotype 7 (Ad7), Human adenovirus B serotype 11 (Ad11), a Human adenovirus D serotype 8 (Ad8), a Human adenovirus D serotype 13 (Ad13), a Human adenovirus D serotype 19 (Ad19), a Human adenovirus D serotype 37 (Ad37) or a Human adenovirus E serotype 4 (Ad4). In addition, the in vivo effects of a Ranpirnase or an Amphinase disclosed herein on other viruses can be assessed in a manner similar to the one discussed above. Other viruses include, without limitation, a herpes simplex virus (HSV), a varicella-zoster virus (VZV), a picornavirus (enterovirus 70, coxsackie A24) or a poxvirus (Molluscum contagiosum virus, vaccinia).

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:

1. A method of treating a viral conjunctivitis in an individual in need thereof, the method comprising administering multiple times a day to a surface of a conjunctiva and/or eye of the individual a pharmaceutical composition comprising a therapeutic effective amount of at most 2 μg of one or more Ranpirnases and a pharmaceutically-acceptable vehicle,
   wherein administration reduces a symptom associated with the viral conjunctivitis, thereby treating the individual.

2. The method according to claim 1, wherein the viral conjunctivitis is an epidemic keratoconjunctivitis, a pharyngoconjunctival fever, a nonspecific sporadic follicular conjunctivitis, or a chronic papillary conjunctivitis.

3. The method according to claim 1, wherein the viral conjunctivitis is cause by a Human adenovirus B, a Human adenovirus D, a Human adenovirus E or any combination thereof.

4. The method according to claim 3, wherein the Human adenovirus B is a Human adenovirus B serotype 3, a Human adenovirus B serotype 7, a Human adenovirus B serotype 11, or any combination thereof.

5. The method according to claim 3, wherein the Human adenovirus D is a Human adenovirus D serotype 8, a Human adenovirus D serotype 13, a Human adenovirus D serotype 19, a Human adenovirus D serotype 37, or any combination thereof.

6. The method according to claim 3, wherein the Human adenovirus E is a Human adenovirus E serotype 4.

7. The method according to claim 1, wherein administration of the one or more Ranpirnase has an antiviral activity that reduces or suppresses a level of virus or viral titer in an individual.

8. The method according to claim 1, wherein administration of the one or more Ranpirnase has an antiviral activity that reduces or suppresses viral replication.

9. The method according to claim 1, wherein administration of the one or more Ranpirnase has an antiviral activity that reduces or suppresses protein synthesis in one or more cells of an individual.

10. The method according to claim 1, wherein administration of the one or more Ranpirnase has an antiviral activity that reduces or suppresses a level of tRNA in one or more cells of an individual.

11. The method according to claim 1, wherein the pharmaceutical composition is formulated as an ophthalmic formulation for use in an ophthalmic route of administration.

12. The method according to claim 11, wherein the pharmaceutical composition further comprises one or more pharmaceutically-acceptable carriers and optionally one or more pharmaceutically-acceptable components.

13. The method according to claim 11, wherein the ophthalmic formulation is a liquid formulation, a colloidal formulation, a semi-solid formulation or a solid formulation.

14. The method according to claim 11, wherein the ophthalmic formulation is administered by an ocular instillation, an ocular irrigation, an intraocular injection, an intracorneal injection, intravitreal injection or a subconjunctival injection.

15. The method according to claim 11, wherein the ophthalmic formulation is a controlled release delivery platform.

16. The method or use according to claim 15, wherein the controlled release delivery platform is an extended release formulation or a sustained release formulation.

17. The method according to claim 11, wherein the ophthalmic formulation is an ocular implant, an ophthalmic implant, a punctal plug, an intraocular implant, an intracorneal implant or a subconjunctival implant.

18. The method according to claim 1, wherein the Ranpirnase has the N-terminus blocked pyroglutamic acid or pyrrolidone carboxylic acid.

19. The method according to claim 1, wherein the pharmaceutical composition is administered four times a day.

20. The method according to claim 1, wherein the pharmaceutical composition is administered eight times a day.

* * * * *

(12) SUPPLEMENTAL EXAMINATION CERTIFICATE

United States Patent
Strem

(10) Number: US 9,682,130 F1
(45) Certificate Issued: Aug. 31, 2018

Control No.: 96/000,262  
Primary Examiner: Johnny F. Railey II

Filing Date: Jun. 28, 2018

No substantial new question of patentability is raised in the request for supplemental examination. See the Reasons for Substantial New Question of Patentability Determination in the file of this proceeding.

(56) Items of Information

U.S. PATENT DOCUMENTS

| | | |
|---|---|---|
| US 8518399 | 8/2013 | Saxena et al. |
| US 8551480 | 10/2013 | Chang et al. |
| US 8663964 | 3/2014 | Saxena et al. |
| US 8808690 | 8/2014 | Saxena et al. |
| US 9642794 | 5/2017 | Sulley et al. |
| US 2015/0010524 | 1/2015 | Jain |
| US 2004/0141967 | 7/2004 | van de Winkel |
| US 2009/0047665 | 2/2009 | Hall et al. |
| US 2007/0155681 | 7/2007 | Shapiro et al. |

FOREIGN PATENT DOCUMENTS

| | | |
|---|---|---|
| WO | 2015/110429 | 7/2015 |
| WO | 2013/165816 | 11/2013 |

OTHER DOCUMENTS

Suhasini et al, "Transfer RNA Cleavages by Onconase Reveal Unusual Cleavage Sites," J. Biol. Chem. 281(18):12201-12209 (2006)